US011867689B2

(12) United States Patent
Nguyen et al.

(10) Patent No.: US 11,867,689 B2
(45) Date of Patent: *Jan. 9, 2024

(54) ENGINEERED RENAL TISSUES, ARRAYS THEREOF, AND METHODS OF MAKING THE SAME

(71) Applicant: Organovo, Inc., San Diego, CA (US)

(72) Inventors: Deborah Lynn Greene Nguyen, San Diego, CA (US); Shelby Marie King, San Diego, CA (US); Sharon C. Presnell, San Diego, CA (US)

(73) Assignee: ORGANOVO, INC., San Diego, CA (US)

( * ) Notice: Subject to any disclaimer, the term of this patent is extended or adjusted under 35 U.S.C. 154(b) by 282 days.

This patent is subject to a terminal disclaimer.

(21) Appl. No.: 17/212,480

(22) Filed: Mar. 25, 2021

(65) Prior Publication Data
US 2021/0208132 A1 Jul. 8, 2021

Related U.S. Application Data

(60) Division of application No. 16/154,447, filed on Oct. 8, 2018, now Pat. No. 10,962,526, which is a continuation of application No. 15/259,264, filed on Sep. 8, 2016, now Pat. No. 10,094,821, which is a continuation of application No. 14/876,659, filed on Oct. 6, 2015, now Pat. No. 9,481,868.

(60) Provisional application No. 62/140,285, filed on Mar. 30, 2015, provisional application No. 62/060,416, filed on Oct. 6, 2014.

(51) Int. Cl.
*G01N 33/50* (2006.01)
*C12N 5/071* (2010.01)

(52) U.S. Cl.
CPC ....... *G01N 33/5014* (2013.01); *C12N 5/0684* (2013.01); *C12N 5/0697* (2013.01); *G01N 33/5044* (2013.01); *C12N 2502/1323* (2013.01); *C12N 2502/256* (2013.01); *C12N 2502/28* (2013.01); *G01N 2500/02* (2013.01); *G01N 2500/10* (2013.01)

(58) Field of Classification Search
CPC ........... G01N 33/5014; G01N 33/5044; C12N 5/0684; C12N 5/0697; C12N 2502/1323; C12N 2502/256; C12N 2502/28
See application file for complete search history.

(56) References Cited

U.S. PATENT DOCUMENTS

| | | | |
|---|---|---|---|
| 4,759,764 A | 7/1988 | Fawcett et al. | |
| 4,808,435 A | 2/1989 | Cropp et al. | |
| 5,099,090 A | 3/1992 | Allan et al. | |
| 6,315,469 B1 | 11/2001 | Alvarez et al. | |
| 6,401,795 B1 | 6/2002 | Cesarano, III et al. | |
| 6,454,972 B1 | 9/2002 | Morisette et al. | |
| 6,520,997 B1 | 2/2003 | Pekkarinen et al. | |
| 6,537,567 B1 | 3/2003 | Niklason et al. | |
| 6,561,607 B1 | 5/2003 | Lubinsky et al. | |
| 6,642,243 B1 | 11/2003 | Imanzahrai | |
| 6,713,772 B2 | 3/2004 | Goodman et al. | |
| 6,939,489 B2 | 9/2005 | Moszner et al. | |
| 6,942,830 B2 | 9/2005 | Muelhaupt et al. | |
| 6,979,670 B1 | 12/2005 | Lyngstadaas et al. | |
| 6,986,739 B2 | 1/2006 | Warren et al. | |
| 7,051,654 B2 | 5/2006 | Boland et al. | |
| 7,196,842 B2 | 3/2007 | Weigl et al. | |
| 7,484,837 B2 | 2/2009 | Koga et al. | |
| 7,625,198 B2 | 12/2009 | Lipson et al. | |
| 7,651,665 B2 | 1/2010 | Gonzalez et al. | |
| 7,680,555 B2 | 3/2010 | Dunn et al. | |
| 7,767,446 B2 | 8/2010 | Robbins et al. | |
| 8,084,424 B2 | 12/2011 | Kishore et al. | |
| 8,143,055 B2 | 3/2012 | Forgacs et al. | |
| 8,241,905 B2 | 8/2012 | Forgacs et al. | |
| 8,343,740 B2 | 1/2013 | Gonda et al. | |
| 8,580,546 B2 | 11/2013 | Gonda et al. | |
| 8,728,807 B2 | 5/2014 | Forgacs et al. | |
| 8,747,880 B2 | 6/2014 | Forgacs et al. | |
| 8,852,932 B2 | 10/2014 | Forgacs et al. | |
| 8,931,880 B2 | 1/2015 | Murphy et al. | |

(Continued)

FOREIGN PATENT DOCUMENTS

CA 2306346 A1 1/1999
EP 2090584 A1 8/2009

(Continued)

OTHER PUBLICATIONS

DesRocher et al. Bioengineered 3D Human Kidney Tissue, a Platform for the Determination of Nephrotoxicity. PLoS One 8(3): e59219. p. 1-12 (Year: 2013).*
Birn et al. Renal albumin absorption in physiology and pathology. Kidney International (2006) 69, 440-449. (Year: 2006).*
ATCC Product Catalog MCF7 (ATCC® HTB-22TM) https://www.atcc.org/products/all/HTB-22.aspx?slp=1#generalinformation, retrieved Sep. 18, 2015.
ATCC Product catalog Primary Subcutaneous Pre-adipocytes; Normal, Human (ATCC® PCS-210-01OTM) https://www.atcc.org/Products/All/PCS-210-010.aspx?slp=1, retrieved Sep. 18, 2015.

(Continued)

Primary Examiner — Taeyoon Kim
(74) Attorney, Agent, or Firm — STERNE, KESSLER, GOLDSTEIN & FOX P.L.L.C.

(57) ABSTRACT

Disclosed are renal tissues and arrays thereof that include a layer of renal interstitial tissue, the renal interstitial tissue comprising renal fibroblasts and endothelial cells; and a layer of renal epithelial tissue, the renal epithelial tissue comprising renal tubular epithelial cells, the renal epithelial tissue in contact with the layer of renal interstitial tissue to form a three-dimensional, engineered, biological renal tissue. Also disclosed are methods of fabricating and using the same.

20 Claims, 25 Drawing Sheets

(15 of 25 Drawing Sheet(s) Filed in Color)

(56) References Cited

U.S. PATENT DOCUMENTS

| | | |
|---|---|---|
| 9,149,952 B2 | 10/2015 | Murphy et al. |
| 9,481,868 B2 | 11/2016 | Nguyen et al. |
| 10,094,821 B2 | 10/2018 | Nguyen et al. |
| 10,962,526 B2 | 3/2021 | Nguyen et al. |
| 2001/0042942 A1 | 11/2001 | Hizumi et al. |
| 2002/0171178 A1 | 11/2002 | Dean et al. |
| 2002/0182633 A1 | 12/2002 | Chen et al. |
| 2002/0188349 A1 | 12/2002 | Mcallister et al. |
| 2003/0049839 A1 | 3/2003 | Romero-Ortega et al. |
| 2003/0149505 A1 | 8/2003 | Mogensen |
| 2003/0153078 A1 | 8/2003 | Libera et al. |
| 2003/0175410 A1 | 9/2003 | Campbell et al. |
| 2003/0236588 A1 | 12/2003 | Jang et al. |
| 2004/0006405 A1 | 1/2004 | Chen et al. |
| 2004/0132184 A1 | 7/2004 | Dennis et al. |
| 2004/0197367 A1 | 10/2004 | Rezania et al. |
| 2004/0219133 A1 | 11/2004 | Lyles |
| 2004/0253365 A1 | 12/2004 | Warren et al. |
| 2005/0009178 A1 | 1/2005 | Yost et al. |
| 2005/0169962 A1 | 8/2005 | Bhatia et al. |
| 2005/0226856 A1 | 10/2005 | Ahlfors |
| 2005/0276791 A1 | 12/2005 | Hansford et al. |
| 2006/0099287 A1 | 5/2006 | Kim et al. |
| 2006/0198918 A1 | 9/2006 | Koyagi et al. |
| 2006/0237880 A1 | 10/2006 | Wicker et al. |
| 2006/0270032 A1 | 11/2006 | Bhatia et al. |
| 2007/0142916 A1 | 6/2007 | Olson et al. |
| 2007/0200276 A1 | 8/2007 | Mackey et al. |
| 2007/0231787 A1 | 10/2007 | Voelker |
| 2007/0299508 A1 | 12/2007 | Morrison et al. |
| 2008/0027114 A1 | 1/2008 | Funke et al. |
| 2008/0070304 A1 | 3/2008 | Forgacs et al. |
| 2008/0097575 A1 | 4/2008 | Cottone |
| 2008/0192074 A1 | 8/2008 | Dubois et al. |
| 2008/0193910 A1 | 8/2008 | Larkin et al. |
| 2009/0076531 A1 | 3/2009 | Richardson et al. |
| 2009/0117087 A1 | 5/2009 | Carroll et al. |
| 2009/0142307 A1 | 6/2009 | Athanasiou et al. |
| 2009/0206522 A1 | 8/2009 | Hein et al. |
| 2009/0208466 A1 | 8/2009 | Yoo et al. |
| 2009/0208577 A1 | 8/2009 | Xu et al. |
| 2009/0239302 A1 | 9/2009 | Decher et al. |
| 2009/0248145 A1 | 10/2009 | Chan et al. |
| 2009/0267269 A1 | 10/2009 | Lim et al. |
| 2010/0041134 A1 | 2/2010 | Forgacs et al. |
| 2010/0056390 A1 | 3/2010 | Fischbach |
| 2010/0160183 A1 | 6/2010 | Xu et al. |
| 2010/0191360 A1 | 7/2010 | Napadensky et al. |
| 2010/0254900 A1 | 10/2010 | Campbell et al. |
| 2011/0064784 A1 | 3/2011 | Mullens et al. |
| 2011/0172611 A1 | 7/2011 | Yoo et al. |
| 2011/0180914 A1 | 7/2011 | Do et al. |
| 2011/0212501 A1 | 9/2011 | Yoo |
| 2011/0250688 A1 | 10/2011 | Hasan |
| 2012/0045770 A1 | 2/2012 | Pongracz et al. |
| 2012/0089238 A1 | 4/2012 | Kang et al. |
| 2013/0108726 A1 | 5/2013 | Uckelmann et al. |
| 2013/0164339 A1 | 6/2013 | Murphy et al. |
| 2013/0190210 A1 | 7/2013 | Murphy et al. |
| 2013/0193619 A1 | 8/2013 | Church et al. |
| 2013/0236431 A1 | 9/2013 | Gourdie et al. |
| 2013/0236879 A1 | 9/2013 | Berry et al. |
| 2013/0345794 A1 | 12/2013 | Khatiwala et al. |
| 2014/0012225 A1 | 1/2014 | Yoo et al. |
| 2014/0044822 A1 | 2/2014 | Mulliken |
| 2014/0093932 A1 | 4/2014 | Murphy et al. |
| 2014/0099709 A1 | 4/2014 | Presnell et al. |
| 2014/0131313 A1 | 5/2014 | Wakamatsu et al. |
| 2014/0220685 A1 | 8/2014 | Forgacs et al. |
| 2014/0265049 A1 | 9/2014 | Burris et al. |
| 2014/0274802 A1 | 9/2014 | Shepherd et al. |
| 2014/0287960 A1 | 9/2014 | Shepherd et al. |
| 2014/0358273 A1 | 12/2014 | Labossiere et al. |
| 2015/0004273 A1 | 1/2015 | Forgacs et al. |
| 2015/0037445 A1 | 2/2015 | Murphy et al. |
| 2015/0057786 A1 | 2/2015 | Murphy et al. |
| 2022/0229045 A1 | 7/2022 | King et al. |

FOREIGN PATENT DOCUMENTS

| | | |
|---|---|---|
| JP | 2001038981 A | 2/2001 |
| JP | 2003-169845 A | 6/2003 |
| JP | 2005031144 A | 2/2005 |
| JP | 2006159117 A | 6/2006 |
| JP | 2012-080888 A | 4/2012 |
| KR | 20090087748 A | 8/2009 |
| RU | 2371758 C2 | 10/2009 |
| WO | WO-9901538 A1 | 1/1999 |
| WO | WO-0168811 A2 | 9/2001 |
| WO | WO-2004108418 A1 | 12/2004 |
| WO | WO-2005025493 A2 | 3/2005 |
| WO | WO-2005081970 A2 | 9/2005 |
| WO | WO-2007076272 A2 | 7/2007 |
| WO | WO-2007115336 A2 | 10/2007 |
| WO | WO-2007115337 A2 | 10/2007 |
| WO | WO-2007124023 A2 | 11/2007 |
| WO | WO-2007125893 A1 | 11/2007 |
| WO | WO-2007126411 A2 | 11/2007 |
| WO | WO-2007136936 A2 | 11/2007 |
| WO | WO-2009102484 A2 | 8/2009 |
| WO | WO-2009154466 A1 | 12/2009 |
| WO | WO-2010008905 A2 | 1/2010 |
| WO | WO-2011038373 A2 | 3/2011 |
| WO | WO-2011088213 | 7/2011 |
| WO | WO-2011097330 A2 | 8/2011 |
| WO | WO-2011107599 A1 | 9/2011 |
| WO | WO-2011119059 A1 | 9/2011 |
| WO | WO-2012003465 A2 | 1/2012 |
| WO | WO-2012054195 A2 | 4/2012 |
| WO | WO-2012131000 A1 | 10/2012 |
| WO | WO 2013/067498 A1 | 5/2013 |
| WO | WO-2013130823 A1 | 9/2013 |
| WO | WO-2013192290 A1 | 12/2013 |
| WO | WO 2014/151921 A1 | 9/2014 |
| WO | WO-2015066705 A1 | 5/2015 |

OTHER PUBLICATIONS

Baltich et al. Development of a Scaffoldless Three-Dimensional Engineered Nerve Using a Nerve-Fibroblast Co-Culture. In Vitro Cell. Dev. Biol.—Animal 46:438-444 (2010).

Bioscaffolder 2008, www.syseng.de, SYSENG Dipl.-Ing. Hendrik John.

Boland et al. Application of inkjet printing to tissue engineering. Biotech J. 1:910-917 (2006).

Boland et al. Cell and Organ Printing 2: Fusion of Cell Aggregates in Three-Dimensional Gels. The Anatomical Record, Part A. 272A:497-502 (2003).

Bunnell et al. Adipose-derived Stem Cells: Isolation, Expansion and Differentiation. Methods 45(2):115-120 (2008).

Chaterji et al. Scaffold-Free In Vitro Arterial Mimetics: The Importance of Smooth Muscle-Endothelium Contact. Tissue Engineering Part A 16(8):1901-1912 (2010).

'Sciperio, Inc. 2003 R&D 100 Award Winner. Sciperio, http://www.sciperio.com/news/20031016.asp, accessed on Feb. 1, 2005, 2 pages.

CONSTANS. Body by Science. The Scientist 17(19):34-37 http://www.the-scientist.com/article/display/141541 (2003).

Co-pending U.S. Appl. No. 14/678,392, filed Apr. 3, 2015.

Co-pending U.S. Appl. No. 14/796,910, filed Jul. 10, 2015.

Co-pending U.S. Appl. No. 14/827,152, filed Aug. 14, 2015.

Dai et al. Fibroblast Aggregation by Suspension with Conjugates of Poly(ethylene glycol) and RGD. Biotechnology and Bioengineering 50(4):349-356 (May 20, 1996).

Dirat et al. Cancer-associated adipocytes exhibit an activated phenotype and contribute to breast cancer invasion. Cancer Res. 71(7):2455-2465 (2011).

Dominici et al. Minimal criteria for defining multipotent mesenchymal stromal cells, International Society for Cellular Therapy position statement. Cytotherapy 8(4):315-317 (2006).

(56) References Cited

OTHER PUBLICATIONS

Edelman. Vascular Tissue Engineering: Designer Arteries. Circ Res 85(12):1115-1117 (1999).
Egebald et al. Tumors as organs: complex tissues that interface with the entire organism. Dev Cell. 18(6):884-901 (2010).
Eisenberg et al. Bone Marrow Cells Transdifferentiate to Cardiomyocytes When Introduced into the Embryonic Heart. Stem Cells 24:1236-1245 (2006).
Fedorovich et al. Distinct Tissue Formation by Heterogeneous Printing of Osteo- and Endothelial Progenitor Cells. Tissue Engineering: Part A 17(15-16):2113-2123 (2011).
Fedorovich et al. Three-Dimensional Fiber Deposition of Cell-Laden, Viable Patterned Constructs for Bone Tissue Printing, Tissue Engineering: Part A 14(1):127-135 (2008).
Forgacs et al. Biological Relevance of Tissue Liquidity and Viscoelasticity Eds. A. Deutsch, M. Falcke, J. Howard and W. Zimmermann. Birkhauser. pp. 269-277 (2004).
Forgacs et al. Viscoelastic Properties of Living Embryonic Tissues: A Quantitative Study, Biophysical Journal 74(5):2227-2234 (May 1998).
Foty et al. Surface Tensions of Embryonic Tissues Predict Their Mutual Envelopment Behavior. Development 122(5):1611-1620 (1996).
Foty et al. The Differential Adhesion Hypothesis: A Direct Evaluation. Developmental Biology 278(1):255-263 (2005).
Frisman et al. Nanostructuring of PEG-fibrinogen polymeric scaffolds. Acta Biomaterialia 6(7):2518-2524 (2009).
Fuellhase et al. 264 Generation Of Organized Bladder Tissue Constructs Using A Novel Hybrid Printing System. European Urology Supplements 8(4):186 (2009).
Furukawa et al. Formation of Human Fibroblast Aggregates (Spheroids) by Rotational Culture. Cell Transplantation 10(4-5):441-445 (2001).
Furukawa et al. Scaffold-free cartilage tissue by mechanical stress loading for tissue engineering. In Tissue Engineering, ed by Daniel Eberli. InTech p. 409-428 (2010).
Furukawa et al. Tissue-engineered Skin Using Aggregates of Normal Human Skin Fibroblasts and Biodegradable Material. J. MK Organs 4:353-356 (2001).
Ghorbanian et al. Microfluidic direct writer with integrated declogging mechanism for fabricating cell-laden hydrogel constructs. Biomed Microdevices (doi: 10.1007/s10544-014-9842-8), Springer Science+Business Media New York 2014 (Mar. 4, 2014).
Glazier et al. Simulation of the Differential Adhesion Driven Rearrangement of Biological Cells. Physical Review E 47(3):2128-2154 (Mar. 1993).
Glicklis et al. Modeling Mass Transfer in Hepatocyte Spheroids Via Cell Viability, Spheroid Size, and Hepatocellular Functions. Biotechnology and Bioengineering 86(6):672-680 (Jun. 20, 2004).
Graner et al. Simulation of Biological Cell Sorting Using a Two-Dimensional Extended Potts Model. Physical Review Letters 69(13):2013-2016 (Sep. 28, 1992).
Grange et al. Isolation and characterization of human breast tumor-derived endothelial cells. Oncol Rep. 15(2):381-386 (2006).
Gruene et al. Laser Printing of Stem Cells for Biofabrication of Scaffold-Free Autologous Grafts. Tissue Engineering: Part C 17(1):79-89 (2011).
Gruene et al. Laser printing of three-dimensional multicellular arrays for studies of cell-cell and cell-environment interactions. Tissue Eng Part C Methods 17(10):973-82 (Oct. 2011).
Guenard et al. Syngeneic Schwann Cells Derived from Adult Nerves Seeded in Semipermeable Guidance Channels Enhance Peripheral Nerve Regeneration. The Journal of Neuroscience 12(9):3310-3320 (Sep. 1992).
Guillemot et al. High-throughput laser printing of cells and biomaterials for tissue engineering. Acta biomaterialia 6:2494-2500 (2010).
Hadlock et al. A Polymer Foam Conduit Seeded with Schwann Cells Promotes Guided Peripheral Nerve Regeneration. Tissue Engineering 6(2):119-127 (2000).

Halley et al. Growing Organs In the Lab. Longevity. 1-7 (Jun. 2009).
Harvey et al. Schwann cells and fetal tectal tissue cografted to the midbrain of newborn rats: fate of Schwann cells and their influence on host retinal innervation of grafts. Exp Neurol. 134(2):179-91 (1995).
Hockaday et al. Rapid 3D printing of anatomically accurate and mechanically heterogeneous aortic valve hydrogel scaffolds. Biofabrication 4(3):1-12 (2012).
Hubbard et al. Bioengineered, Autologous, Scaffold-free Nerve Conduit for Peripheral Nerve Repair. Abstract. AAHS/ASPN/ASRM 2011, Annual Scientific Meetings Program Book. pp. 140 and 159 (Jan. 12-18, 2011).
Ito et al. Novel Methodology for Fabrication of Tissue-Engineered Tubular Constructs Using Magnetite Nanoparticles and Magnetic Force, Tissue Engineering, Larchmont, NY, US, 11(9-10):1553-1561 (2005).
Iwasaki et al. Bioengineered Three-Layered Robust and Elastic Artery Using Hemodynamically-Equivalent Pulsatile Bioreactor. Circulation 18(14 Suppl):S53-S57 (2008).
Izaguirre et al. CompuCell, a multi-model framework for simulation of morphogenesis. Bioinformatics 20(7):1129-1137 (2004).
Jakab et al. Engineering Biological Structures of Prescribed Shape Using Self-assembling Multicellular Systems. PNAS USA 101:2864-2869 (2004).
Jakab et al. Organ printing: fiction or science. Biorheology 43(3-4):371-375 (2004).
Jakab et al. Relating Cell and Tissue Mechanics: Implications and Applications. Developmental Dynamics 237:2438-2449 (2008).
Jakab et al. Three-dimensional tissue constructs built by bioprinting. Biorheology 43(3-4):509-513 (2006).
Jakab et al. Tissue Engineering by Self-Assembly and Bio-printing of living cells. Biofabrication 2(2):022001 (14 pp) (Jun. 2, 2010).
Jakab et al. Tissue Engineering by Self-Assembly of Cells Printed into Topologically Defined Structures. Tissue Engineering: Part A. 14:413-421 (Nov. 3, 2008).
Kasko. Degradable Poly(ethylene glycol) Hydrogels for 2D and 3D Cell Culture. Aldrich Materials Science, pp. 67-75 (no date available).
Kelm et al. Design of Custom-Shaped Vascularized Tissues Using Microtissue Spheriods as Minimal Building Units. Tissue Engineering 12(8):2151-2160 (2006).
Kelm et al. Microscale Tissue Engineering Using Gravity-Enforced Cell Assembly. Trends in Biotechnology 22(4):195-202 (Apr. 2004).
Khatiwala et al. 3D Cell Bioprinting for Regenerative Medicine Research and Therapies. Gene Therapy and Regulation 7(1):1-19 (2012).
King et al. Development of 3D bioprinted human breast cancer for in vitro screening of therapeutics targeted against cancer progression. IEEE The American Society for Cell biology. 2013 ascb annual meeting. New Orleans: IEEE Dec. 14-18, 2013.
Koibuchi et al. Behavior of Cells in Artificially Made Cell Aggregates and Tissue Fragments after Grafting to Developing Hind Limb Buds in Xenopus laevis. The International Journal of Developmental Biology 43(2):141-148 (1999).
Korff et al. Blood Vessel Maturation in a 3-Dimensional Spheroidal Coculture Model: Direct Contact with Smooth Muscle Cells Regulates Endothelial Cell Quiescence and Abrogates VEGF Responsiveness. The FASEB Journal 15:447-457 (Feb. 2001).
Larkin et al. Structure and Functional Evaluation of Tendon-Skeletal Muscle Constructs Engineered in Vitro. Tissue Eng. 12(11):3149-3158 (Nov. 2006).
Lee et al. Multi-layered Culture of Human Skin Fibroblasts and Keratinocytes Through Three-dimensional Freeform Fabrication. Biomaterials 30:1587-1595 (2009).
L'Heureux et al. A completely biological tissue-engineered human blood vessel. The FASEB Journal 12 (1):47-56 (1998).
L'Heureux et al. Human tissue-engineered blood vessels for adult arterial revascularization. Nature Medicine 12 (3):361-365 (2006).
L'Heureux et al. Sheet-Based Tissue Engineering From Bench Top to the First Clinical Use of a Completely Biological Tissue Engineered Vessel. The FASEB Journal 12(1):47-56 (Abstract) (2006).

(56) References Cited

OTHER PUBLICATIONS

Luo et al. Three-dimensional microtissue assay for high-throughput cytotoxicity of nanoparticles. Anal Chem. 84(15):6731-6738 (Aug. 7, 2012).
Marga et al. Bioprint Engineered Fully Biological Nerve Graft. Poster Presentation TERMIS Dec. 5-8, 2010, Orlando, Florida, 1 page.
Marga et al. Construction of a Bioprinted Fully Biological Nerve Graft. Biophysical Journal 96(3 supp 1):643a Abstract (Feb. 2009).
Marga et al. Developmental Biology and Tissue Engineering, Birth Defects Research (Part C) 81:320-328 (2007).
Marga et al. Engineered Fully Biological Nerve Graft. Oral Presentation, International Conference on Biofabrication, Oct. 3-6, 2010, Philadelphia, Pennsylvania, 1 page.
Marga et al. Engineered Fully Biological Nerve Graft. Poster Presentation Biophysical Society Meeting, Mar. 4, 2009, 1 page.
Marga et al. Toward Engineering Functional Organ Modules by Additive Manufacturing. Biofabrication 4:022001 (12 pp) (2012).
Martin et al. Computer-Based Technique for Cell Aggregation Analysis and Cell Aggregation in In Vitro Chondrogenesis. Cytometry 28(2):141-146 (1997).
Mcguigan et al. Vascularized organoid engineered by modular assembly enables blood perfusion. PNAS, 103(31):11461-11466 (2006).
Mehesz et al. Scalable robotic biofabrication of tissue spheroids. Biofabrication 3:1-8 (2011).
Mironov et al. Bioprinting Living Structures. J. Mat. Chem. 17:2054-2060 (2007).
Mironov et al. Organ Printing: Computer-Aided Jet-Based 3D Tissue Engineering. Trends in Biotechnology 21(4):157-161 (Apr. 2003).
Mironov et al. Organ Printing: Self-Assembling Cell Aggregates as 'Bioink'. Science & Medicine 9(2):69-71 (Apr. 2003).
Mironov et al. Organ Printing: Tissue Spheroids as Building Blocks. Biomaterials 30:2164-2174 (2009).
Mizumoto et al. Formation of Cylindrical Multicellular Aggregate (Cylindroid) and Express of Liver Specific Functions of Primary Rat Hepatocytes. Cytotechnology 31:69-75 (1999).
Mombach et al. Quantitative Comparison Between Differential Adhesion Models and Cell Sorting in the Presence and Absence of Fluctuations. Physical Review Letters 75(11):2244-2247 (Sep. 11, 1995).
Moon et al. Layer by Layer Three-dimensional Tissue Epitaxy by Cell-Laden Hydrogel Droplets. Tissue Engineering Part C: Methods 16(1):157-166 (2010).
Mroue et al. Three-dimensional cultures of mouse mammary epithelial cells. Methods Mol Biol. 945:221-250 (2013).
Neagu et al. Role of physical mechanisms in biological self-organization. Phys RevLett 95(17):178104 (2005).
Newman et al. Before programs: the physical origination of multicellular forms. Int J Dev Biol. 50(2-3):289-299 (2006).
Nickerson et al. Three-Dimensional Tissue Assemblies: Novel Models for the Study of *Salmonella enterica* Serovar Typhimurium Pathogenesis. Infection and Immunity 69(11):7106-7120 (Nov. 2001).
Niklason et al. Advances in Tissue Engineering of Blood Vessels and Other Tissues. Transpl. Immunol. 5(4):303-306 (1997).
Norotte et al. Scaffold-free vascular tissue engineering using bioprinting. Biomaterials 30:5910-5917 (2009).
Panagiotis et al. A unique aged human retinal pigmental epithelial cell line useful for studying lens differentiation in vitro. International Journal of Developmental Biology 45:753-758 (2001).
Pathology Outlines: Bladder. Normal Histology. pp. 1-4 (2011).
Paul et al. How to improe R&D productivity: the pharmaceutical industry's grand challenge. Nature Reviews Drug Discovery 9(3):203-214 (2010).
PCT/US2005/05735 International Search Report dated Dec. 7, 2007.
PCT/US2005/05735 International Preliminary Report on Patentability dated Mar. 3, 2009.
PCT/US2009/48530 International Preliminary Report on Patentability dated Jan. 13, 2011.
PCT/US2009/48530 International Search Report dated Mar. 15, 2010.
PCT/US2011/023520 International Preliminary Report on Patentability dated Aug. 16, 2012.
PCT/US2011/023520 International Search Report dated Oct. 31, 2011.
PCT/US2011/028713 International Preliminary Report on Patentability dated Sep. 18, 2012.
PCT/US2011/028713 International Search Report dated Nov. 30, 2011.
PCT/US2011/053515 International Preliminary Report on Patentability dated May 3, 2013.
PCT/US2011/053515 International Search Report and Written Opinion dated May 1, 2012.
PCT/US2012/054923 International Preliminary Report on Patentability dated Mar. 20, 2014.
PCT/US2012/054923 International Search Report dated Feb. 26, 2013.
PCT/US2012/054935 International Preliminary Report on Patentability dated Mar. 20, 2014.
PCT/US2012/054935 International Search Report dated Feb. 28, 2013.
PCT/US2013/036479 International Preliminary Report on Patentability dated Oct. 21, 2014.
PCT/US2013/036479 International search report dated Jul. 25, 2013.
PCT/US2013/046519 International Preliminary Report on Patentability dated Dec. 23, 2014.
PCT/US2013/046519 International Search Report dated Sep. 5, 2013.
PCT/US2014/026679 International Preliminary Report on Patentability dated Sep. 24, 2015.
PCT/US2014/026679 International Search Report and Written Opinion dated Jul. 22, 2014.
PCT/US2014/041419 International Search Report and Written Opinion dated Jan. 2, 2015.
PCT/US2014/048962 International Search Report and Written Opinion dated Nov. 10, 2014.
Perez-Pomares et al. Tissue Fusion and Cell Sorting in Embryonic Development and Disease: Biomedical Implications. Bioessays 28:809-821 (2006).
Remuzzi et al. Vascular Smooth Muscle Cells on Hyaluronic Acid: Culture and Mechanical Characterization of an Engineered Vascular Construct. Tissue Engineering 10(516):699-710 (2004).
Riken. Self-healing hydrogels ease into production. Research Highlights: Materials. Downloaded from the Riken website: <http://www.riken.jp/en/research/rikenresearch/highlights/7543/> (Nov. 1, 2013) [accessed Apr. 27, 2015].
Ryan et al. Tissue Spreading on Implantable Substrates is a Competitive Outcome of Cell-Cell vs. Cell-Substratum Adhesivity. PNAS 98(8):4323-4327 (Apr. 10, 2001).
Schuster et al. Why Drugs Fail—A Study on Side Effects in New Chemical Entities. Curr. Pharm. Des. 11:3545 (2005).
Shafrir et al. Mechanotransduction through the cytoskeleton. American Journal of Physiology 282:479-486 (2002).
Sheehan et al. Recent Patents and Trends in Bioprinting. Recent Patents on Biomedical Engineering 4:26-32 (2011).
Shim et al. Bioprinting of a mechanically enhanced three-dimensional dual cell-laden construct for osteochondral tissue engineering using a multi-head tissue/organ building system. J of Micromechanics and Microengineering. 22(Article No. 085014):1-11 (2012).
Siemionow et al. Current Techniques and Concepts in Peripheral Nerve Repair. Chapter 8, International Review of Neurobiology, 87:141-172 (2009).
Skardal et al. Bioprinting vessel-like constructs using hyaluronan hydrogels crosslinked with tetrahedral polyethylene glycol tetracrylates. Biomaterials 31:6173-6181 (2010).
Smith. A direct-write three-dimensional Bioassembly tool for regenerative medicine. The University of Arizona pp. 1-291 (Nov. 1, 2005).

(56) References Cited

OTHER PUBLICATIONS

Smith et al. Characterizing Environment Factors that Impact the Viability of Tissue-Engineered Constructs Fabricated by a Direct-Write Bioassembly Tool. Tissue Engineering, 13(2):373-385 (2007).
Smith et al. Three-Dimensional BioAssembly Tool for Generating Viable Tissue-Engineered Constructs. Tissue Engineering 10(9/10):1566-1576 (2004).
Steinberg. Does Differential Adhesion Govern Self-Assembly Processes in Histogenesis? Equilibrium Configurations and the Emergence of a Hierarchy Among Populations of Embryonic Cells. The Journal of Experimental Zoology 173(4):395-433 (Apr. 1970).
Steinberg et al. Liquid Behavior of Embryonic Tissues. Cell Behaviour pp. 583-697 (1982).
Stiles. UA Wins R & D 100 Award for Machine that Prints Tissue Cell-by-Cell. UANews Dec. 2, 2003, http://uanews.org/cgi-binfflebObjects/UANews.woa/wa/goPrint?ArticleID=8305, accessed on Feb. 1, 2005, 2 pages.
Tang et al. Molding of Three-Dimensional Microstructures of Gels. Journal of the American Chemical Society 125(43):12988-12989 (Oct. 29, 2003).
Tao et al. Bio-printing of living organized tissues using an inkjet technology. Database Accession No. PREV200700335042. FASEB Journal 23(5):A636 (2007).
Timmins et al. Hanging-Drop Multicellular Spheroids as a Model of Tumour Angiogenesis. Angiogenesis 7(2):97-103 (2004).
Tsang. Three-Dimensional Tissue Fabrication, Advanced drug delivery reviews 56(11):1635-1647 (2004).
U.S. Appl. No. 10/590,446 Office action dated Jan. 6, 2011.
U.S. Appl. No. 10/590,446 Office action dated Sep. 1, 2011.
U.S. Appl. No. 10/666,836 Office action dated Oct. 28, 2004.
U.S. Appl. No. 11/227,489 Office action dated Dec. 10, 2008.
U.S. Appl. No. 11/227,489 Office action dated Jul. 8, 2009.
U.S. Appl. No. 13/020,000 Office action dated Dec. 31, 2012.
U.S. Appl. No. 13/020,000 Office action dated Jul. 3, 2013.
U.S. Appl. No. 13/246,428 Office Action dated Aug. 26, 2014.
U.S. Appl. No. 13/246,428 Office Action dated Jan. 14, 2015.
U.S. Appl. No. 13/402,215 Office Action dated Mar. 19, 2013.
U.S. Appl. No. 13/529,172 Office action dated Sep. 24, 2013.
U.S. Appl. No. 13/612,768 Office Action dated Jul. 30, 2015.
U.S. Appl. No. 13/612,768 Office Action dated May 30, 2014.
U.S. Appl. No. 13/612,768 Office Action dated Nov. 17, 2014.
U.S. Appl. No. 13/612,768 Office Action dated Oct. 1, 2013.
U.S. Appl. No. 13/612,778 Office Action dated Apr. 28, 2014.
U.S. Appl. No. 13/612,778 Office Action dated Nov. 7, 2014.
U.S. Appl. No. 13/634,863 Office Action dated Jan. 28, 2015.
U.S. Appl. No. 13/634,863 Office Action dated Sep. 8, 2015.
U.S. Appl. No. 13/794,368 Office Action dated May 8, 2015.
U.S. Appl. No. 13/794,368 Office Action dated Nov. 26, 2014.
U.S. Appl. No. 13/801,780 Office Action dated Jun. 5, 2015.
U.S. Appl. No. 13/801,780 Office Action dated Nov. 14, 2014.
U.S. Appl. No. 13/968,313 Office Action dated Jun. 26, 2014.
U.S. Appl. No. 14/295,226 Office Action dated May 7, 2015.
U.S. Appl. No. 14/295,226 Office Action dated Oct. 8, 2014.
U.S. Appl. No. 14/295,226 Office Action dated Sep. 9, 2015.
U.S. Appl. No. 14/447,412 Office Action dated Jul. 15, 2015.
U.S. Appl. No. 14/447,412 Office Action dated Mar. 3, 2015.
U.S. Appl. No. 14/530,499 Office Action dated May 14, 2015.
U.S. Appl. No. 14/678,392 Office Action dated Oct. 8, 2015.
U.S. Appl. No. 14/678,392 Office Action dated Sep. 24, 2015.
U.S. Appl. No. 14/796,910 Office Action dated Sep. 25, 2015.
Wake Forest Baptist Medical Center (Wake Forest Physician Reports First Human Recipients of Laboratory-Grown Organs. 2006 pp. 1-2).
Wang et al. Bone marrow mesenchymal stem cells promote cell proliferation and neurotrophic function of Schwann cells in vitro and in vivo. Brain Research 1262:7-15 (2009).
Xu et al. A three-dimensional in vitro ovarian cancer coculture model using a high-throughput cell patterning platform. Biotechnology Journal 6(2):204-212 (2011).
Xu et al. In vivo generation of functional tissues using the inkjet printing technology. Tissue Engineering 13(7):1713-1714 (2007).
Yamauchi et al. A Three-Dimensional Cell Culture Model for Bovine Endometrium: Regeneration of a Multicellular Spheroid Using Ascorbate. Placenta 24:258-269 (2003).
Zhang et al. Characterization of printable cellular micro-fluidic channels for tissue engineering. Biofabrication 5:025004 (2013).
Corning: Transwell permeable supports selection and use guide. Jun. 2013. downloaded from http://csmedia2.com/LifeSciences/Media/pdf/transwell_guide.pdf. on Feb. 4, 2016. p. 1-12.
Co-pending U.S. Appl. No. 14/933,822, filed Nov. 5, 2015.
Co-pending U.S. Appl. No. 14/936,580, filed Nov. 9, 2015.
Co-pending U.S. Appl. No. 14/950,567, filed Nov. 24, 2015.
Cui et al. Direct Human Cartilage Repair Using Three-Dimensional Bioprinting Technology. Tissue Engineering Part A 18(11-12):1304-1312 (2012).
Fujita et al. Fabrication of scaffold-free contractile skeletal muscle tissue using magnetite-incorporated myogenic C2C12 cells. J Tissue Eng Regen Med. 4(6):437-443 (2010).
Hierlihy et al. The post-natal heart contains a myocardial stem cell population. FEBS Letters 530:239-243 (2002).
Liu et al. Design and Development of Three-Dimensional Scaffolds For Tissue Engineering. Chemical Engineering Research and Design 85(7):1051-1064 (2007).
Pearson Education. Human Heart Illustration (2004).
Tanaka et al. A Valved Hepatic Portoduodenal Instestinal Conduit for Biliary Atresia. Ann. Surg. 213(3):230-235 (1991).
Tsang et al. Fabrication of 3D hepatic tissues by additive photopatterning of cellular hydrogels. The FASEB Journal 21(3):790-801 (2007).
U.S. Appl. No. 13/612,778 Office Action dated Nov. 17, 2015.
U.S. Appl. No. 13/794,368 Office Action dated Sep. 23, 2015.
U.S. Appl. No. 14/244,679 Office Action dated Oct. 23, 2015.
Pampaloni, F. and Stelzer, E.H.K., "Three-Dimensional Cell Cultures in Toxicology," *Biotechnology and Genetic Engineering Reviews* 26:117-138, Taylor & Francis, England (2009).
Office Action dated May 9, 2017, in U.S. Appl. No. 13/612,768, Murphy, K et al., filed Sep. 12, 2012, 15 pages.
Office Action dated Jul. 24, 2017, in U.S. Appl. No. 13/612,768, Murphy, K et al., filed Sep. 12, 2012, 25 pages.
Office Action dated Feb. 9, 2016, in U.S. Appl. No. 14/876,659, Nguyen et al., filed Oct. 6, 2015, 12 pages.
DesRochers, T.M., et al., "Tissue-engineered kidney disease models," *Advanced Drug Delivery Reviews* 69-70:67-80, Elsevier, Netherlands (2014).
DesRochers, T.M., et al., "Bioengineered 3D Human Kidney Tissue, a Platform for the Determination of Nephrotoxicity," 8(3): e59219, *Plos One*, United States (Mar. 2013).
Supplementary European Search Report for European Application No. EP15848294, Munich, Germany, dated Feb. 21, 2018, 13 Pages.
Jansen et al., "Biotechnological challenges of bioartificial kidney engineering," *Biotechnology Advances* 32(7):1317-1327, Elsevier, Netherlands (2014).
King, S., et al., "3D Proximal Tubule Tissues Recapitulate Key Aspects of Renal Physiology to Enable Nephrotoxicity Testing," *Frontiers in Physiology* 8(123):1-18, Frontiers Media, Switzerland (2017).
Abrahamson, et al., "Development of kidney tubular basement membranes," Kidney International, 39: 382-393, International Society of Nephrology, Belhium (1991).
Non-Final Office Action dated Nov. 16, 2017, in U.S. Appl. No. 15/259,264, Nguyen et al., filed Sep. 8, 2016, 7 pages.
Non-Final Office Action dated Apr. 13, 2020, in U.S. Appl. No. 16/154,447, Nguyen et al., filed Oct. 8, 2018, 6 pages.

\* cited by examiner

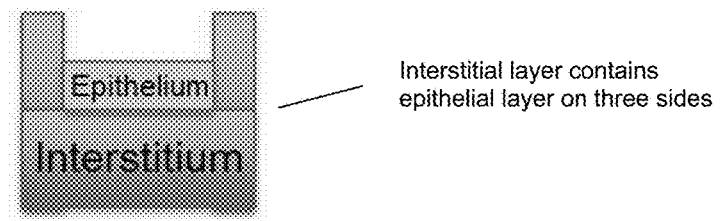
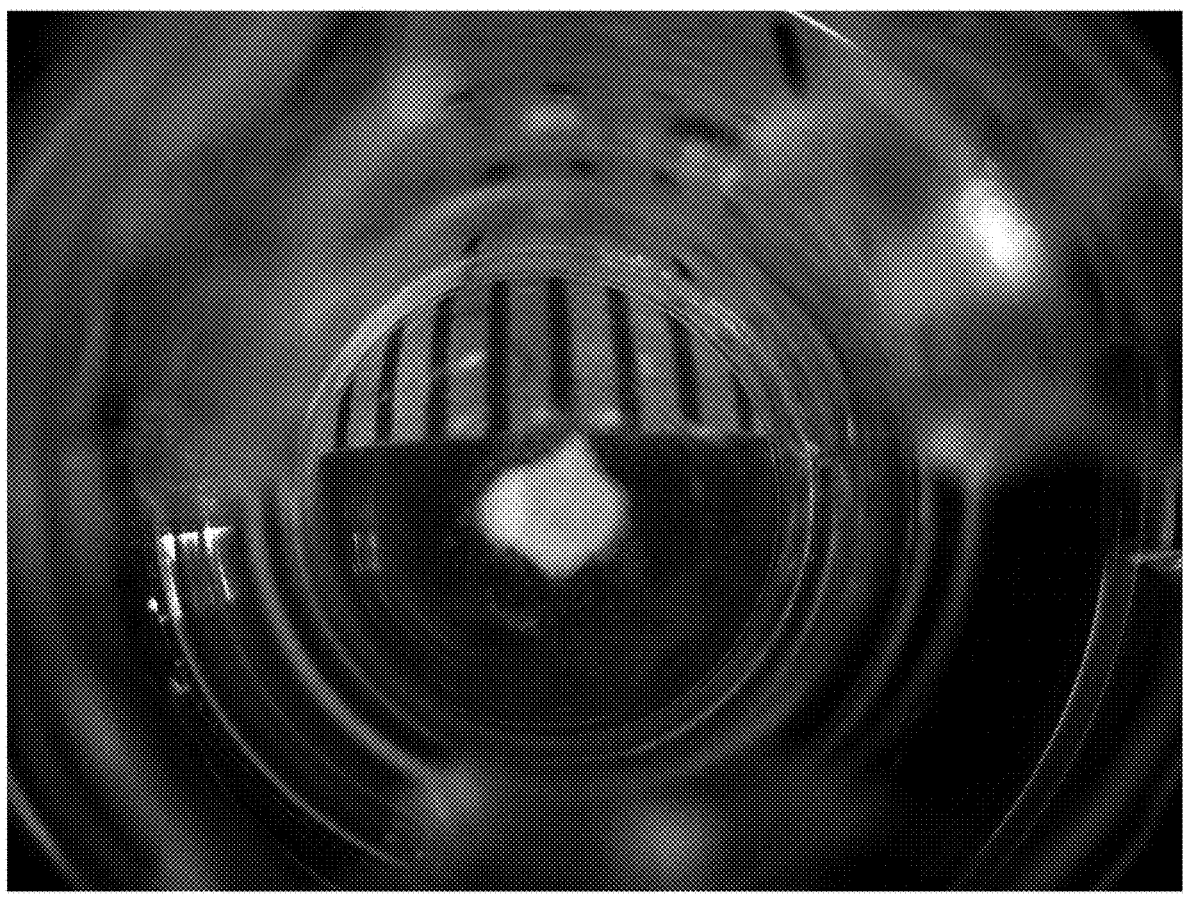
FIG. 2A
FIG. 2B

FIG. 21A  FIG. 21B

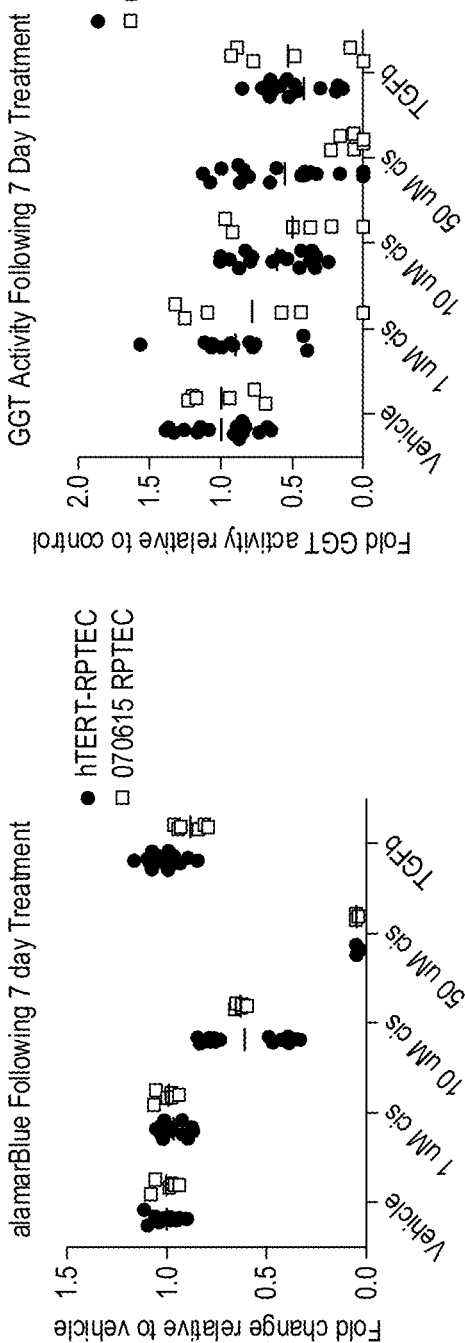
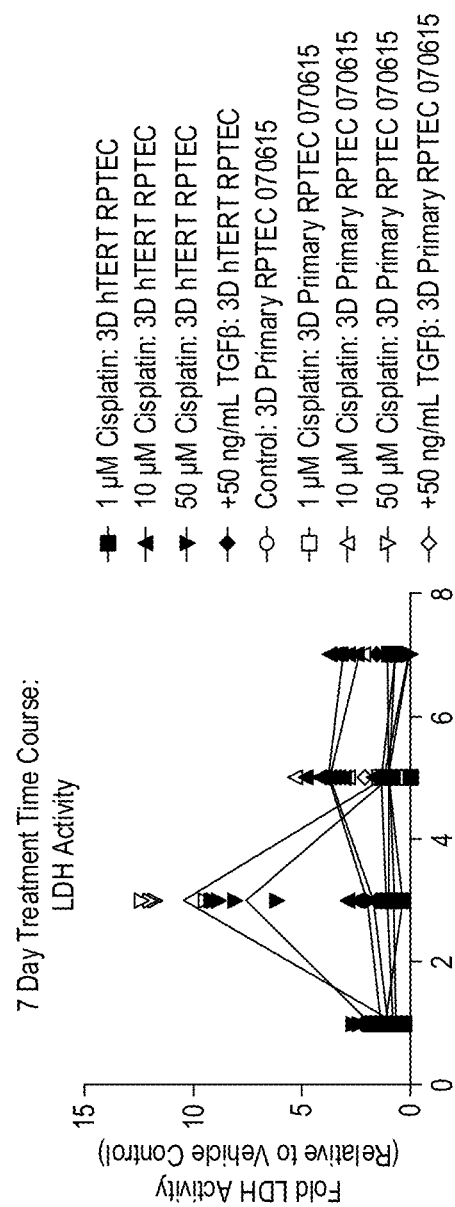
FIG. 23A
FIG. 23B
FIG. 23C

ENGINEERED RENAL TISSUES, ARRAYS THEREOF, AND METHODS OF MAKING THE SAME

CROSS-REFERENCE TO RELATED APPLICATIONS

This application is a divisional of U.S. application Ser. No. 16/154,447, filed Oct. 8, 2018, which is a continuation of U.S. patent application Ser. No. 15/259,264, filed Sep. 8, 2016, now U.S. Pat. No. 10,094,821, issued on Oct. 9, 2018, which is a continuation of U.S. patent application Ser. No. 14/876,659, filed Oct. 6, 2015, now U.S. Pat. No. 9,481,868, issued on Nov. 1, 2016, which claims the benefit of U.S. patent application Ser. No. 62/060,416, filed Oct. 6, 2014, and U.S. Patent Application No. 62/140,285, filed Mar. 30, 2015, the entire disclosures of which are hereby incorporated herein by reference.

BACKGROUND OF THE INVENTION

The full cost of bringing a new drug to market—from discovery through clinical trials to approval—is typically hundreds of millions or billions of U.S. dollars. This is in part because ninety-five percent of the experimental medicines that are studied in humans fail to be both effective and safe. Renal toxicity is a major cause of drug attrition at the clinical trial stage, and the primary site of this toxicity is within the proximal tubule.

SUMMARY OF THE INVENTION

Current in vitro renal toxicity models, such as monolayers of epithelial cells and in vivo models, such as live rodents, cannot effectively predict a drug's effects, toxicity, or metabolism in humans. For example, conventional renal cell culture models lack the complexity of native tissue and thus have a limited capacity for predicting tissue-level responses. In addition, the predictive potential of pre-clinical animal trials is limited due to species-specific differences between human and animal renal functions, including differential sensitivity to insults. What is needed is an engineered renal tissue model with native-like tissue architecture; specifically, a tissue model with cells organized spatially to recapitulate the laminar architecture of the tubulointerstitial tissue interface. Such an engineered renal tissue model would be more predictive of human in vivo response and would be useful for modeling renal toxicity, modeling kidney disease (e.g., polycystic kidney disease, infectious disease, autoimmune disease, fibrosis, and chronic kidney disease due to high blood pressure or diabetes), and modeling transport (e.g., excretion and/or uptake of macromolecules).

The engineered tissues described herein represent a model of the tubulointerstitial interface in which human renal interstitial tissue is supporting human renal proximal tubule epithelial cells to facilitate their optimal morphology and function. Creation of a three-dimensional tubulointerstitial interface facilitates the correct localization of drug transporters and receptors required for metabolism in order to accurately study how small molecule, chemicals, contaminants, or biologics affect the renal proximal tubule. This represents a more physiologically relevant alternative to two-dimensional monolayers of human or canine kidney epithelial cells and serves as an adjunct to, or in some cases, replacement of animal studies in which species difference in renal functions hamper interpretation of results.

The engineered tissues described herein provide an opportunity to accurately study how compounds affect the renal proximal tubule as well as modeling pathogenic processes that involve tubular transport, cell-cell interactions, and the development of tubulointerstitial fibrosis such as may occur in chronic renal disease, polycystic kidney disease, or type II diabetes.

Provided herein is a three-dimensional, engineered, biological renal tubule model comprising: a layer of renal interstitial tissue, the renal interstitial tissue comprising renal fibroblasts and endothelial cells; and a layer of renal epithelial tissue, the renal epithelial tissue comprising renal tubular epithelial cells, the renal epithelial tissue in contact with the layer of renal interstitial tissue to form the three-dimensional, engineered, biological renal tubule model; provided that the interstitial tissue comprises an interstitial bio-ink, the epithelial tissue comprises an epithelial bio-ink, and form a three-dimensional, engineered, biological renal tubule model. In certain embodiments, the layer of renal interstitial tissue possesses an apical and basolateral surface. In certain embodiments, the layer of renal epithelial tissue is in contact with the apical surface of the layer of renal interstitial tissue. In certain embodiments, the layer of renal epithelial tissue consists essentially of renal tubular epithelial cells. In certain embodiments, the layer of renal epithelial tissue consists essentially of primary renal tubular epithelial cells. In certain embodiments, the primary renal tubular epithelial cells are isolated from a subject with a disease that affects kidney function. In certain embodiments, the primary renal tubular epithelial cells are isolated from a subject with a polycystic kidney disease. In certain embodiments, the primary renal tubular cells are isolated from a subject with diabetes mellitus type II. In certain embodiments, the layer of renal epithelial tissue comprises renal cell carcinoma cells. In certain embodiments, the layer of renal epithelial tissue is substantially a monolayer. In certain embodiments, the layer of renal interstitial tissue is substantially a monolayer. In certain embodiments, the layer of renal epithelial tissue is in continuous contact with the layer of renal interstitial tissue. In certain embodiments, the layer of renal epithelial tissue is in contact with and covers by 50% or more the apical surface of the layer of renal interstitial tissue. In certain embodiments, the layer of renal epithelial tissue is in contact with and covers by 70% or more the apical surface of the layer of renal interstitial tissue. In certain embodiments, the layer of renal epithelial tissue is in contact with and covers by 90% or more the apical surface of the layer of renal interstitial tissue. In certain embodiments, at least 50% of the cells in the layer of renal epithelial tissue form tight junctions with another cell of the renal epithelial tissue layer. In certain embodiments, at least 70% of the cells in the layer of renal epithelial tissue form tight junctions with another cell of the renal epithelial tissue layer. In certain embodiments, at least 90% of the cells in the layer of renal epithelial tissue form tight junctions with another cell of the renal epithelial tissue layer. In certain embodiments, the renal tubule model is between 50 and 500 μm thick. In certain embodiments, the renal tubular model is about 100 μm thick. In certain embodiments, the layer of renal epithelial tissue further comprises an extrusion compound. In certain embodiments, the fibroblasts and endothelial cells are present in the layer of renal interstitial tissue at a ratio of about 95:5 to about 5:95 fibroblasts to endothelial cells. In certain embodiments, the fibroblasts and endothelial cells are present in the layer of renal interstitial tissue at a ratio of about 75:25 to about 25:75 fibroblasts to endothelial cells. In certain embodiments, the fibroblasts and endothelial cells are present in the layer of renal interstitial tissue at a ratio of about 60:40 to about 40:60 fibroblasts to endothelial cells. In certain embodiments, the fibroblasts and endothelial cells are present in the layer of renal interstitial tissue at a ratio of about 50:50 fibroblasts to endothelial cells. In certain embodiments, the layer of renal interstitial tissue further comprises secretory cells. In certain embodiments, the layer of renal interstitial tissue further comprises immune cells. In certain embodiments, the layer of renal interstitial tissue further comprises an extrusion compound. In certain embodiments, the layer of renal interstitial tissue comprises glomerular cells. In certain embodiments, the model is substantially free of pre-formed scaffold at time of use. In certain embodiments, the renal fibroblasts, endothelial cells, and renal tubular epithelial cells are mammalian cells. In certain embodiments, any of the layer of renal interstitial tissue or layer of renal epithelial tissue is at least 30% living cells by volume. In certain embodiments, any of the layer of renal interstitial tissue or layer of renal epithelial tissue is at least 70% living cells by volume. In certain embodiments, any of the layer of renal interstitial tissue or layer of renal epithelial tissue is at least 90% living cells by volume. In certain embodiments, the renal tubule model is substantially planar. In certain embodiments, the renal tubule model is of substantially uniform thickness. In certain embodiments, the renal tubule model comprises at least one component that is bioprinted. In certain embodiments, the renal tubule model comprises at least one component that is bioprinted by extrusion. In certain embodiments, the renal tubule model further comprises a biocompatible membrane. In certain embodiments, the renal tubule model further comprises a biocompatible membrane with a pore size greater than about 0.4 In certain embodiments, the renal tubule model further comprises a biocompatible membrane with a pore size about 1 µm. In certain embodiments, a plurality of the renal tubule models are configured to form an array. In certain embodiments, a plurality of renal tubule models are configured to allow between about 20 µm and about 100 µm of space between each renal tubule model. In certain embodiments, either the interstitial or the epithelial bio-ink further comprises a therapeutic molecule or substance.

Also provided herein is a method of fabricating a three-dimensional, engineered, biological renal tubule model, the method comprising: preparing a renal interstitial bio-ink, the interstitial bio-ink comprising a plurality of interstitial cell types, the interstitial cell types comprising renal fibroblasts and endothelial cells; preparing a renal epithelial bio-ink, the epithelial bio-ink comprising renal tubular epithelial cells; depositing the renal interstitial bio-ink and the renal epithelial bio-ink such that the renal epithelial bio-ink forms a layer on at least one surface of the layer of renal interstitial bio-ink; and maturing the deposited bio-ink in a cell culture media to allow the cells to cohere to form the three-dimensional, engineered, biological renal tubule model. In certain embodiments, depositing the renal interstitial tissue bio-ink forms a renal interstitial tissue layer with an apical and basolateral surface. In certain embodiments, the renal epithelial bio-ink is deposited in contact with the apical surface of the renal interstitial tissue layer. In certain embodiments, the renal epithelial bio-ink consists essentially of renal tubular epithelial cells. In certain embodiments, the renal epithelial bio-ink consists essentially of primary renal tubular epithelial cells. In certain embodiments, the primary renal tubular epithelial cells are isolated from a subject with a disease that affects kidney function. In certain embodiments, the primary renal tubular epithelial cells are isolated from a subject with polycystic kidney disease. In certain embodiments, the primary renal tubular epithelial cells are isolated from a subject with diabetes mellitus type II. In certain embodiments, the renal epithelial bio-ink comprises renal cell carcinoma cells. In certain embodiments, the renal epithelial bio-ink is deposited in a monolayer. In certain embodiments, the renal interstitial tissue bio-ink is deposited in a monolayer. In certain embodiments, the layer of renal epithelial tissue is deposited in continuous contact with the layer of renal interstitial tissue. In certain embodiments, the renal epithelial bio-ink forms a layer that covers by 50% or more the apical surface of the layer of renal interstitial tissue. In certain embodiments, the renal epithelial bio-ink forms a layer that covers by 70% or more the apical surface of the layer of renal interstitial tissue. In certain embodiments, the renal epithelial bio-ink forms a layer that covers by 90% or more the apical surface of the layer of renal interstitial tissue. In certain embodiments, at least 50% of renal epithelial cells of the renal epithelial layer form tight junctions with other renal epithelial cells. In certain embodiments, at least 70% of renal epithelial cells of the renal epithelial layer form tight junctions with other renal epithelial cells. In certain embodiments, at least 90% of renal epithelial cells of the renal epithelial layer form tight junctions with other renal epithelial cells. In certain embodiments, the renal tubule model is between 50 and 500 µm thick. In certain embodiments, the renal tubule model is about 100 µm thick. In certain embodiments, the renal epithelial bio-ink further comprises an extrusion compound. In certain embodiments, the fibroblasts and endothelial cells are present in the renal interstitial bio-ink at a ratio of about 95:5 to about 5:95 fibroblasts to endothelial cells. In certain embodiments, the fibroblasts and endothelial cells are present in the renal interstitial bio-ink at a ratio of about 75:25 to about 25:75 fibroblasts to endothelial cells. In certain embodiments, the fibroblasts and endothelial cells are present in the renal interstitial bio-ink at a ratio of about 60:40 to about 40:60 fibroblasts to endothelial cells. In certain embodiments, the fibroblasts and endothelial cells are present in the renal interstitial bio-ink at a ratio of about 50:50 fibroblasts to endothelial cells. In certain embodiments, the renal interstitial bio-ink further comprises secretory cells. In certain embodiments, the renal interstitial bio-ink further comprises immune cells. In certain embodiments, the renal interstitial bio-ink further comprises an extrusion compound. In certain embodiments, the renal interstitial bio-ink comprises glomerular cells. In certain embodiments, the model is fabricated substantially free of pre-formed scaffold. In certain embodiments, the renal fibroblasts, endothelial cells, and renal tubular epithelial cells are mammalian cells. In certain embodiments, either of the renal interstitial bio-ink or renal epithelial bio-ink forms a planar layer after deposition. In certain embodiments, the renal tubule model is of substantially uniform thickness. In certain embodiments, the method further comprises depositing the renal interstitial bio-ink onto a biocompatible membrane. In certain embodiments, the method further comprises depositing the renal interstitial bio-ink onto a biocompatible membrane with a pore size greater than 0.4 In certain embodiments, the method further comprises depositing the renal interstitial bio-ink onto a biocompatible membrane with a pore size of about 1 µm. In certain embodiments, the method comprises three-dimensional, engineered, biological renal tubule models that are deposited to form an array. In certain embodiments, the method comprises three-dimensional, engineered, biological renal tubule models that are deposited to form an array configured to allow between about 20 µm and about 100 µm of space between each renal tubule model. In certain embodiments, the renal interstitial bio-ink is at least 30% living cells by volume. In certain embodiments, the renal interstitial bio-ink is at least 70% living cells by volume. In certain embodiments, the renal interstitial bio-ink is at least 90% living cells by volume. In certain embodiments, the renal interstitial bio-ink is deposited by extrusion bioprinting. In certain embodiments, the renal epithelial bio-ink is deposited by ink-jet bioprinting. In certain embodiments, any layer of the renal tubule model is viable in in vitro culture in culture after 3 days. In certain embodiments, any layer of the renal tubule model is viable in in vitro culture after 10 days. In certain embodiments, either the interstitial or the epithelial bio-ink further comprises a therapeutic molecule or substance.

Also provided herein is a method of assessing the renal toxicity of a therapeutic agent, the method comprising: preparing a renal interstitial bio-ink, the interstitial bio-ink comprising a plurality of interstitial cell types, the interstitial cell types comprising renal fibroblasts and endothelial cells; preparing a renal epithelial bio-ink, the epithelial bio-ink comprising renal tubular epithelial cells; depositing the interstitial bio-ink and the epithelial bio-ink such that the epithelial bio-ink forms a layer on at least one surface of the interstitial bio-ink; and maturing the deposited bio-ink in a cell culture media to allow the cells to cohere to form a three-dimensional, engineered, biological renal tubule model; contacting a therapeutic agent with the construct; measuring viability or functionality of the renal tubular epithelial cells; and assessing the renal toxicity of the therapeutic agent based on the measured viability or functionality of the renal tubular epithelial cells. In certain embodiments, the interstitial bio-ink is deposited by extrusion bioprinting. In certain embodiments, the epithelial bio-ink is deposited by ink-jet bioprinting. In certain embodiments, either the interstitial or the epithelial bio-ink further comprises a therapeutic molecule or substance.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 2A and 2B show a non-limiting example of a schematic structure diagram; in this case, a schematic structure diagram depicting the architecture of Structure 1 of Example 1 (FIG. 2A); and a non-limiting example of a bioprinted renal tubule model 48 hours after the tissue has fused (FIG. 2B).

FIG. 3B: 200× total magnification).

FIG. 13 shows sustained viability of 3D renal tubule models in culture in comparison to 2D coculture.

FIG. 14A shows a ratio of 90:10 fibroblasts to endothelial cells. FIG. 14B shows a ratio of 75:25 fibroblasts to endothelial cells. FIG. 14C shows a ratio of 50:50 fibroblasts to endothelial cells.

FIG. 15A shows a ratio of 90:10 fibroblasts to endothelial cells. FIG. 15B shows a ratio of 75:25 fibroblasts to endothelial cells. FIG. 15C shows a ratio of 50:50 fibroblasts to endothelial cells.

FIG. 16A shows a macroscopic view of a bioprinted renal tubule model. FIG. 16B shows Keyence surface mapping data.

FIG. 17A shows epithelial cells at a concentration of $1.25 \times 10^5$ cells/well in serum free media. FIG. 17B shows epithelial cells at a concentration of $1.25 \times 10^5$ cells/well in 2% serum. FIG. 17C shows epithelial cells at a concentration of $2.5 \times 10^5$ cells/well in 2% serum. FIG. 17D shows epithelial cells at a concentration of $5.0 \times 10^5$ cells/well in 2% serum.

FIG. 19A shows a lactate dehydrogenase (LDH) release assay. FIG. 19B shows γ-glutamyl-transferase (GGT) activity.

FIGS. 21A, 21B, and 21C show examples of cisplatin toxicity tests using a 3D renal tubule model. FIG. 21A shows alamarBlue assay for viability. FIG. 21B shows γ-glutamyl-transferase (GGT) activity. FIG. 21C shows a lactate dehydrogenase (LDH) release assay.

FIGS. 23A, 23B, and 23C show examples of cisplatin toxicity tests using a 3D renal tubule model comparing primary and immortalized endothelial cells. FIG. 23A shows alamarBlue assay for viability. FIG. 23B shows γ-glutamyl-transferase (GGT) activity. FIG. 23C shows a lactate dehydrogenase (LDH) release assay.

FIG. 24A shows interstitial tissue printed on a pore size of 0.4 μm. FIG. 24B shows interstitial tissue printed on a pore size of 1.0 μm.

FIG. 25A shows renal tubule models after 6 days in culture. FIG. 25B shows renal tubule models after 10 days in culture. FIG. 25C 24B shows renal tubule models after 27 days in culture.

DETAILED DESCRIPTION OF THE INVENTION

Figure 1:
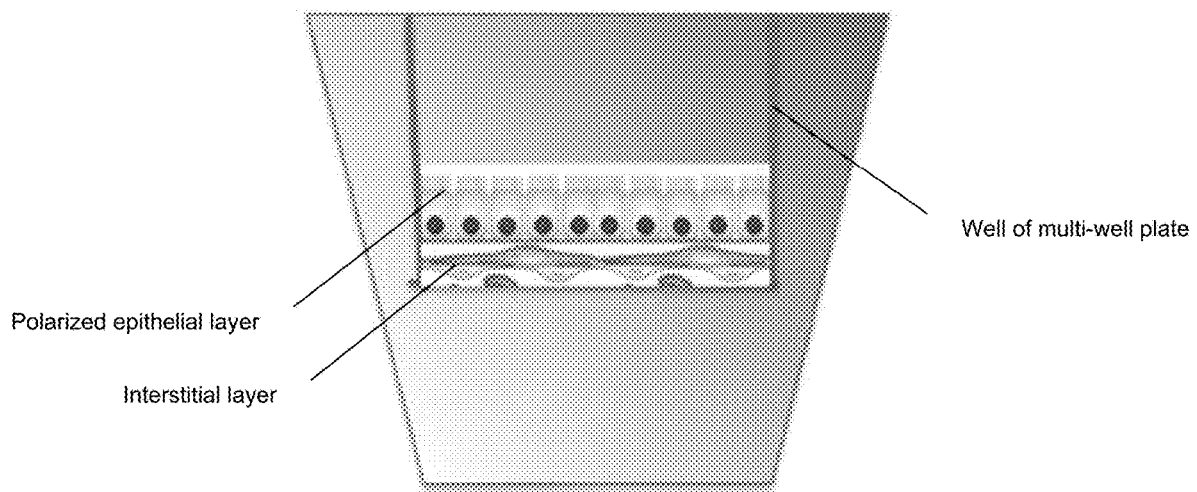
FIG. 1 shows a non-limiting example of a schematic concept diagram; in this case, a schematic concept diagram depicting an interstitial layer topped with a polarized epithelial monolayer.

Provided herein is a three-dimensional, engineered, biological renal tubule model comprising: a layer of renal interstitial tissue, the renal interstitial tissue comprising renal fibroblasts and endothelial cells; and a layer of renal epithelial tissue, the renal epithelial tissue comprising renal tubular epithelial cells, the renal epithelial tissue in contact with the layer of renal interstitial tissue to form the three-dimensional, engineered, biological renal tubule model; provided that the interstitial tissue comprises an interstitial bio-ink, the epithelial tissue comprises an epithelial bio-ink, and form a three-dimensional, engineered, biological renal tubule model.

Also provided herein is a method of fabricating a three-dimensional, engineered, biological renal tubule model, the method comprising: preparing a renal interstitial bio-ink, the interstitial bio-ink comprising a plurality of interstitial cell types, the interstitial cell types comprising renal fibroblasts and endothelial cells; preparing a renal epithelial bio-ink, the epithelial bio-ink comprising renal tubular epithelial cells; depositing the renal interstitial bio-ink and the renal epithelial bio-ink such that the renal epithelial bio-ink forms a layer on at least one surface of the layer of renal interstitial bio-ink; and maturing the deposited bio-ink in a cell culture media to allow the cells to cohere to form the three-dimensional, engineered, biological renal tubule model.

Also provided herein is a method of assessing the renal toxicity of a therapeutic agent, the method comprising: preparing a renal interstitial bio-ink, the interstitial bio-ink comprising a plurality of interstitial cell types, the interstitial cell types comprising renal fibroblasts and endothelial cells; preparing a renal epithelial bio-ink, the epithelial bio-ink comprising renal tubular epithelial cells; depositing the interstitial bio-ink and the epithelial bio-ink such that the epithelial bio-ink forms a layer on at least one surface of the interstitial bio-ink; and maturing the deposited bio-ink in a cell culture media to allow the cells to cohere to form a three-dimensional, engineered, biological renal tubule model; contacting a therapeutic agent with the construct; measuring viability or functionality of the renal tubular epithelial cells; and assessing the renal toxicity of the therapeutic agent based on the measured viability or functionality of the renal tubular epithelial cells.

Certain Definitions

Unless otherwise defined, all technical terms used herein have the same meaning as commonly understood by one of ordinary skill in the art to which this invention belongs. As used in this specification and the appended claims, the singular forms "a," "an," and "the" include plural references unless the context clearly dictates otherwise. Any reference to "or" herein is intended to encompass "and/or" unless otherwise stated.

As used herein, "array" means a scientific tool including an association of multiple elements spatially arranged to allow a plurality of tests to be performed on a sample, one or more tests to be performed on a plurality of samples, or both.

As used herein, "assay" means a procedure for testing or measuring the presence or activity of a substance (e.g., a chemical, molecule, biochemical, protein, hormone, or drug, etc.) in an organic or biologic sample (e.g., cell aggregate, tissue, organ, organism, etc.).

As used herein, "layer" means an association of cells in X and Y planes that is one or multiple cells thick. In some embodiments, the renal tubules describe herein include one layer. In other embodiments, the renal tubules describe herein include a plurality of layers. In various embodiments, a layer forms a contiguous, substantially contiguous, or non-contiguous sheet of cells. In some embodiments, each layer of renal tubule described herein comprises multiple cells in the X, Y, and Z axes.

As used herein, "tissue" means an aggregate of cells.

As used herein, "bio-ink" means a liquid, semi-solid, or solid composition for use in bioprinting. In some embodiments, bio-ink comprises cell solutions, cell aggregates, cell-comprising gels, multicellular bodies, or tissues. In some embodiments, the bio-ink additionally comprises non-cellular materials that provide specific biomechanical properties that enable bioprinting. In some embodiments, the bio-ink comprises an extrusion compound. In some cases, the extrusion compound is engineered to be removed after the bioprinting process. In other embodiments, at least some portion of the extrusion compound remains entrained with the cells post-printing and is not removed. An interstitial bio-ink comprises at least one cell of interstitial origin such as a fibroblast, mesenchymal cell, or pluripotent cells induced to have interstitial characteristics. An epithelial bio-ink comprises at least one epithelial cell type including cells of the proximal tubule.

As used herein, "bioprinting" means utilizing three-dimensional, precise deposition of cells (e.g., cell solutions, cell-containing gels, cell suspensions, cell concentrations, multicellular aggregates, multicellular bodies, etc.) via methodology that is compatible with an automated or semi-automated, computer-aided, three-dimensional prototyping device (e.g., a bioprinter). Suitable bioprinters include the Novogen Bioprinter from Organovo, Inc. (San Diego, Calif.).

As used herein, "scaffold" refers to synthetic scaffolds such as polymer scaffolds and porous hydrogels, non-synthetic scaffolds such as pre-formed extracellular matrix layers, dead cell layers, and decellularized tissues, and any other type of pre-formed scaffold that is integral to the physical structure of the engineered tissue and not able to be removed from the tissue without damage/destruction of said tissue. In further embodiments, decellularized tissue scaffolds include decellularized native tissues or decellularized cellular material generated by cultured cells in any manner; for example, cell layers that are allowed to die or are decellularized, leaving behind the ECM they produced while living. The term "scaffoldless," therefore, is intended to imply that pre-formed scaffold is not an integral part of the engineered tissue at the time of use, either having been removed or remaining as an inert component of the engineered tissue. "Scaffoldless" is used interchangeably with "scaffold-free" and "free of pre-formed scaffold."

As used herein a "subject" is an organism of any mammalian species including but not limited to humans, primates, apes, monkey, dogs, cats, mice, rats, rabbits, pigs, horses and others. A subject can be any mammalian species alive or dead. Subject includes recently deceased subjects or biopsy samples taken from a living subject.

As used herein "therapeutic substance" means any molecule, biologic, compound or composition that is approved to treat a disease, under investigation to treat a disease, or that elicits a biological response such as changes in DNA, RNA, peptide, polypeptide or protein.

As used herein "viability" means that at least 50%, 60%, 70%, 80%, 90%, 95%, 97% or more of cells in a bio-ink or tissue layer are live as determined by at least one test of viability. Tests for viability are known in the art, and include, but are not limited to vital dyes, staining for apoptotic markers, TUNEL staining, DNA fragmentation analysis, AlamarBlue staining, functional determinations and the like.

Composition of the Renal Tubule Model

In some embodiments, the cells within the tissues are organized spatially to recapitulate the laminar architecture of the tubule-interstitial tissue interface; a polarized tubular epithelium is present on top of a layer of renal interstitial tissue that includes an endothelial cell-based microvascular network. Specialized cells, such as EPO-producing cells, are optionally included within the peritubular spaces. In some embodiments, the epithelium possesses or generates brush borders.

In particular, non-limiting embodiments, the engineered renal tissues described herein comprise two major parts: 1) an interstitial layer composed of adult renal fibroblasts and human umbilical vein endothelial cells (HUVEC); and 2) a polarized epithelial monolayer composed of either normal human renal proximal tubule epithelial cells (RPTEC), Madin-Darby canine kidney cells (MDCK), rat primary RPTEC cells, and/or immortalized RPTEC cells, wherein immortalization is optionally achieved through genetic manipulation of hTERT to form hTERT-immortalized RPTEC cells. The cells are deposited using the Novogen MMX Bioprinter in such a way that the epithelial layer is apical to the interstitial layer (see FIG. 1). Structures are created by spatially-controlled deposition of cells mixed with a thermo-responsive hydrogel that degrades over time (Novogel® 2.0) combined with deposition of aerosolized cellular materials by compressed gas propulsion (inkjet spray).

Referring to FIG. 1, in a particular embodiment, a three-dimensional, engineered renal tubule model comprises an interstitial layer and an epithelial layer. In this embodiment, the two layers together model the wall of a renal distal tubule. This configuration is critical for modeling in vivo tissues and predicting native tissue responses. Response of the epithelial layer is predictive of native tissue response to drugs, chemicals, or biological agents, and may provide information relative to toxicity or efficacy. The interstitial layer is critical for proper functioning of the epithelium and serves as a model for native tissue fibrosis, in particular renal tubulointerstitial fibrosis.

Referring to FIG. 2A, in a particular embodiment, an interstitial layer is bioprinted, using continuous deposition techniques. In this embodiment, a sheet of interstitium is bioprinted followed by a border of interstitium to form a three sided container. A layer of epithelium is then bioprinted, again using continuous deposition techniques, into the container of interstitium. This embodiment provides the necessary contact between the interstitial and epithelial layers. FIG. 2B, depicts an actual bioprinted renal tubule model, shown 48 hours after the tissue has coalesced. In some embodiments, the tissue coalesces within 4, 6, 8, 12 or 24 hours.

Figure 6A:
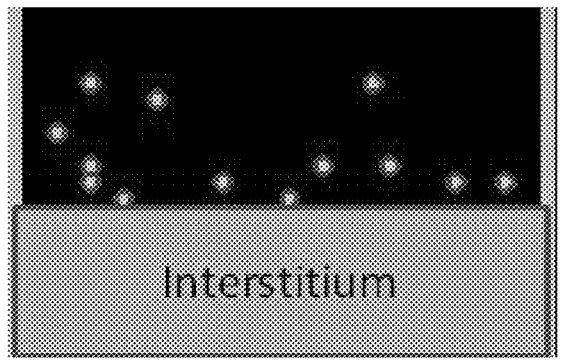
FIGS. 6A and 6B show a non-limiting example of a schematic structure diagram; in this case, a schematic structure diagram depicting the architecture of Structure 2 of Example 2.
Figure 6B:
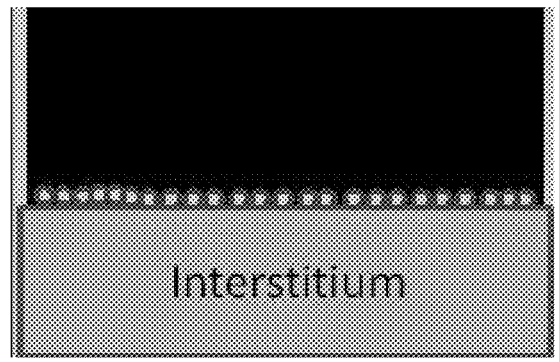

Referring to FIGS. 6A and 6B, in a particular embodiment, an interstitial layer is bioprinted, using continuous deposition techniques. In this embodiment, an epithelial layer is bioprinted, using ink-jet deposition techniques onto the interstitial layer. A substantially contiguous layer of epithelium is consistent with in vivo tissues and is critical to replicate a physiologically relevant architecture. Ink-jet deposition techniques provide the ability to deposit one or more thin layers of epithelial cells onto the potentially irregular surface of the interstitial layer. In such embodiments, ink-jet deposition of the epithelial layer is optionally performed immediately after bioprinting of the interstitial layer or after the interstitial layer has been allowed to mature.

In some embodiments, the cells are bioprinted. In further embodiments, the bioprinted cells are cohered to form the engineered renal tubule models. In still further embodiments, the engineered renal tubule models are free or substantially free of pre-formed scaffold at the time of fabrication or the time of use. In some cases, bioprinting allows fabrication of tissues that mimic the appropriate cellularity of native tissue.

In some embodiments, the three-dimensional, engineered renal tubule models described herein are distinguished from tissues fabricated by prior technologies by virtue of the fact that they are three-dimensional, free of pre-formed scaffolds, consist essentially of cells, and/or have a high cell density (e.g., greater than 30% cellular, greater than 40% cellular, greater than 50% cellular, greater than 60% cellular, greater than 70% cellular, greater than 80% cellular, greater than 90% cellular, or greater than 95% cellular).

In some embodiments, the three-dimensional, engineered renal tubule models described herein are distinguished from native (e.g., non-engineered) tissues by virtue of the fact that they are non-innervated (e.g., substantially free of nervous tissue), substantially free of mature vasculature, and/or substantially free of blood components. For example, in various embodiments, the three-dimensional, engineered renal tubule models are free of plasma, red blood cells, platelets, and the like and/or endogenously-generated plasma, red blood cells, platelets, and the like. In certain embodiments, the engineered renal tubule model lacks immune cells such as T cell, B cells, macrophages, dendritic cells, basophils, mast cells or eosinophils. In some embodiments, the model is not tubular in shape like a naturally occurring renal proximal tubule, but is planar or sheet-like, this advantageously allows for in vitro assays and analysis. In some embodiments, the fibroblasts are not of renal origin. In some embodiments, the endothelial cells are not of renal origin. In some embodiments, the epithelial cells are not of human origin. In certain embodiments, the engineered renal tubule model lacks undifferentiated cells. In certain embodiments, the engineered renal tubule model lacks undifferentiated renal cells. In some embodiments, the three-dimensional, engineered renal tubule models described herein are distinguished from native renal tubule tissues in that they are flat or substantially planar. In certain embodiments, the three-dimensional, engineered renal tubule models described herein possess functional improvements over native renal tubule tissues; one example is high viability after a sustained amount of time in culture up to at least 7, 10 or 27 days in culture. In some embodiments, the cells used in the renal tubule model are transformed or immortalized. In some embodiments, the cells used in the renal tubule model are transgenic and contain protein fusions with fluorescent proteins, like EGFP, GFP, RFP, YFP, or CFP. In some embodiments, the cells used in the renal tubule model are transgenic and contain reporter constructs with fluorescent proteins; like EGFP, GFP, RFP, YFP, GFP; or luminescent proteins like firefly or renilla luciferase. In certain embodiments, any of the cells contain a deletion or insertion of 1, 2, 3, 4, 5, 6, 7, 8, 9, 10 genes or more. In some embodiments, the 3D renal tubule models are chimeras, wherein at least one cell is form a different mammalian species than any other cell of the 3D renal tubule model. In some embodiments, the 3D renal tubule models are chimeras, wherein at least one cell is form a different human donor than any other cell of the 3D renal tubule model.

Cellular Inputs

In some embodiments, the engineered tissues, arrays, and methods described herein include a plurality of cell types. In some embodiments, the renal tubule models comprise a layer of interstitial tissue comprising mammalian fibroblasts and mammalian endothelial cells. In various embodiments, suitable endothelial cells are derived from human umbilical vein (HUVEC), human primary, human kidney, or from directed differentiation of induced pluripotent stem cells (iPS) or human embryonic stem cells (hES). In some embodiments, the fibroblasts are renal interstitial fibroblasts. In various embodiments, suitable renal interstitial fibroblasts are derived from primary cells isolated from human kidney. In some embodiments, the fibroblasts are dermal or vascular in origin. In some embodiments, one or more of the cellular components are derived from a non-human mammal. In some embodiments, the interstitial tissue comprises tumor cells or cancer cells. In some embodiments, the layer of interstitial tissue is substantially a monolayer. In some embodiments, the layer of interstitial tissue comprises a monolayer over 95% of its surface area. In some embodiments, the layer of interstitial tissue comprises a monolayer over 90% of its surface area. In some embodiments, the layer of interstitial tissue comprises a monolayer over 80% of its surface area. In some embodiments, the layer of interstitial tissue is greater than 1 cell thick. In some embodiments, the layer of interstitial tissue is greater than 2 cells thick. In some embodiments, the layer of interstitial tissue is greater than 3 cells thick. In some embodiments, the layer of interstitial tissue is greater than 4 cells thick. In some embodiments, the layer of interstitial tissue is greater than 5 cells thick. In some embodiments, the layer of interstitial tissue is greater than 10 cells thick. In some embodiments, the layer of interstitial tissue is greater than 20 cells thick. In some embodiments, the layer of interstitial tissue is greater than 50 cells thick. In some embodiments, the layer of interstitial tissue is greater than 100 cells thick. In some embodiments, the layer of interstitial tissue is greater than 20 µm thick. In some embodiments, the layer of interstitial tissue is greater than 30 µm thick. In some embodiments, the layer of interstitial tissue is greater than 40 µm thick. In some embodiments, the layer of interstitial tissue is greater than 50 µm thick. In some embodiments, the layer of interstitial tissue is greater than 100 µm thick. In some embodiments, the layer of interstitial tissue is greater than 200 µm thick. In some embodiments, the layer of interstitial tissue is greater than 500 µm thick. In some embodiments, the layer of interstitial tissue is greater than 600 µm thick. In some embodiments, the layer of interstitial tissue is greater than 1000 µm thick. In some embodiments, the layer of interstitial tissue is less than 20 µm thick. In some embodiments, the layer of interstitial tissue is less than 30 µm thick. In some embodiments, the layer of interstitial tissue is less than 40 µm thick. In some embodiments, the layer of interstitial tissue is less than 50 µm thick. In some embodiments, the layer of interstitial tissue is less than 100 µm thick. In some embodiments, the layer of interstitial tissue is less than 200 µm thick. In some embodiments, the layer of interstitial tissue is less than 500 µm thick. In some embodiments, the layer of interstitial tissue is less than 600 µm thick. In some embodiments, the layer of interstitial tissue is less than 1000 µm thick.

In some embodiments, the renal tubule models comprise a layer of epithelial tissue comprising mammalian epithelial cells. In further embodiments, the epithelial cells are renal tubular epithelial cells (e.g., proximal tubule epithelial cells). In still further embodiments, suitable renal tubular epithelial cells are primary isolates or cells derived from the directed differentiation of stem cells (induced pluripotent stem cell (iPS)-derived and/or human embryonic stem cell (hES)-derived). In some embodiments, the renal tubular epithelial cells are Madin-Darby canine kidney (MDCK) cells. In some embodiments, the renal tubular epithelial cells are immortalized human cells. In other embodiments, the renal tubular epithelial cells are immortalized cells such as hTERT-RPTEC cells, HK-2 cells, LLC-PK1 cells, or OK cells. In some embodiments, the epithelial cells are derived from a non-human mammal such as, for example, rat, mouse, pig, or primate. In some embodiments, the layer of epithelial tissue consists essentially of renal tubule epithelial cells. In some embodiments, the layer of epithelial tissue consists essentially of primary renal tubule epithelial cells. In some embodiments, the layer of epithelial tissue consists essentially of renal proximal tubule epithelial cells. In some embodiments, the layer of epithelial tissue consists essentially of primary renal proximal tubule epithelial cells. In some embodiments, the layer of epithelial tissue is substantially a monolayer. In some embodiments, the layer of epithelial tissue comprises tumor cells. In some embodiments, the layer of epithelial tissue comprises renal cell carcinoma cells. In some embodiments, the layer of epithelial tissue comprises a monolayer over 95% of its surface area. In some embodiments, the layer of epithelial tissue comprises a monolayer over 90% of its surface area. In some embodiments, the layer of epithelial tissue comprises a monolayer over 80% of its surface area. In some embodiments, the layer of epithelial tissue is greater than 1 cell thick. In some embodiments, the layer of epithelial tissue is greater than 2 cells thick. In some embodiments, the layer of epithelial tissue is greater than 3 cells thick. In some embodiments, the layer of epithelial tissue is greater than 4 cells thick. In some embodiments, the layer of epithelial tissue is greater than 5 cells thick. In some embodiments, the layer of epithelial tissue is greater than 10 cells thick. In some embodiments, the layer of epithelial tissue is greater than 20 cells thick. In some embodiments, the layer of epithelial tissue is greater than 50 cells thick. In some embodiments, the layer of epithelial tissue is greater than 100 cells thick. In some embodiments, the layer of epithelial tissue is greater than 20 µm thick. In some embodiments, the layer of epithelial tissue is greater than 30 µm thick. In some embodiments, the layer of epithelial tissue is greater than 40 µm thick. In some embodiments, the layer of epithelial tissue is greater than 50 µm thick. In some embodiments, the layer of epithelial tissue is greater than 100 µm thick. In some embodiments, the layer of epithelial tissue is greater than 200 µm thick. In some embodiments, the layer of epithelial tissue is greater than 500 µm thick. In some embodiments, the layer of interstitial tissue is greater than 600 µm thick. In some embodiments, the layer of epithelial tissue is greater than 1000 µm thick. In some embodiments, the layer of epithelial tissue is less than 1000 µm thick. In some embodiments, the layer of interstitial tissue is less than 600 µm thick. In some embodiments, the layer of epithelial tissue is less than 500 µm thick. In some embodiments, the layer of epithelial tissue is less than 200 µm thick. In some embodiments, the layer of epithelial tissue is less than 100 µm thick. In some embodiments, the layer of epithelial tissue is less than 50 µm thick. In some embodiments, the layer of epithelial tissue is less than 40 µm thick. In some embodiments, the layer of epithelial tissue is less than 30 µm thick. In some embodiments, the layer of epithelial tissue is less than 20 µm thick.

Optionally, the renal tubule models comprise other cell types (e.g., EPO-producing cells, immune cells, etc.). In some embodiments, the immune cells are T cells. In some embodiments, the immune cells are B cells. In some embodiments, the immune cells are NK cells. In some embodiments, the immune cells are dendritic cells. In some embodiments, the immune cells are macrophage cells.

A wide range of cell ratios are suitable. In some embodiments, the epithelial layer comprises, consists of, or consists essentially of proximal tubule epithelial cells. In some embodiments, the interstitial layer comprises, consists of, or consists essentially of fibroblasts and endothelial cells in specific ratios. Suitable proportions of fibroblasts include, by way of non-limiting examples, about 5, 10, 15, 20, 25, 30, 35, 40, 45, 50, 55, 60, 65, 70, 75, 80, 85, 90, and 95% fibroblasts, including increments therein. Suitable proportions of endothelial cells include, by way of non-limiting examples, about 5, 10, 15, 20, 25, 30, 35, 40, 45, 50, 55, 60, 65, 70, 75, 80, 85, 90, and 95% endothelial cells, including increments therein. In certain embodiments, the interstitial layer comprises, consists essentially of, or consists of a specified ratio of fibroblast to endothelial cells. In certain embodiments, the ratio of fibroblast to endothelial cells is at least 5:95, 10:90, 15:85, 20:80, 25:75, 30:70, 35:65, 40:60, 45:65, 50:50, 55:45, 60:40, 65:35, 70:30, 75:25, 80:20, 85:15, 90:10 or 95:5, including increments therein. In certain embodiments, the ratio of fibroblast to endothelial cells is no more than 5:95, 10:90, 15:85, 20:80, 25:75, 30:70, 35:65, 40:60, 45:65, 50:50, 55:45, 60:40, 65:35, 70:30, 75:25, 80:20, 85:15, 90:10 or 95:5, including increments therein. In certain embodiments, the ratio of fibroblast to endothelial cells is about 50:50. In certain embodiments, the ratio of fibroblast to endothelial cells is from about 60:40 to about 40:60.

A wide range of cell concentrations are suitable for bio-inks. Bio-inks are suitably prepared for continuous deposition bioprinting techniques with concentrations of cells including, by way of non-limiting examples, about 1, 2, 3, 4, 5, 6, 7, 8, 9, 10, 20, 30, 40, 50, 60, 70, 80, 90, 100, 110, 120, 130, 140, 150, 160, 170, 180, 190, 200, 225, 250, 275, 300, or more, million cells per milliliter of bio-ink. In a particular embodiment, bio-ink prepared for continuous deposition bioprinting comprises about 100-200 million cells/mL. Bio-inks are suitably prepared for ink-jet deposition bioprinting techniques with concentrations of cells including, by way of non-limiting examples, about 0.25, 0.5, 1, 2, 3, 5, 10, 15 or more, million cells per milliliter of bio-ink. In a particular embodiment, bio-ink prepared for ink-jet deposition bioprinting comprises about 1-5 million cells/mL. In a particular embodiment, bio-ink prepared for ink-jet deposition bioprinting comprises about 1-4 million cells/mL. In a particular embodiment, bio-ink prepared for ink-jet deposition bioprinting comprises about 1-3 million cells/mL. In a particular embodiment, bio-ink prepared for ink-jet deposition bioprinting comprises about 1-2 million cells/mL.

In certain embodiments, the renal interstitial bio-ink comprises between 50 million and 1 billion cells per milliliter. In certain embodiments, the renal interstitial bio-ink comprises between 50 million and 900 million cells per milliliter. In certain embodiments, the renal interstitial bio-ink comprises between 50 million and 800 million cells per milliliter. In certain embodiments, the renal interstitial bio ink comprises between 50 million and 700 million cells per milliliter. In certain embodiments, the renal interstitial bio ink comprises between 50 million and 600 million cells per milliliter. In certain embodiments, the renal interstitial bio ink comprises between 50 million and 500 million cells per milliliter. In certain embodiments, the renal interstitial bio ink comprises between 50 million and 400 million cells per milliliter. In certain embodiments, the renal interstitial bio ink comprises between 50 million and 300 million cells per milliliter. In certain embodiments, the renal interstitial bio ink comprises between 50 million and 200 million cells per milliliter. In certain embodiments, the renal interstitial bio-ink comprises between 75 million and 600 million cells per milliliter. In certain embodiments, the renal interstitial bio-ink comprises between 100 million and 600 million cells per milliliter. In certain embodiments, the renal interstitial bio ink comprises between 100 million and 500 million cells per milliliter. In certain embodiments, the renal interstitial bio ink comprises between 100 million and 400 million cells per milliliter. In certain embodiments, the renal interstitial bio-ink comprises between 100 million and 300 million cells per milliliter. In certain embodiments, the renal interstitial bio-ink comprises between 100 million and 200 million cells per milliliter. In certain embodiments, the renal interstitial bio-ink comprises between 100 million and 150 million cells per milliliter.

In certain embodiments, the renal epithelial bio-ink comprises between. 0.25 million and 5 million cells per milliliter. In certain embodiments, the renal epithelial bio-ink comprises between. 0.25 million and 4 million cells per milliliter. In certain embodiments, the renal epithelial bio-ink comprises between. 0.25 million and 3 million cells per milliliter. In certain embodiments, the renal epithelial bio-ink comprises between. 0.25 million and 2 million cells per milliliter. In certain embodiments, the renal epithelial bio-ink comprises between. 0.25 million and 1 million cells per milliliter.

In certain embodiments, the renal epithelial bio-ink comprises between. 0.5 million and 5 million cells per milliliter. In certain embodiments, the renal epithelial bio-ink comprises between. 0.5 million and 4 million cells per milliliter. In certain embodiments, the renal epithelial bio-ink comprises between. 0.5 million and 3 million cells per milliliter. In certain embodiments, the renal epithelial bio-ink comprises between. 0.5 million and 2 million cells per milliliter. In certain embodiments, the renal epithelial bio-ink comprises between. 0.5 million and 1 million cells per milliliter. In certain embodiments, the renal epithelial bio-ink comprises between 1 million and 5 million cells per milliliter. In certain embodiments, the renal epithelial bio-ink comprises between 1 million and 4 million cells per milliliter. In certain embodiments, the renal epithelial bio-ink comprises between 1 million and 3 million cells per milliliter. In certain embodiments, the renal epithelial bio-ink comprises between 1 million and 2 million cells per milliliter.

In certain embodiments, the density of the epithelial bio-ink is less than the density of the interstitial bio-ink. In certain embodiments, the ratio of the density of the interstitial bio-ink to the density of the epithelial bio-ink is about 300:1; about 275:1; about 250:1; about 225:1; about 200:1; about 175:1, about 150:1, about 125:1; about 100:1, about 75:1 or about 50:1. In certain embodiments, the ratio of the density of the interstitial bio-ink to the density of the epithelial bio-ink ranges from about 300:1 to about 50:1. In certain embodiments, the ratio of the density of the interstitial bio-ink to the density of the epithelial bio-ink ranges from about 250:1 to about 75:1. In certain embodiments, the ratio of the density of the interstitial bio-ink to the density of the epithelial bio-ink ranges from about 200:1 to about 75:1. In certain embodiments, the ratio of the density of the interstitial bio-ink to the density of the epithelial bio-ink ranges from about 150:1 to about 75:1. In certain embodiments, the ratio of the density of the interstitial bio-ink to the density of the epithelial bio-ink ranges from about 125:1 to about 75:1.

In certain embodiments, the bio-ink is a viscous liquid. In certain embodiments, the bio-ink is a semi-solid. In certain embodiments, the bio-ink is a solid. In certain embodiments, the viscosity of the bio-ink is greater than 100 centipoise. In certain embodiments, the viscosity of the bio-ink is greater than 200 centipoise. In certain embodiments, the viscosity of the bio-ink is greater than 500 centipoise. In certain embodiments, the viscosity of the bio-ink is greater than 1,000 centipoise. In certain embodiments, the viscosity of the bio-ink is greater than 2,000 centipoise. In certain embodiments, the viscosity of the bio-ink is greater than 5,000 centipoise. In certain embodiments, the viscosity of the bio-ink is greater than 10,000 centipoise. In certain embodiments, the viscosity of the bio-ink is greater than 20,000 centipoise. In certain embodiments, the viscosity of the bio-ink is greater than 50,000 centipoise. In certain embodiments, the viscosity of the bio-ink is greater than 100,000 centipoise. In certain embodiments, the viscosity of the bio-ink is less than 100 centipoise. In certain embodiments, the viscosity of the bio-ink is less than 200 centipoise. In certain embodiments, the viscosity of the bio-ink is less than 500 centipoise. In certain embodiments, the viscosity of the bio-ink is less than 1,000 centipoise. In certain embodiments, the viscosity of the bio-ink is less than 2,000 centipoise. In certain embodiments, the viscosity of the bio-ink is less than 5,000 centipoise. In certain embodiments, the viscosity of the bio-ink is less than 10,000 centipoise. In certain embodiments, the viscosity of the bio-ink is less than 20,000 centipoise. In certain embodiments, the viscosity of the bio-ink is less than 50,000 centipoise. In certain embodiments, the viscosity of the bio-ink is less than 100,000 centipoise.

In some embodiments, the mean thickness of the renal tubule model is at least 50 µm. In some embodiments, the mean thickness of the renal tubule model is at least 100 µm. In some embodiments, the mean thickness of the renal tubule model is at least 200 µm. In some embodiments, the mean thickness of the renal tubule model is at least 300 µm. In some embodiments, the mean thickness of the renal tubule model is at least 400 µm. In some embodiments, the mean thickness of the renal tubule model is at least 500 µm. In some embodiments, the mean thickness of the renal tubule model is at least 600 µm. In some embodiments, the mean thickness of the renal tubule model is at least 700 µm. In some embodiments, the mean thickness of the renal tubule model is at least 800 µm. In some embodiments, the mean thickness of the renal tubule model is at least 900 µm. In some embodiments, the mean thickness of the renal tubule model is at least 1000 µm. In some embodiments, the mean thickness of the renal tubule model is between 50 µm and 1000 µm. In some embodiments, the mean thickness of the renal tubule model is between 75 µm and 1000 µm. In some embodiments, the mean thickness of the renal tubule model is between 100 µm and 1000 µm. In some embodiments, the mean thickness of the renal tubule model is between 200 µm and 1000 µm. In some embodiments, the mean thickness of the renal tubule model is between 500 µm and 1000 µm. In some embodiments, the mean thickness of the renal tubule model is between 50 µm and 500 µm. In some embodiments, the mean thickness of the renal tubule model is between 50 µm and 300 µm. In some embodiments, the mean thickness of the renal tubule model is between 50 µm and 200 µm. In some embodiments, the mean thickness of the renal tubule model is between 50 µm and 150 µm. In some embodiments, the mean thickness of the renal tubule model is between 50 µm and 125 µm. In some embodiments, the mean thickness of the renal tubule model is between 75 µm and 100 µm.

In some embodiments, the surface area of the renal tubule model is at least 0.01 cm$^2$. In some embodiments, the surface area of the renal tubule model is at least 0.02 cm$^2$. In some embodiments, the surface area of the renal tubule model is at least 0.03 cm$^2$. In some embodiments, the surface area of the renal tubule model is at least 0.04 cm$^2$. In some embodiments, the surface area of the renal tubule model is at least 0.05 cm$^2$. In some embodiments, the surface area of the renal tubule model is at least 0.06 cm$^2$. In some embodiments, the surface area of the renal tubule model is at least 0.07 cm$^2$. In some embodiments, the surface area of the renal tubule model is at least 0.08 cm$^2$. In some embodiments, the surface area of the renal tubule model is at least 0.09 cm$^2$. In some embodiments, the surface area of the renal tubule model is at least 0.10 cm$^2$. In some embodiments, the surface area of the renal tubule model is at least 0.11 cm$^2$. In some embodiments, the surface area of the renal tubule model is at least 0.12 cm$^2$. In some embodiments, the surface area of the renal tubule model is less than 0.5 cm$^2$. In some embodiments, the surface area of the renal tubule model is less than 0.4 cm$^2$. In some embodiments, the surface area of the renal tubule model is less than 0.3 cm$^2$. In some embodiments, the surface area of the renal tubule model is less than 0.2 cm$^2$. In some embodiments, the surface area of the renal tubule model is less than 0.1 cm$^2$.

Architectural Features of the Renal Tubule Model

The renal tubule models of the present disclosure can be architecturally arranged in many configurations. In certain embodiments, the epithelial tissue and interstitial tissue layers are separate architecturally distinct layers that are in direct contact or separated by 1, 2, 3, 4, 5, 6, 7, 8, 9, 10, 15, 20 μm or more, including increments therein. In certain embodiments, the separation is due to the secretion and deposition of extracellular matrix between the two layers, which for the purposes of this disclosure is considered contact. In normal physiological tissue cells and cell layers are polarized to have an apical (lumen facing) surface and a basolateral surface, which faces other cells or tissue matrix. For the purposes of the renal tubule models disclosed herein the basolateral surface refers to a surface that faces another cell, an extracellular matrix or the surface of a biocompatible membrane or culture vessel. For the purposes of the renal tubule models disclosed herein the apical surface refers to a surface that faces away from the surface of a biocompatible membrane or culture vessel. In certain embodiments, the basolateral surface of the interstitial tissue layer is the surface attached to a biocompatible membrane or culture vessel; and the apical surface of the interstitial tissue layer is the surface not attached to a biocompatible membrane or culture vessel. In certain embodiments, the epithelial tissue layer is deposited onto and forms a layer on the apical surface of the interstitial tissue layer, thus forming two architecturally distinct layers. In certain embodiments, the epithelial tissue and interstitial tissue layers are in continuous contact. In certain embodiments, at least 99% of the epithelial tissue layer is in continuous contact with the interstitial tissue layer. In certain embodiments, at least 95% of the epithelial tissue layer is in continuous contact with the interstitial tissue layer. In certain embodiments, at least 90% of the epithelial tissue layer is in continuous contact with the interstitial tissue layer. In certain embodiments, at least 80% of the epithelial tissue layer is in continuous contact with the interstitial tissue layer. In certain embodiments, at least 70% of the epithelial tissue layer is in continuous contact with the interstitial tissue layer. In certain embodiments, at least 60% of the epithelial tissue layer is in continuous contact with the interstitial tissue layer. In certain embodiments, at least 50% of the epithelial tissue layer is in continuous contact with the interstitial tissue layer. In certain embodiments, less than 99% of the epithelial tissue layer is in continuous contact with the interstitial tissue layer. In certain embodiments, less than 98% of the epithelial tissue layer is in continuous contact with the interstitial tissue layer. In certain embodiments, less than 97% of the epithelial tissue layer is in continuous contact with the interstitial tissue layer. In certain embodiments, less than 95% of the epithelial tissue layer is in continuous contact with the interstitial tissue layer. In certain embodiments, less than 90% of the epithelial tissue layer is in continuous contact with the interstitial tissue layer. In certain embodiments, less than 80% of the epithelial tissue layer is in continuous contact with the interstitial tissue layer. In certain embodiments, the epithelial tissue layer completely covers the apical surface of the interstitial tissue layer. In certain embodiments, the epithelial tissue layer covers at least 99% of the apical surface of the interstitial tissue layer. In certain embodiments, the epithelial tissue layer covers at least 95% of the apical surface of the interstitial tissue layer. In certain embodiments, the epithelial tissue layer covers at least 90% of the apical surface of the interstitial tissue layer. In certain embodiments, the epithelial tissue layer covers at least 80% of the apical surface of the interstitial tissue layer. In certain embodiments, the epithelial tissue layer covers at least 70% of the apical surface of the interstitial tissue layer. In certain embodiments, the epithelial tissue layer covers at least 60% of the apical surface of the interstitial tissue layer. In certain embodiments, the epithelial tissue layer covers at least 50% of the apical surface of the interstitial tissue layer. In certain embodiments, the epithelial tissue layer covers less than 99% of the apical surface of the interstitial tissue layer. In certain embodiments, the epithelial tissue layer covers less than 98% of the apical surface of the interstitial tissue layer. In certain embodiments, the epithelial tissue layer covers less than 97% of the apical surface of the interstitial tissue layer. In certain embodiments, the epithelial tissue layer covers less than 95% of the apical surface of the interstitial tissue layer. In certain embodiments, the epithelial tissue layer covers less than 90% of the apical surface of the interstitial tissue layer. In certain embodiments, the epithelial tissue layer covers less than 80% of the apical surface of the interstitial tissue layer. In certain embodiments, the epithelial tissue layer covers less than 70% of the apical surface of the interstitial tissue layer.

Architecture of the Epithelial Tissue Layer

Normally an epithelial tissue cell forms tight junctions with neighboring cells. The tight junctions are marked by the transmembrane protein family the cadherins. One of these, E-cadherin, is especially prominent at tight junctions in renal tissue, and marks their formation. In certain embodiments, the epithelial tissue layer consists of cells that form tight junctions. In certain embodiments, substantially all cells in the epithelial tissue layer form a tight junction with at least one neighboring cell. In certain embodiments, at least 99% of cells in the epithelial tissue layer form a tight junction with at least one other cell. In certain embodiments, at least 95% of cells in the epithelial tissue layer form a tight junction with at least one other cell. In certain embodiments, at least 90% of cells in the epithelial tissue layer form a tight junction with at least one other cell. In certain embodiments, at least 80% of cells in the epithelial tissue layer form a tight junction with at least one other cell. In certain embodiments, at least 70% of cells in the epithelial tissue layer form a tight junction with at least one other cell. In certain embodiments, at least 60% of cells in the epithelial tissue layer form a tight junction with at least one other cell. In certain embodiments, at least 50% of cells in the epithelial tissue layer form a tight junction with at least one other cell.

Viability and Density of the Cell Layers

An advantage of bioprinting by the methods of this disclosure is that cells can be printed at high density and high viability. In certain embodiments, the density of the interstitial cell layer is at least $1 \times 10^6$ cells per mL. In certain embodiments, the density of the interstitial cell layer is at least $5 \times 10^6$ cells per mL. In certain embodiments, the density of the interstitial cell layer is at least $10 \times 10^6$ cells per mL. In certain embodiments, the density of the interstitial cell layer is at least $20 \times 10^6$ cells per mL. In certain embodiments, the density of the interstitial cell layer is at least $50 \times 10^6$ cells per mL. In certain embodiments, the density of the interstitial cell layer is at least $100 \times 10^6$ cells per mL. In certain embodiments, the density of the interstitial cell layer is at least $200 \times 10^6$ cells per mL. In certain embodiments, the density of the interstitial cell layer is at least $500 \times 10^6$ cells per mL. In certain embodiments, the density of the interstitial cell layer is between about $100 \times 10^6$ cells per mL and about $900 \times 10^6$ cells pre mL. In certain embodiments, the density of the interstitial cell layer is between about $100 \times 10^6$ cells per mL and about $700 \times 10^6$ cells pre mL. In certain embodiments, the density of the interstitial cell layer is between about 100×10⁶ cells per mL and about 600×10⁶ cells pre mL. In certain embodiments, the density of the interstitial cell layer is between about 100×10⁶ cells per mL and about 500×10⁶ cells pre mL. In certain embodiments, the density of the interstitial cell layer is between about 100×10⁶ cells per mL and about 300×10⁶ cells pre mL. In certain embodiments, the density of the interstitial cell layer is between about 100×10⁶ cells per mL and about 200×10⁶ cells pre mL. In certain embodiments, the viability of the interstitial tissue layer is greater than 99% living cells by volume. In certain embodiments, the viability of the interstitial tissue layer is greater than 95% living cells by volume. In certain embodiments, the viability of the interstitial tissue layer is greater than 90% living cells by volume. In certain embodiments, the viability of the interstitial tissue layer is greater than 80% living cells by volume. In certain embodiments, the viability of the interstitial tissue layer is greater than 70% living cells by volume. In certain embodiments, the viability of the interstitial tissue layer is greater than 60% living cells by volume. In certain embodiments, the viability of the interstitial tissue layer is greater than 50% living cells by volume. In certain embodiments, this viability is maintained for at least 8, 12, 24, 48, 72, 96, or more hours post printing. In certain embodiments, this viability is maintained for at least 1, 2, 3, 4, 5, 6, 7, 8, 9, 10, 11, 12, 13, 14, 21, or more days post printing. In certain embodiments, the density of the epithelial cell layer is at least $1\times10^5$ cells per mL. In certain embodiments, the density of the epithelial cell layer is at least $2\times10^5$ cells per mL. In certain embodiments, the density of the epithelial cell layer is at least $5\times10^5$ cells per mL. In certain embodiments, the density of the epithelial cell layer is at least $1\times10^6$ cells per mL. In certain embodiments, the density of the epithelial cell layer is at least $5\times10^6$ cells per mL. In certain embodiments, the density of the epithelial cell layer is at least $10\times10^6$ cells per mL. In certain embodiments, the density of the epithelial cell layer is at least $20\times10^6$ cells per mL. In certain embodiments, the density of the epithelial cell layer is at least $50\times10^6$ cells per mL. In certain embodiments, the density of the epithelial cell layer is at least $100\times10^6$ cells per mL. In certain embodiments, the density of the epithelial cell layer is at least $200\times10^6$ cells per mL. In certain embodiments, the density of the epithelial cell layer is at least $500\times10^6$ cells per mL. In certain embodiments, the density of the epithelial cell layer is less than $1\times10^5$ cells per mL. In certain embodiments, the density of the epithelial cell layer is less than $2\times10^5$ cells per mL. In certain embodiments, the density of the epithelial cell layer is less than $5\times10^5$ cells per mL. In certain embodiments, the density of the epithelial cell layer is less than $1\times10^6$ cells per mL. In certain embodiments, the density of the epithelial cell layer is less than $5\times10^6$ cells per mL. In certain embodiments, the density of the epithelial cell layer is less than $10\times10^6$ cells per mL. In certain embodiments, the viability of the epithelial tissue layer is greater than 99% living cells by volume. In certain embodiments, the viability of the epithelial tissue layer is greater than 95% living cells by volume. In certain embodiments, the viability of the epithelial tissue layer is greater than 90% living cells by volume. In certain embodiments, the viability of the epithelial tissue layer is greater than 80% living cells by volume. In certain embodiments, the viability of the epithelial tissue layer is greater than 70% living cells by volume. In certain embodiments, the viability of the epithelial tissue layer is greater than 60% living cells by volume. In certain embodiments, the viability of the epithelial tissue layer is greater than 50% living cells by volume. In certain embodiments, this viability is maintained for at least 8, 12, 24, 48, 72, or 96 hours post-printing. In certain embodiments, this viability is maintained for at least 1, 2, 3, 4, 5, 6, 7, 8, 9, 10, 11, 12, 13, or 14 days post-printing.

Uniformity of Tissue Architecture

One advantage of bioprinting using the methods of this disclosure is the high degree of uniformity achieved by the process that is reflected in the corresponding tissue. In certain embodiments, the thickness of the renal tubule model is substantially uniform. In certain embodiments, greater than 99% of the renal tubule model is within 10% plus or minus of the overall mean thickness of the renal tubule model. In certain embodiments, greater than 95% of the renal tubule model is within 10% plus or minus of the overall mean thickness of the renal tubule model. In certain embodiments, greater than 90% of the renal tubule model is within 10% plus or minus of the overall mean thickness of the renal tubule model. In certain embodiments, greater than 80% of the renal tubule model is within 10% plus or minus of the overall mean thickness of the renal tubule model. In certain embodiments, greater than 70% of the renal tubule model is within 10% plus or minus of the overall mean thickness of the renal tubule model. In certain embodiments, greater than 99% of the renal tubule model is within 20% plus or minus of the overall mean thickness of the renal tubule model. In certain embodiments, greater than 95% of the renal tubule model is within 20% plus or minus of the overall mean thickness of the renal tubule model. In certain embodiments, greater than 90% of the renal tubule model is within 20% plus or minus of the overall mean thickness of the renal tubule model. In certain embodiments, greater than 80% of the renal tubule model is within 20% plus or minus of the overall mean thickness of the renal tubule model. In certain embodiments, greater than 70% of the renal tubule model is within 20% plus or minus of the overall mean thickness of the renal tubule model.

Non-Cellular Components of Bio-Inks and Cell Layers

Often cells or bio-inks that are bioprinted contain excipients or extrusion compounds that improve their suitability for bioprinting. Examples of extrusion compounds include, but are not limited to gels, hydrogels, peptide hydrogels, amino acid-based gels, surfactant polyols (e.g., Pluronic F-127 or PF-127), thermo-responsive polymers, hyaluronates, alginates, extracellular matrix components (and derivatives thereof), collagens, gelatin, other biocompatible natural or synthetic polymers, nanofibers, and self-assembling nanofibers. In some embodiments, the extrusion compound contains a synthetic polymer. In some embodiments, the extrusion compound contains a non-synthetic polymer that is not normally associated with mammalian tissues. In some embodiments, extrusion compounds are removed after bioprinting by physical, chemical, or enzymatic means. In some embodiments, the bio-inks of the present disclosure contain more than 1% extrusion compound by weight. In some embodiments, the renal tubule models of the present disclosure contain more than 1% extrusion compound by weight. In some embodiments, the bio-inks of the present disclosure contain less than 5% extrusion compound by weight. In some embodiments, the bio-inks of the present disclosure contain less than 2% extrusion compound by weight. In some embodiments, the bio-inks of the present disclosure contain less than 1% extrusion compound by weight. In some embodiments, the renal tubule models of the present disclosure contain less than 5% extrusion compound by weight. In some embodiments, the renal tubule models of the present disclosure contain less than 2% extrusion compound by weight. In some embodiments, the renal tubule models of the present disclosure contain less than 1% extrusion compound by weight. In some embodiments, the epithelial bio-ink is free from hydrogel. In some embodiments, the epithelial bio-ink is free from extrusion compound. In some embodiments, the epithelial bio-ink is free from synthetic polymers that are used as an excipient or estrus in compound. In some embodiments, the renal tubule model is free from synthetic polymers that are used as an excipients or extrusion compounds. In some embodiments, the epithelial cell layer is free from synthetic polymers that are used as an excipients or extrusion compounds. In some embodiments, the interstitial cell layer is free from synthetic polymers that are used as an excipients or extrusion compounds.

Print Surfaces

Provided herein are renal tubule models that are attached to a biocompatible surface. In certain embodiments, the interstitial tissue layer is printed onto a biocompatible surface. In certain embodiments, the biocompatible surface is a membrane with a pore size greater than 0.4 In certain embodiments, the biocompatible surface has a pore size of about 1 μm. In certain embodiments, the biocompatible surface is coated with a composition to improve cell adherence or viability. In certain embodiments, the renal tubule modules are printed into 6-well, 12-well, 24-well, 48-well, 96-well, or 384-well plates. In certain embodiments, the renal tubule modules are printed into tissue culture plates with diameters of 60, 100 or 150 mm or more. In certain embodiments, the renal tubule modules are printed into tissue culture flasks or onto microfluidic chips. In certain embodiments, the renal tubule modules are printed into/onto transwell inserts.

Process for Production of Renal Tubule Models

This disclosure supports methods and processes for fabricating renal tubule models. In certain embodiments, the product of a three-dimensional, engineered, biological renal tubule model is produced by the process of bioprinting. In certain embodiments, at least one constituent of the product of a three-dimensional, engineered, biological renal tubule model is produced by the process of bioprinting. In certain embodiments, the process of fabricating a three-dimensional, engineered, biological renal tubule model, comprises: preparing a renal interstitial bio-ink, the interstitial bio-ink comprising a plurality of interstitial cell types, the interstitial cell types comprising renal fibroblasts and endothelial cells; preparing a renal epithelial bio-ink, the epithelial bio-ink comprising renal tubular epithelial cells; depositing the renal interstitial bio-ink and the renal epithelial bio-ink such that the renal epithelial bio-ink forms a layer on at least one surface of the layer of renal interstitial bio-ink; and maturing the deposited bio-ink in a cell culture media to allow the cells to cohere to form the three-dimensional, engineered, biological renal tubule model. In certain embodiments, the renal interstitial tissue bio-ink forms a renal interstitial tissue layer with an apical and basolateral surface. In certain embodiments, the renal epithelial bio-ink is deposited in contact with the apical surface of the renal interstitial tissue layer. In certain embodiments, the renal epithelial bio-ink consists essentially of renal tubular epithelial cells. In certain embodiments, the renal epithelial bio-ink consists essentially of primary renal tubular epithelial cells. In certain embodiments, the primary renal tubular epithelial cells are isolated from a subject with a disease that affects kidney function. In certain embodiments, the primary renal tubular epithelial cells are isolated from a subject with polycystic kidney disease. In certain embodiments, the primary renal tubular epithelial cells are isolated from a subject with diabetes mellitus type II. In certain embodiments, the renal epithelial bio-ink comprises renal cell carcinoma cells. In certain embodiments, the renal epithelial bio-ink is deposited in a monolayer. In certain embodiments, the renal interstitial tissue bio-ink is deposited in a monolayer. In certain embodiments, the layer of renal epithelial tissue is deposited in continuous contact with the layer of renal interstitial tissue. In certain embodiments, the renal epithelial bio-ink forms a layer that covers by 50% or more the apical surface of the layer of renal interstitial tissue. In certain embodiments, the renal epithelial bio-ink forms a layer that covers by 70% or more the apical surface of the layer of renal interstitial tissue. In certain embodiments, the renal epithelial bio-ink forms a layer that covers by 90% or more the apical surface of the layer of renal interstitial tissue. In certain embodiments, at least 50% of renal epithelial cells of the renal epithelial layer form tight junctions with other renal epithelial cells. In certain embodiments, at least 70% of renal epithelial cells of the renal epithelial layer form tight junctions with other renal epithelial cells. In certain embodiments, at least 90% of renal epithelial cells of the renal epithelial layer form tight junctions with other renal epithelial cells. In certain embodiments, the renal tubule model is between 50 and 500 μm thick. In certain embodiments, the renal tubule model is about 100 μm thick. In certain embodiments, the renal epithelial bio-ink further comprises an extrusion compound. In certain embodiments, the fibroblasts and endothelial cells are present in the renal interstitial bio-ink at a ratio of about 95:5 to about 5:95 fibroblasts to endothelial cells. In certain embodiments, the fibroblasts and endothelial cells are present in the renal interstitial bio-ink at a ratio of about 75:25 to about 25:75 fibroblasts to endothelial cells. In certain embodiments, the fibroblasts and endothelial cells are present in the renal interstitial bio-ink at a ratio of about 60:40 to about 40:60 fibroblasts to endothelial cells. In certain embodiments, the fibroblasts and endothelial cells are present in the renal interstitial bio-ink at a ratio of about 50:50 fibroblasts to endothelial cells. In certain embodiments, the renal interstitial bio-ink further comprises secretory cells. In certain embodiments, the renal interstitial bio-ink further comprises immune cells. In certain embodiments, the renal interstitial bio-ink further comprises an extrusion compound. In certain embodiments, the renal interstitial bio-ink comprises glomerular cells. In certain embodiments, the model is fabricated substantially free of pre-formed scaffold. In certain embodiments, the renal fibroblasts, endothelial cells, and renal tubular epithelial cells are mammalian cells. In certain embodiments, either of the renal interstitial bio-ink or renal epithelial bio-ink forms a planar layer after deposition. In certain embodiments, the renal tubule model is of a uniform thickness. In certain embodiments, the renal interstitial bio-ink is deposited onto a biocompatible membrane. In certain embodiments, the renal interstitial bio-ink is deposited onto a biocompatible membrane with a pore size greater than 0.4 In certain embodiments, the renal interstitial bio-ink is deposited onto a biocompatible membrane with a pore size of about 1 μm. In certain embodiments, the three-dimensional, engineered, biological renal tubule models are deposited to form an array. In certain embodiments, the three-dimensional, engineered, biological renal tubule models are deposited to form an array configured to allow between about 20 μm and about 100 μm of space between each renal tubule model. In certain embodiments, the renal interstitial bio-ink is at least 30% living cells by volume. In certain embodiments, the renal interstitial bio-ink is at least 70% living cells by volume. In certain embodiments, the renal interstitial bio-ink is at least 90% living cells by volume. In certain embodiments, the renal interstitial bio-ink is deposited by extrusion bioprinting. In certain embodiments, the renal epithelial bio-ink is deposited by ink-jet bioprinting. In certain embodiments, the renal interstitial bio-ink is not deposited by ink-jet bioprinting. In certain embodiments, any layer of the renal tubule model is viable in in vitro culture in culture after 3 days. In certain embodiments, any layer of the renal tubule model is viable in in vitro culture after 10 days.

In certain embodiments, the 3D renal tubule models disclosed herein are produced by an additive manufacturing process. The additive manufacturing process for 3D tubule models herein allows customized fabrication of 3D renal tubule models for in vitro purposes. This is significant in that the tissues are fabricated due to a user specified design. In certain embodiments, the 3D renal tubule models contain only the cells that the user specifies (e.g., uses as inputs to the additive manufacturing process). In certain embodiments, the 3D renal tubule models contain only the cell types that the user specifies. In certain embodiments, the 3D renal tubule models contain only the number of cells or concentration of cells that the user specifies. In certain embodiments, the 3D renal tubule models contain cells that have been treated with a small molecule, therapeutic molecule, or therapeutic substance before or during fabrication. A therapeutic molecule or substance being any molecule intended to treat a disease or elicit a biological response. In certain embodiments, the 3D renal tubule models contain biocompatible or tissue culture plastics, biocompatible synthetic polymers, cross linkable gels, reversibly cross-linked gels and other non-cellular constituents.

Maturation of Renal Tubule Models

In certain embodiments, the renal tubule models of the present disclosure are matured for a certain amount of time after bioprinting. In certain embodiments, the models are matured for at least 1, 2, 3, 4, 5, 6, 7, 8, 9, 10, 11, 12, 16, 18, 24 hours or more before use. In certain embodiments, the models are matured for at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 days or more before use. In some embodiments, shipment or transfer of the tissues is a use. In certain embodiments, the interstitial layer of the renal tubule model of the present disclosure is matured for a certain amount of time after bioprinting before addition of the epithelial layer. In certain embodiments, the interstitial layer is matured for at least 1, 2, 3, 4, 5, 6, 7, 8, 9, 10, 11, 12, 16, 18, 24 hours or more before use. In certain embodiments, the interstitial layer is matured for at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 days or more before use. In some embodiments, shipment or transfer of the tissues is a use. In some embodiments, the epithelial layer is bioprinted onto the interstitial layer within 1, 2, 3, 4, 5, 6, 7, 8, 9, 10, 11, 12, 16, 18, 24 hours after bioprinting of the interstitial layer. In some embodiments, shipment or transfer of the tissues is a use. In some embodiments, the epithelial layer is bioprinted onto the interstitial layer within 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 days after bioprinting of the interstitial layer.

In Vitro Assays

In some embodiments, the renal tubules and arrays disclosed herein are for use in in vitro assays. In some embodiments, an "assay" is a procedure for testing or measuring the presence or activity of a substance (e.g., a chemical, molecule, biochemical, drug, etc.) in an organic or biologic sample (e.g., cell aggregate, tissue, organ, organism, etc.). In further embodiments, assays include qualitative assays and quantitative assays. In still further embodiments, a quantitative assay measures the amount of a substance such as a chemical or biomolecule in a sample.

In various embodiments, the renal tubules and arrays are for use in, by way of non-limiting example, image-based assays, measurement of secreted proteins, expression of markers, and production of proteins or mRNAs. In various further embodiments, the renal tubules and arrays are for use in assays to detect or measure one or more of: molecular binding (including radioligand binding), molecular uptake, activity (e.g., enzymatic activity and receptor activity, etc.), gene expression, protein expression, protein modifications (non-limiting examples include: phosphorylation, ubiquitination, acetylation, glycosylation, lipidation, etc.), receptor agonism, receptor antagonism, cell signaling, apoptosis, chemosensitivity, transfection, cell migration, chemotaxis, cell viability, cell proliferation, safety, efficacy, metabolism, toxicity, infectivity, and abuse liability. In various embodiments, the renal tubules are for toxicology, pharmaceutical or toxicity testing.

In some embodiments, the renal tubules and arrays are for use in immunoassays. Immunoassays include, for example, flow cytometry, high throughput or low throughput image analysis, immunoprecipitation, radio-immunoassay (RIA), enzyme-linked immunosorbent assays (ELISA)., western blot, homogenous assays, such as AlphaLISA™ and related technologies that rely on time resolved fluorescence or fluorescence resonance energy transfer (FRET). In further embodiments, immunoassays are competitive immunoassays or noncompetitive immunoassays. In a competitive immunoassay, for example, the antigen in a sample competes with labeled antigen to bind with antibodies and the amount of labeled antigen bound to the antibody site is then measured. In a noncompetitive immunoassay (also referred to as a "sandwich assay"), for example, antigen in a sample is bound to an antibody site; subsequently, labeled antibody is bound to the antigen and the amount of labeled antibody on the site is then measured.

In some embodiments, the renal tubules and arrays are for use in ELISA. In further embodiments, an ELISA is a biochemical technique used to detect the presence of an antibody or an antigen in a sample. In ELISA, for example, at least one antibody with specificity for a particular antigen is utilized. By way of further example, a sample with an unknown amount of antigen is immobilized on a solid support (e.g., a polystyrene microtiter plate) either non-specifically (via adsorption to the surface) or specifically (via capture by another antibody specific to the same antigen, in a "sandwich" ELISA). By way of still further example, after the antigen is immobilized, the detection antibody is added, forming a complex with the antigen. The detection antibody is, for example, covalently linked to an enzyme, or is itself detected by a secondary antibody that is linked to an enzyme through bioconjugation.

For example, in some embodiments, an array, microarray, or chip of cells, multicellular aggregates, or tissues is used for drug screening or drug discovery. In further embodiments, an array, microarray, or chip of tissues is used as part of a kit for drug screening or drug discovery. In some embodiments, each renal tubule exists within a well of a biocompatible multi-well container, wherein the container is compatible with one or more automated drug screening procedures and/or devices. In further embodiments, automated drug screening procedures and/or devices include any suitable procedure or device that is computer or robot-assisted.

In further embodiments, arrays for drug screening assays or drug discovery assays are used to research or develop drugs potentially useful in any therapeutic area. In still further embodiments, suitable therapeutic areas include, by way of non-limiting examples, infectious disease, hematology, oncology, pediatrics, cardiology, central nervous system disease, neurology, gastroenterology, hepatology, urology, infertility, ophthalmology, nephrology, orthopedics, pain control, psychiatry, pulmonology, vaccines, wound healing, physiology, pharmacology, dermatology, gene therapy, toxicology, toxicity, and immunology.

In some embodiments, the renal tubules and arrays are for use in cell-based screening. In further embodiments, the cell-based screening is for one or more infectious diseases such as viral, fungal, bacterial or parasitic infection. In further embodiments, the cell-based screening is for kidney cancer, including renal cell carcinoma, juxtaglomerular cell tumor (reninoma), angiomyolipoma, renal oncocytoma, Bellini duct carcinoma, clear-cell sarcoma of the kidney, mesoblastic nephroma, Wilms' tumor, mixed epithelial stromal tumor, and transitional cell carcinoma of the renal pelvis. In further embodiments, the cell-based screening is for nephritis, including, glomerulonephritis, interstitial nephritis or tubulo-interstitial nephritis, pyelonephritis, lupus nephritis and athletic nephritis. In further embodiments, the cell-based screening is for hypertension. In further embodiments, the cell-based screening is for diabetes mellitus, type I, type II and MODY. In further embodiments, the cell-based screening is for a nephropathy, including IgA nephropathy, analgesic nephropathy, or onconephropathy. In some embodiments, the cell-based screening is for polycystic kidney disease or Xanthine oxidase deficiency. In other embodiments, the renal tubules and arrays are for use in the study of cancer initiation, progression, or metastasis. In still further embodiments, the renal tubules and arrays are for use in the study of the interaction of other cell types, such as cancer cells, pathogen-bearing cells, pathogenic cells, immune cells, blood-derived cells, or stem/progenitor cells.

In some embodiments, the constructs or arrays thereof are for use in assessing the performance of biologics, including antibodies, mammalian cells, bacteria, biologically-active proteins, hormones, etc. In other embodiments, the renal tubules or arrays thereof are useful in the study of cell-cell and cell-tissue interactions between the mammalian renal tubules comprising the construct and one or more additional cell types, including but not limited to pathogen-bearing cells, living pathogenic cells, cancer cells, immune cells, blood cells, stem/progenitor cells, or genetically-manipulated cells.

In some embodiments, the array comprises renal tubules and additional tissue constructs. In further embodiments, the renal tubule construct is in direct contact with an additional tissue construct on one or more surfaces. In still further embodiments, the renal tubule is connected to one or more additional tissues constructs or cells via a fluid path or common fluid reservoir. In still further embodiments, the liquid media that contacts the engineered renal tubule construct contains living mammalian cells such as immune cells, blood-derived cells, or tumor-derived cells. In other embodiments, the liquid media that contacts the renal tubule contains bacteria, fungi, viruses, parasites, or other pathogens.

The disclosure herein includes business methods. In some embodiments, the speed and scalability of the techniques and methods disclosed herein are utilized to design, build, and operate industrial and/or commercial facilities for production of renal tubules and/or organs for transplantation or use in generation of cell-based tools for research and development, such as in vitro assays. In further embodiments, the renal tubules and/or organs and arrays thereof are produced, stored, distributed, marketed, advertised, and sold as, for example, cellular arrays (e.g., microarrays or chips), tissue arrays (e.g., microarrays or chips), and kits for biological assays and high-throughput drug screening. In other embodiments, the engineered renal tubules and/or organs and arrays thereof are produced and utilized to conduct biological assays and/or drug screening as a service.

Validation

The ideal engineered renal tissues are fully human and multicellular, comprising renal tubular epithelial cells, renal interstitial fibroblasts, and endothelial cells. Moreover, ideal engineered renal tissues demonstrate specific functions including, but not limited to, CYP1A2, CYP2C9, and CYP3A4 activity, albumin transport, and vitamin D hydroxylation, γ-glutamyl-transferase activity. Also, the ideal engineered renal tissues are characterized by tight junctions, cadherin, polarity of transporters, and CD31 expression and are validated by specific assays including albumin transport, CYP450 activity, histology, and viability. In some embodiments, the renal tubule models of the present disclosure display increased specific functions compared to 2D co-culture or tissue explants that have been maintained in culture longer than 1, 2, 3, 4, 5, 6, 7, 8, 9, 10, or more days. In some embodiments, the renal tubule models of the present disclosure display 2-fold increased specific functions compared to 2D co-culture or tissue explants that have been maintained in culture longer than 1, 2, 3, 4, 5, 6, 7, 8, 9, 10, or more days. In some embodiments, the renal tubule models of the present disclosure display 5-fold or more increased specific functions compared to 2D co-culture or tissue explants that have been maintained in culture longer than 1, 2, 3, 4, 5, 6, 7, 8, 9, 10, or more days. In some embodiments, the renal tubule models of the present disclosure display 2-fold or more increased specific functions compared to 2D co-culture or tissue explants that have been maintained in culture longer than 21 or more days. In some embodiments, the renal tubule models of the present disclosure display 5-fold or more increased specific functions compared to 2D co-culture or tissue explants that have been maintained in culture longer than 27 or more days. In some embodiments, the renal tubule models of the present disclosure display 2-fold or more increased specific functions compared to 2D co-culture or tissue explants that have been maintained in culture longer than 27 r more days. In some embodiments, the renal tubule models of the present disclosure display 5-fold or more increased specific functions compared to 2D co-culture or tissue explants that have been maintained in culture longer than 21 or more days. In certain embodiments, the specific function is γ-glutamyl-transferase activity. In certain embodiments, the specific function is vitamin D hydroxylation.

In some embodiments, the engineered tissues described herein possess key architectural and functional attributes associated with in vivo human renal tissue, including histologic features and renal tubule-specific functions, including but not limited to:

Polarization of renal tubular epithelial cells w/formation of intracellular tight junctions (E-Cad, ZO-1, and Claudins) and correct intracellular localization of transporters (apical: OAT4, URAT1) and integrins (basolateral).

Development of a basal lamina between the tubular cell layer and the underlying interstitium.

Establishment of extensive microvascular networks within the interstitium, including the development of tissue-like tubular cells: microvascular spatial relationships.

Expression of compartment-specific markers, including tubular epithelial transporters (cubilin, megalin, aquaporins), OATs, DRAT), vascular markers (CD31, vWF), demonstration of EPO protein production (if applicable).

Vitamin D synthesis via 25-(OH) 1 hydroxylase (1 OHase).

Production of Angiotensin II.

Active transport of albumin from tubular lumen via cubilin.

Cimetidine transport/accumulation from basolateral surface.

CYP450 and UGT expression involved in metabolism (e.g., CYP2B6, 3A5, 4A11 and UGT 1A9, 2B7, respectively).

EXAMPLES

The following illustrative examples are representative of embodiments, of the software applications, systems, and methods described herein and are not meant to be limiting in any way.

Example 1

A Bioprinted Three-Dimensional Renal Tubule Cell Model

A 3-layer cup shape with dimensions 3 mm×3 mm×0.75 mm was bioprinted onto a Transwell membrane in a 12-well tissue culture plate (FIGS. 2A and 2B). The bottom sheet and two layered walls were composed of 75% adult renal fibroblasts (aRF) and 25% human umbilical vein endothelial cells (HUVEC). The cells were resuspended at 150 million cells/ml in Novogel® 2.0. The cup was filled with a dilute suspension of 100% epithelial cells (MDCK) at 1-5 million cells/ml in 2% gelatin ("Structure 1"). Immediately following bioprinting, structures were surrounded with molten Novogel® 1.0 and were then cultured in a mixture of renal fibroblasts media, HUVEC media, and MDCK media.

Figure 3A:
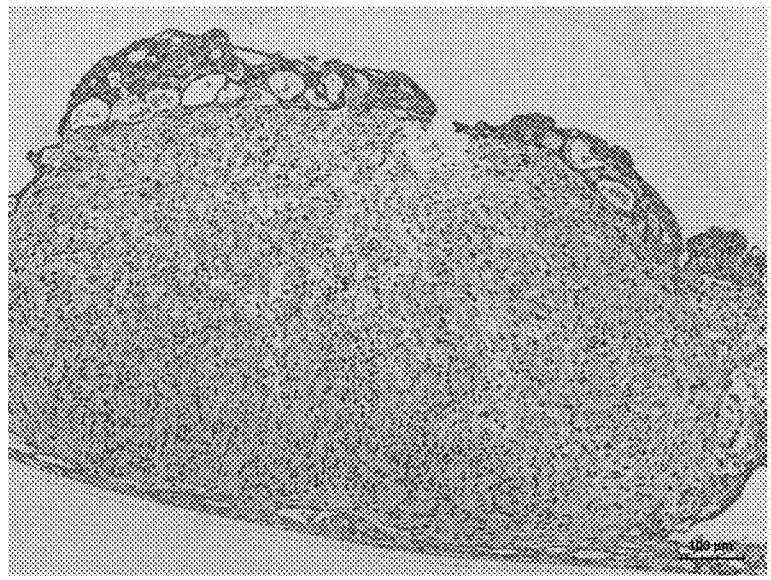
FIGS. 3A and 3B show a non-limiting example of a photomicrograph depicting Structure 1 of Example 1; in this case, H&E staining (FIG. 3A: 100× total magnification.
Figure 3B:
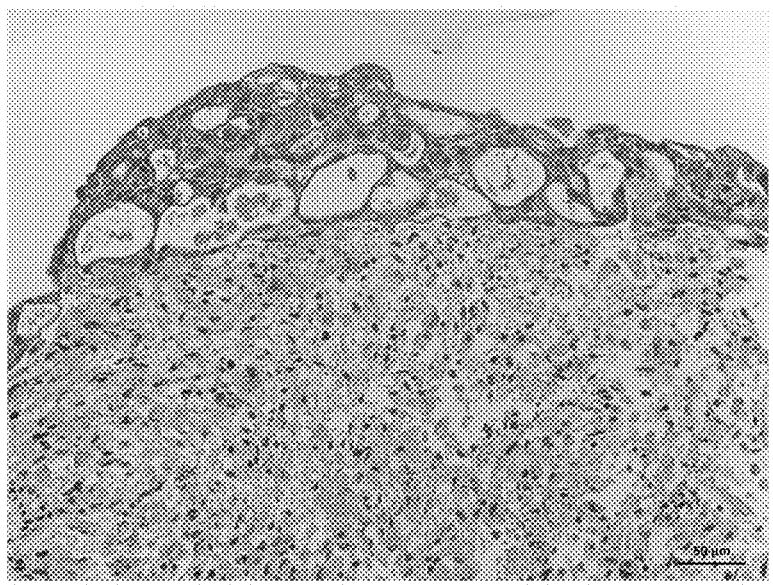
Figure 4:
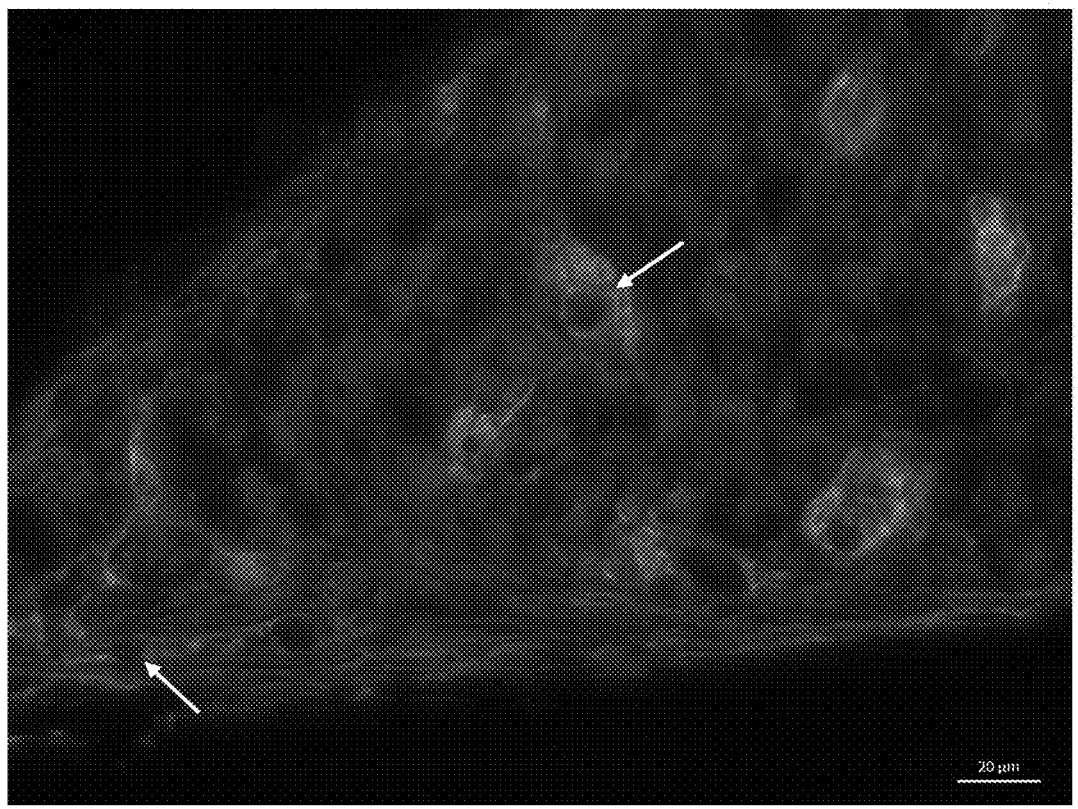
FIG. 4 shows a non-limiting example of a photomicrograph depicting Structure 1 of Example 1; in this case, staining with antibodies against CD31 (green) and TE7 (red) (white arrows indicate HUVEC networks).
Figure 5:
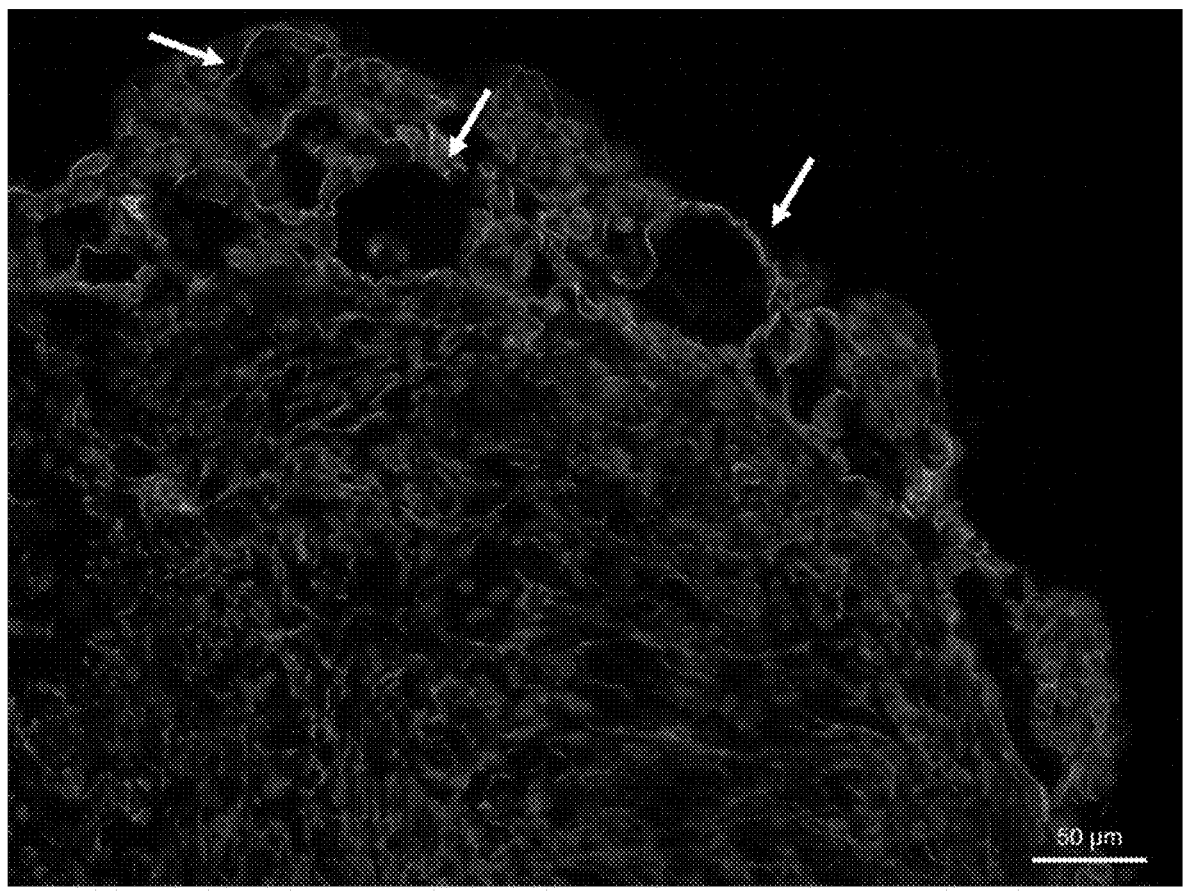
FIG. 5 shows a non-limiting example of a photomicrograph at low magnification depicting Structure 1 of Example 1; staining is with antibodies against E-cadherin (green) and TE7 (red). White arrows indicate presence of tubule structures.

Assessment of Structure 1 was performed by histological staining for cell-type specific markers. A representative H&E stain for Structure 1 is shown in FIGS. 3A and 3B. Constructs were stained for CD31 and TE7 to assess the relative positions of the HUVEC cells and fibroblasts, respectively (FIG. 4). Both cell types are distributed throughout the interstitial layer, which exhibits high cellular density. A robust network of CD31+ cells was found in all analyzed constructs, with some areas possibly demonstrating evidence of microvasculature formation. To visualize the epithelial cells, tissues were stained with antibodies against E-cadherin (FIG. 5). The epithelial cells were concentrated adjacent to the interstitial layer and formed tubule-like structures. This structure has many attractive features pertinent to a human renal proximal tubule model, including a vascularized interstitial layer supporting the growth and organization of polarized epithelial cells.

Example 2

A Bioprinted Three-Dimensional Renal Tubule Cell Model

A sheet with dimensions 3 mm×3 mm×250 μm was bioprinted onto a Transwell membrane in a 12-well plate. The tissue sheet was composed of 75% adult renal fibroblasts and 25% HUVEC resuspended at 150 million cells/ml in Novogel® 2.0. The edges of the sheet were bordered by a 500 μm thick bioprinted hydrogel-only wall composed of Novogel® 3.0. Immediately following bioprinting, the boundary wall was crosslinked with 50 mM calcium chloride for 2 minutes. This solution was then aspirated and the constructs were surrounded with molten Novogel® 1.0. A dilute suspension of epithelial cells (MDCK or hTERT-RPTEC) at 1 million cells/ml was then added to the top surface of the structure by deposition using an inkjet spray module set with a 100 ms valve open time ("Structure 2"). A schematic of Structure 2 is shown in FIGS. 6A and 6B. Use of the inkjet spray module allows for deposition of epithelial cells immediately after printing or interstitial tissues can be printed and matured for several days prior to deposition of epithelial cells, facilitating formation of microvasculature and extracellular matrix that may help support the correct morphology of the epithelial cells.

Figure 7A:
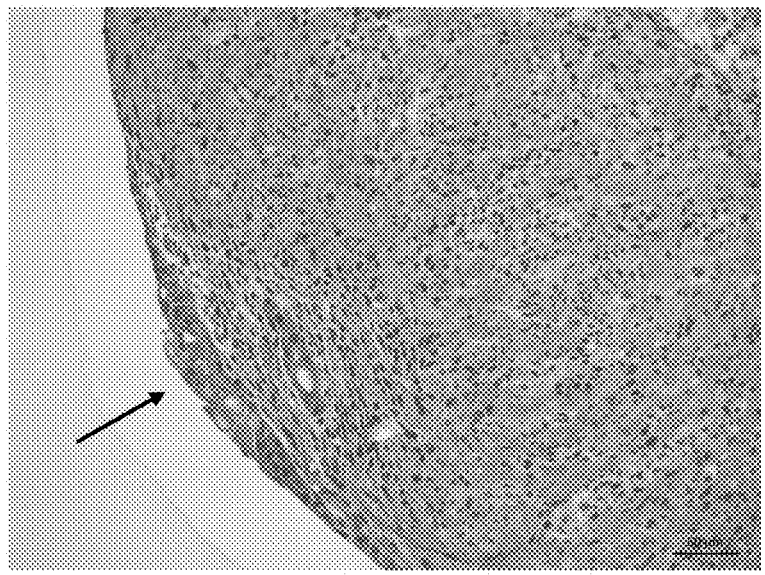
FIGS. 7A and 7B show non-limiting examples of photomicrographs depicting Structure 2 of Example 2; in this case, H&E staining (black arrow indicates epithelial cells).
Figure 7B:
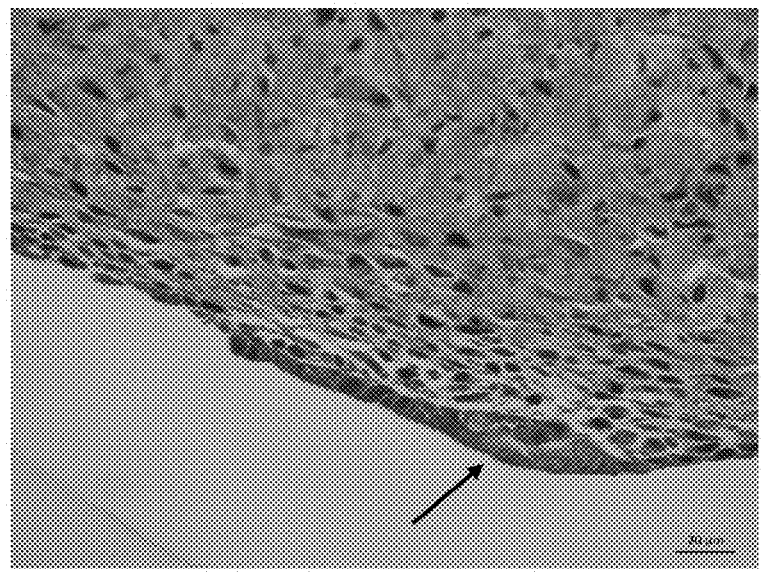
Figure 8A:
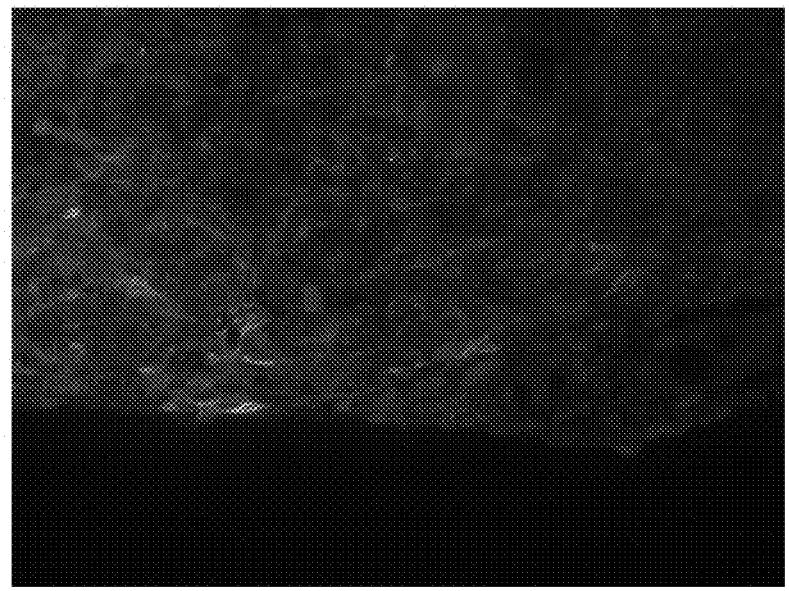
FIGS. 8A and 8B show non-limiting examples of photomicrographs depicting Structure 2 of Example 2; in this case, a photomicrograph demonstrating organization of endothelial cells (FIG. 8A). Green, CD31 staining for HUVECS; and red, TE7 staining for fibroblasts is shown. In this example, epithelial cells are detected on the surface of the tissue by E-cadherin staining (FIG. 8B, green).
Figure 8B:
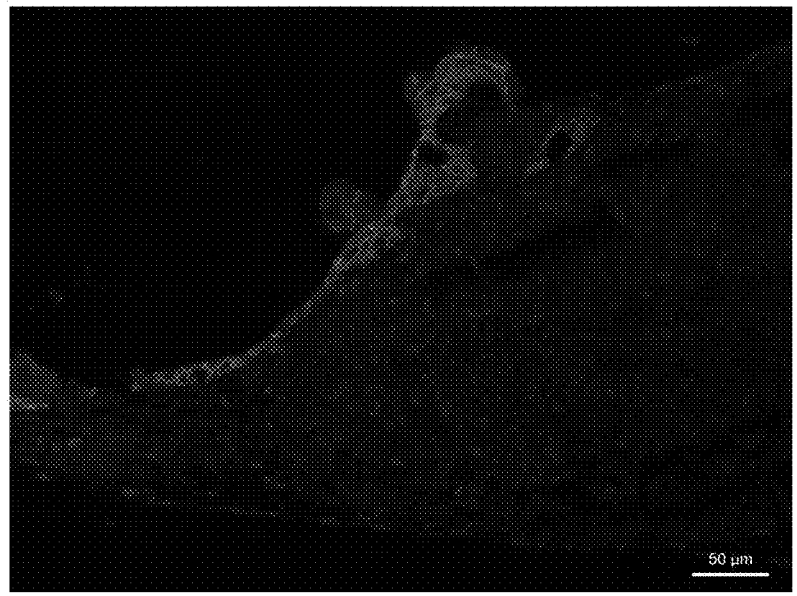

Assessment of Structure 2 was performed by histological staining for cell-type specific markers. A representative H&E stain of Structure 2 is shown in FIGS. 7A and 7B. The tissues exhibit high cellular density, and a thin layer of epithelial cells can be observed (black arrow in FIGS. 7A and 7B). Surprisingly, the inkjet spray module facilitated attachment of epithelial cells to the surface of the interstitial layer and resulted in a much lower cell density on the surface of the tissue, which is necessary for forming a polarized monolayer. Following inkjet spraying, cells retained high viability: greater than 97% for MDCK cells and 94% for hTERT-RPTEC cells as measured by trypan blue exclusion. Evidence of microvascular organization was detected by CD31 staining and the organization of the epithelial cells was verified by E-cadherin staining (FIGS. 8A and 8B).

Example 3

A Bioprinted Three-Dimensional Renal Tubule Cell Model

Figure 9A:
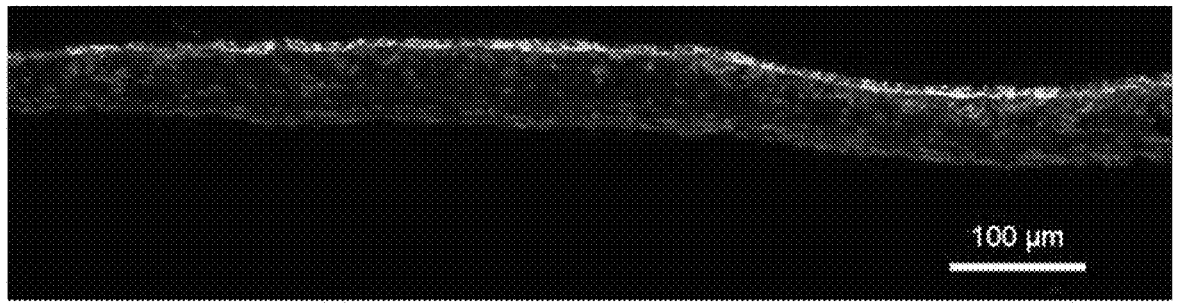
FIGS. 9A, 9B, and 9C show photomicrographs of constructs from Example 3 and depict renal proximal tubule epithelial cells (RPTECs) in 3D renal tissues that exhibit features of polarization. E-cadherin (green) is observed at the lateral membranes between RPTECs, corresponding to localization at tight junctions. Shown are low (FIG. 9A), medium (FIG. 9B), and high (FIG. 9C) magnification.
Figure 9B:
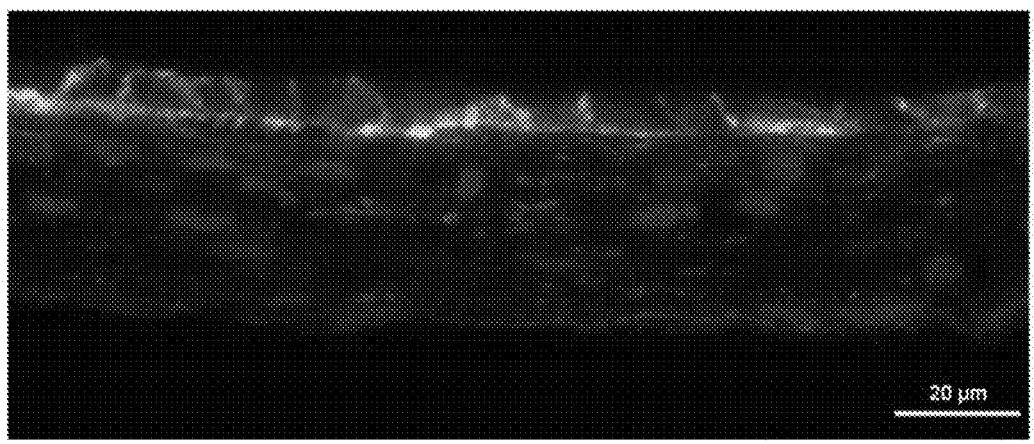
Figure 9C:
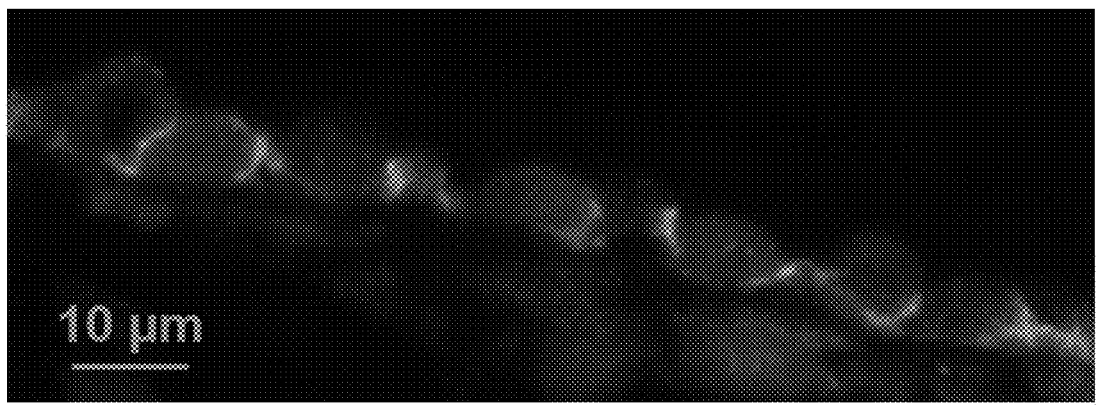
Figure 10A:
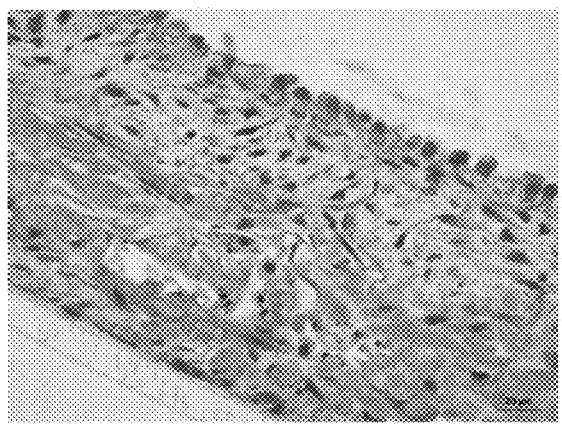
FIGS. 10A and 10B show H & E (FIG. 10A) and trichrome (FIG. 10B) staining of bioprinted renal tissue constructs from Example 3.
Figure 10B:
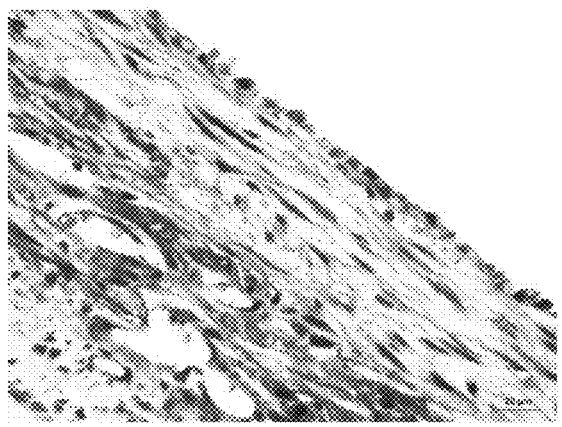
Figure 11A:
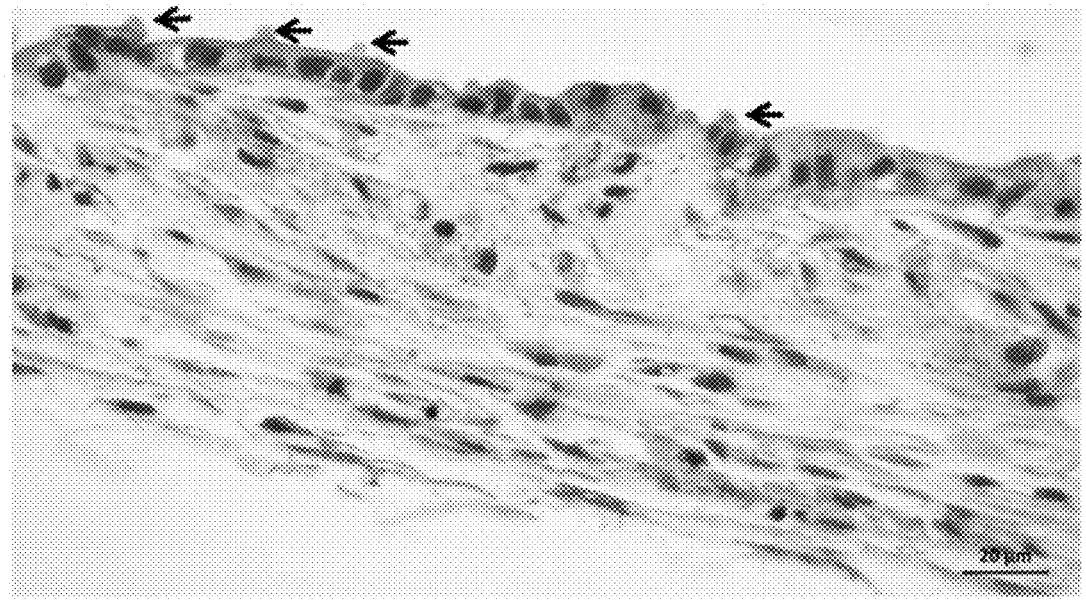
FIGS. 11A and 11B show the constructs from FIG. 11 with brush borders (FIG. 11A, arrows), and collagen deposition (FIG. 11B, arrows) highlighted.
Figure 11B:
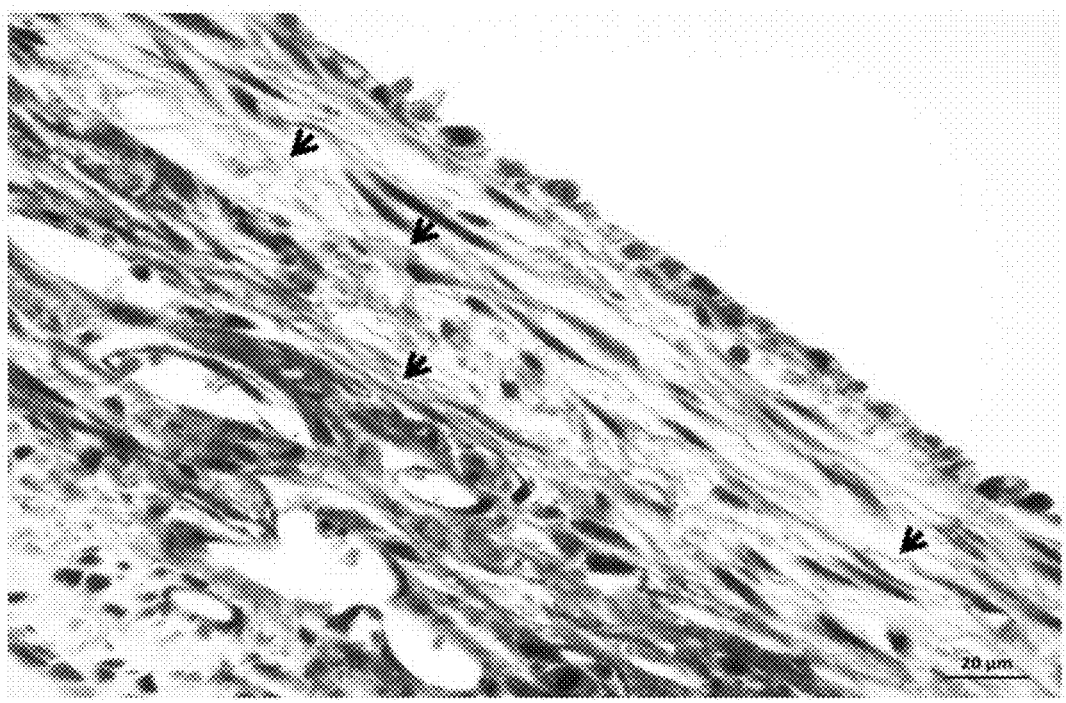
Figure 12:
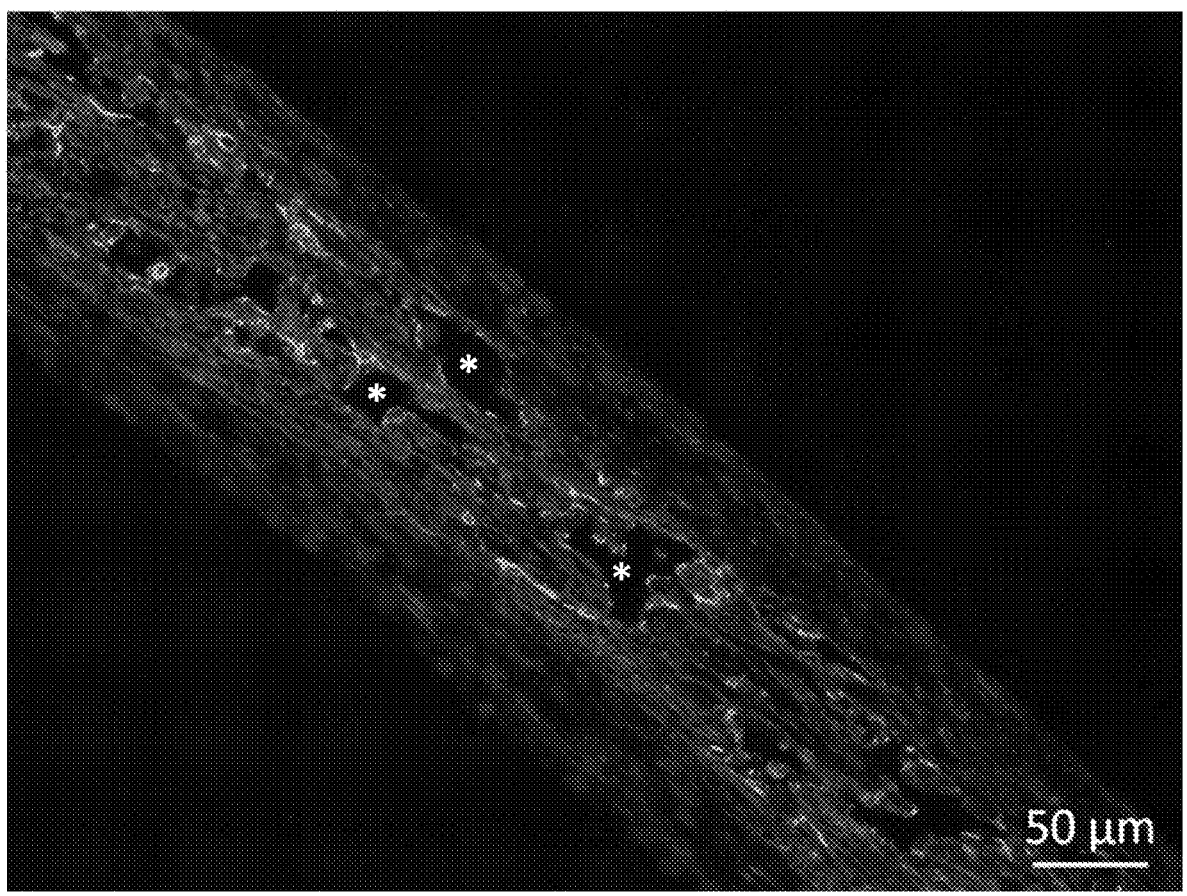
FIG. 12 shows extensive endothelial cell networks are observed in 3D bioprinted renal tissue constructs from Example 3. Staining for CD31, (endothelial cells, green) and TE7 (fibroblasts, red) are shown. Networks with putative lumens lined with endothelial cells are marked with (*).
Figure 13:
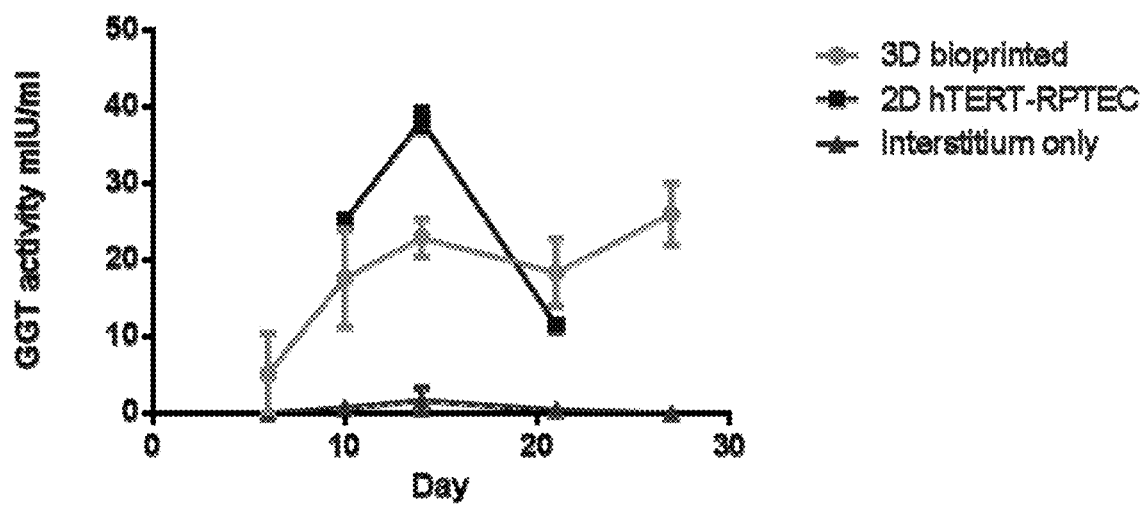
FIG. 13 shows GGT activity in 3D bioprinted renal tissue from Example 3 compared to 2D hTERT-RPTEC and interstitial cells alone.

To reduce the thickness and cellularity of the interstitial layer, the cell ratio was changed to 50% fibroblasts/50% HUVEC the concentration of the cells was $1.25\times10^8$ cells/mL. The interstitial layer of the renal proximal tubule model is composed of renal fibroblasts and HUVECs in Novogel® 2.0. Constructs produced in this example show proximal tubule epithelial cells (RPTECs) in 3D renal tissues that exhibit features of polarization. E-cadherin (green) at the lateral membranes between RPTECs corresponds to tight junctions (FIGS. 9A, B and C). Further, the basement membrane corresponding to the interstitial layer produces collagen (FIGS. 9A and B; stained with red). H & E staining is shown (FIG. 10A), and brush borders are indicated (FIG. 11A, arrows). Trichrome staining indicates collagen secretion (FIGS. 10B, blue and 11B, arrows), and CD31 staining indicates the presence of HUVEC networks (FIG. 12, asterisks). Bioprinted tissues demonstrated γ-glutamyl-transferase (GGT) activity which increases over time in culture, which is indicative of a functioning epithelial layer (FIG. 13). To assess the maturity and function of the epithelial component of the 3D bioprinted tubule model, tissues were homogenized and assayed for gamma glutamyl-transferase (GGT) activity. GGT is an enzyme expressed on the apical surface of epithelial cells and is involved in glutathione homeostasis and xenobiotic metabolism. As a positive control, hTERT-RPTEC cells cultured as a monolayer in 2D were assessed. As a negative control, bioprinted renal interstitial tissues without epithelium were also assayed to verify that the detected GGT activity was epithelial-specific. At culture day 3, 10, 14, 21, or 28, 2D hTERT-RPTEC, 3D interstitium tissues, or 3D bioprinted tubule tissues were homogenized and assessed for functional GGT enzymatic activity using a colorimetric assay available from Sigma-Aldrich. Bioprinted tubule tissues exhibited stable GGT activity from culture day 10-28, with negligible GGT activity detected in bioprinted interstitium only tissues. 2D hTERT-RPTEC monolayer cultures exhibited GGT activity relatively equivalent to that observed in 3D bioprinted tubule tissues, but 2D monolayers exhibited decreased function at day 21, and were not viable at day 28.

Example 4

Figure 14A:
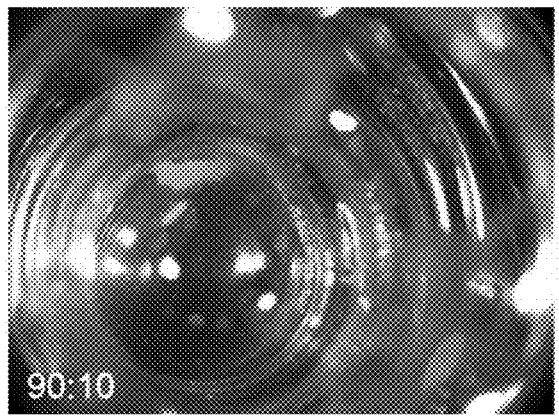
FIGS. 14A, 14B, and 14C show macroscopic views of renal tubule models bioprinted with interstitial layers comprising different ratios of fibroblasts to endothelial cells.
Figure 14B:
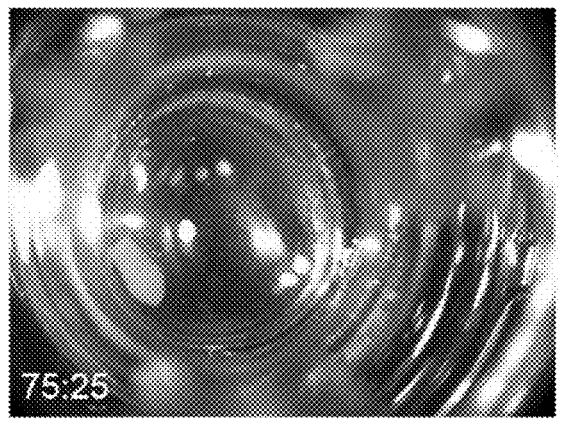
Figure 14C:
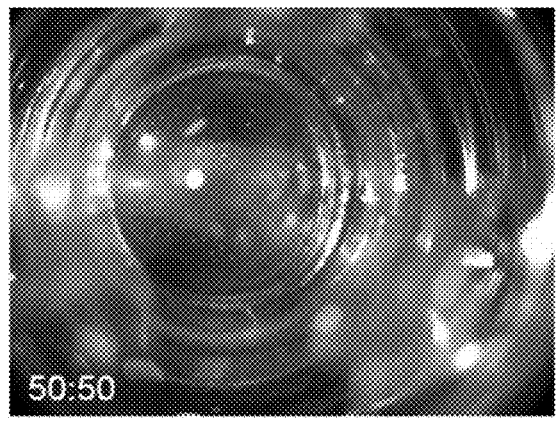
Figure 15A:
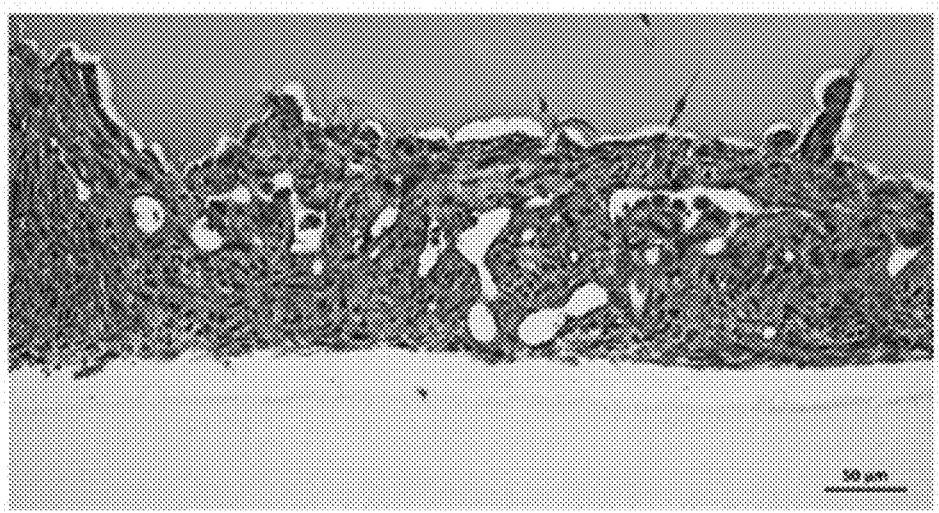
FIGS. 15A, 15B, and 15C show histology of renal tubule models bioprinted with interstitial layers comprising different ratios of fibroblasts to endothelial cells.
Figure 15B:
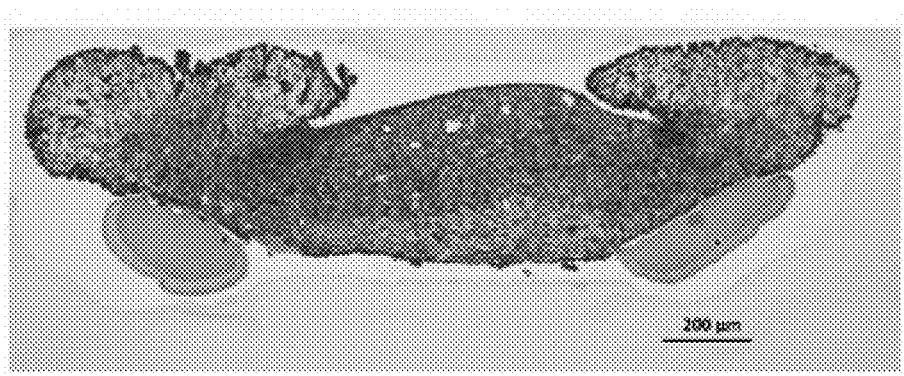
Figure 15C:
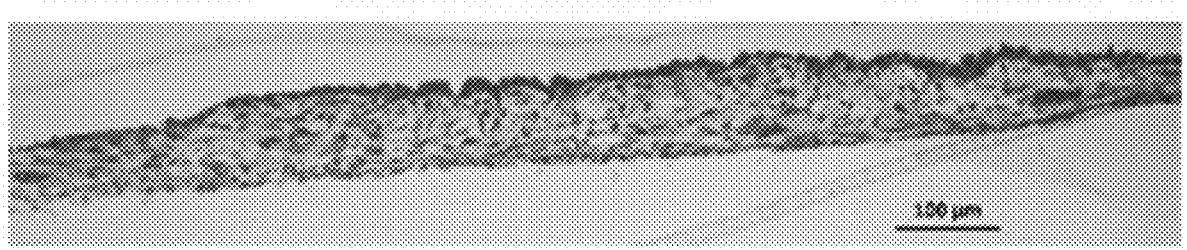

A Three-Dimensional Renal Tubule Model Bioprinted With Different Ratios of Renal Fibroblasts to Endothelial Cells Experiments were undertaken to determine the effect of fibroblast to endothelial cell ratio on tissue morphology. Renal tubule models were bioprinted using bio-inks comprising renal fibroblasts and HUVEC cells at ratios of 90:10; 75:25; and 50:50 (fibroblast to endothelial cells). FIGS. 14 and 15 show the results of this experiment. FIG. 14 shows a macroscopic view of the printed renal tubule model; while FIG. 15 shows corresponding histology stained with Masson's trichrome. At 6 days post print renal tubule models that comprise a 50:50 ratio were substantially planar or flat FIGS. 14C and 15C. Renal tubule models printed at a 90:10 (FIGS. 14A and 15A), and 75:25 (FIGS. 14B and 15B) exhibited curling at 6 days post printing.

Example 5

Uniform Thickness of a Three-Dimensional Renal Tubule Model

Figure 16A:
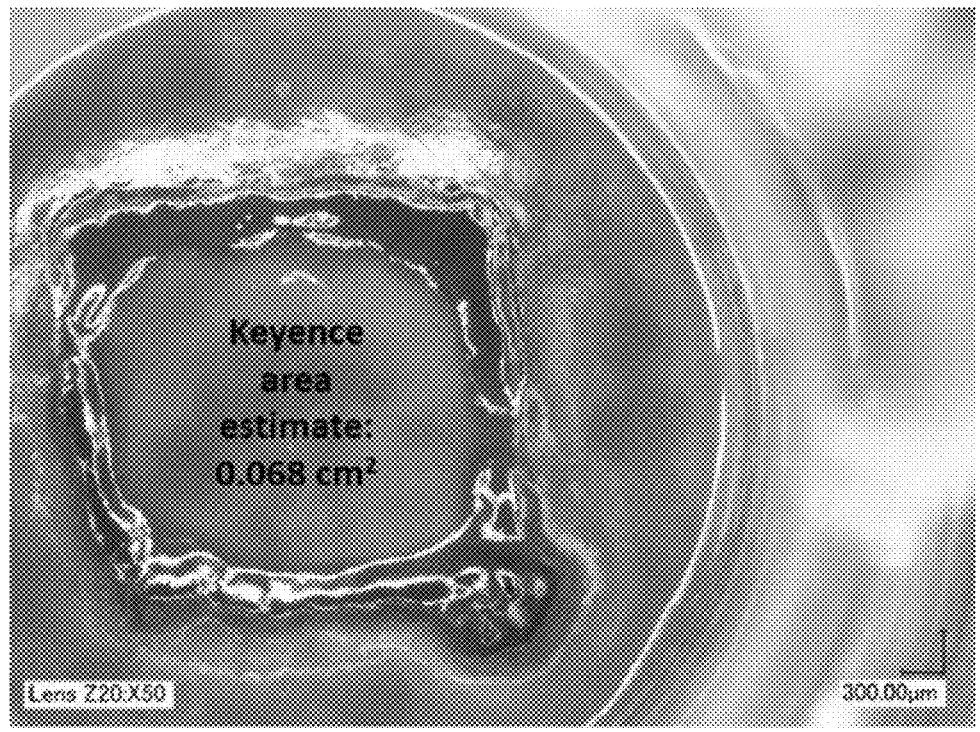
FIGS. 16A and 16B show surface and thickness uniformity data for a bioprinted renal tubule model.
Figure 16B:
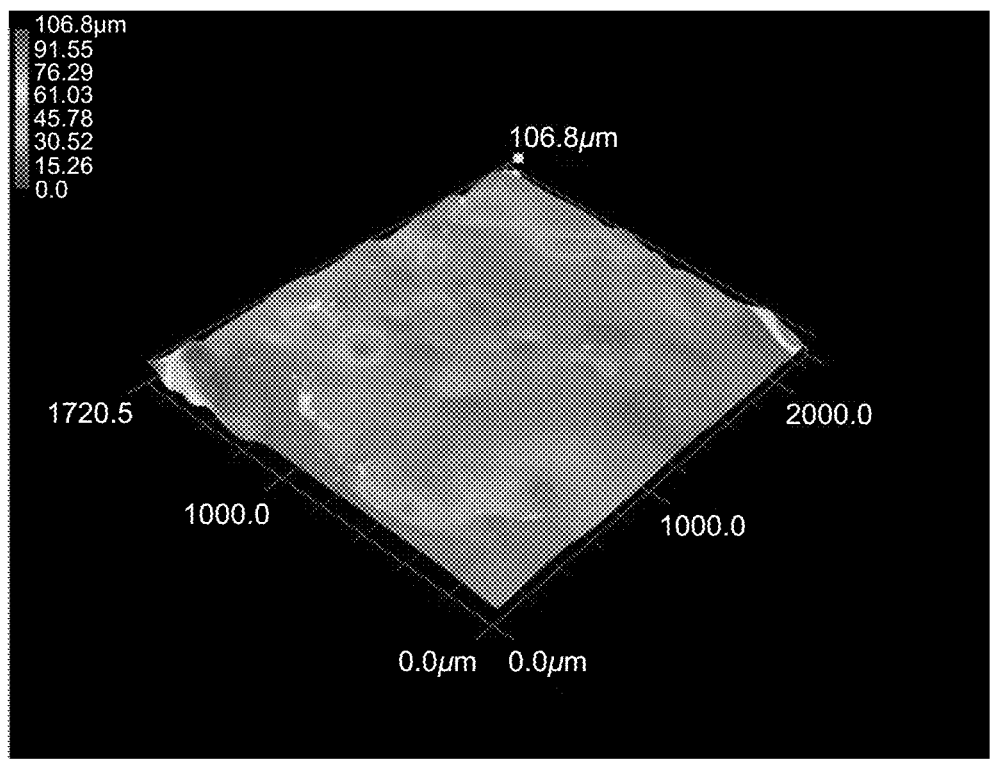

Experiments were undertaken to determine the uniformity of thickness and surface topology of renal tubule models. Renal tubule models were bioprinted into wells of a 12-well plate (FIG. 16A), and analyzed using Keyence technology (FIG. 16B). Bioprinted renal tubule models were cultured for 14 days and analyzed for surface area and thickness using a Keyence VHX-700 digital microscope. The area within the Novogel 3.0 border (see Example 3) was estimated to be 0.068 $cm^2$. Across the tissue within the border, the average thickness was found to be approximately 106.8 μm, with relative uniformity of thickness as evidenced by the heat map shown (extremely thin areas are blue; extremely thick areas are red). Tissues were stained with methyl blue to increase the color contrast and facilitate mapping of the surface of the tissue. Two discrete areas are in the blue range of the heat map, indicating that those areas are much thinner "dimples" that are approximately 20 μm thick. The constructs average 100 μm thick. The data shows a highly uniform, planar and smooth surface morphology with evidence of small dimples.

Example 6

Figure 17A:
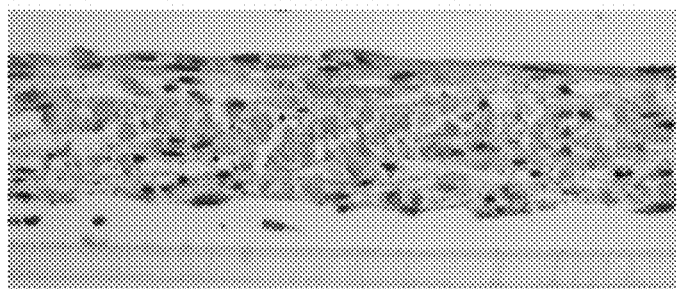
FIGS. 17A, 17B, 17C, and 17D show histology of renal tubule models bioprinted with different amounts of endothelial cells and differing serum concentrations.
Figure 17B:
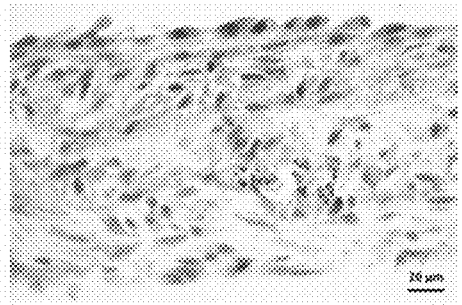
Figure 17C:
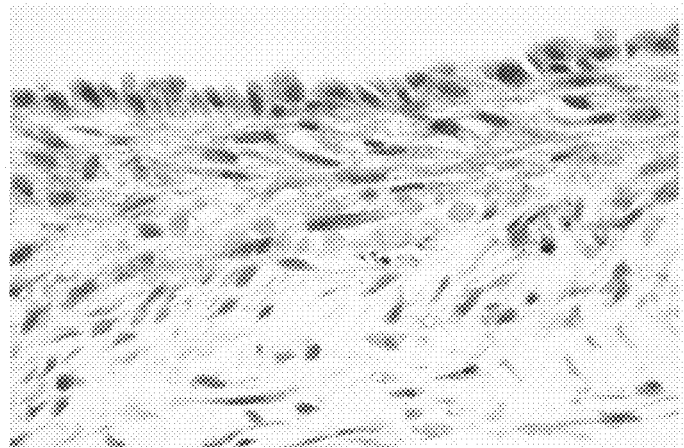
Figure 17D:
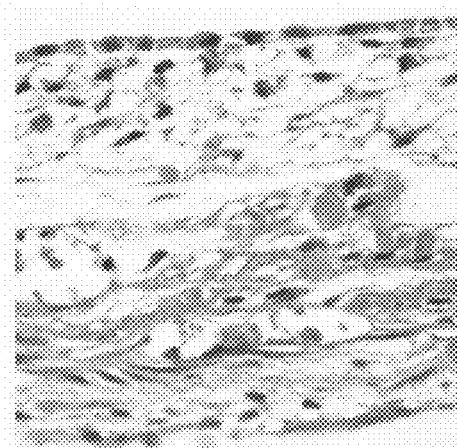

A Three-Dimensional Renal Tubule Model Fabricated With Different Concentrations of Primary Renal Epithelial Cells An interstitial layer comprising a 50:50 ratio of fibroblasts to endothelial cells was bioprinted into each well of a 24-well plate. The constructs were incubated with either $1.25 \times 10^5$ (FIGS. 17A and B), $2.5 \times 10^5$ (FIG. 17C), or $5.0 \times 10^5$ (FIG. 17D), RPTEC cells in the presence (FIGS. 17B, C and D), or absence (FIG. 17A) of media containing 2% FBS. Histology was taken on day 11 and H & E stained.

Example 7

Toxicity Assays Using Renal Tubule Models

To determine the suitability of the renal tubule models for in vitro toxicity assays experiments were conducted using the common cytotoxic agents amphotericin B, cisplatin, and TGFβ (FIG. 18-FIG. 23). Renal tubule models were printed according to methods of the previous examples.

Figure 18:
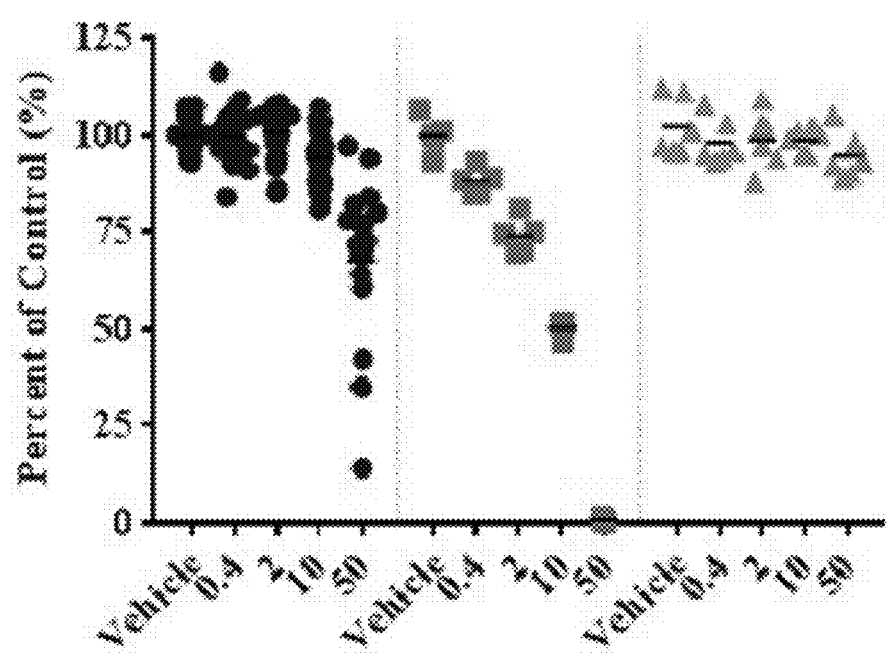
FIG. 18 shows a comparison of a toxicity test using amphotericin B comparing the response of 3D renal tubule model with that of a standard 2D co-culture model.

FIG. 18 shows amphotericin B (AmpB) toxicity, by alamarBlue assay, in bioprinted 3D renal tubule models comprising a layer of interstitial tissue and epithelial tissue (circles); standard 2D co-culture of hTERT RPTEC (squares); and interstitial tissue alone (triangles). Interstitial tissue alone was resistant to AmpB treatment, while the 3D renal tubule model showed dose dependent cytotoxicity.

Figure 19A:
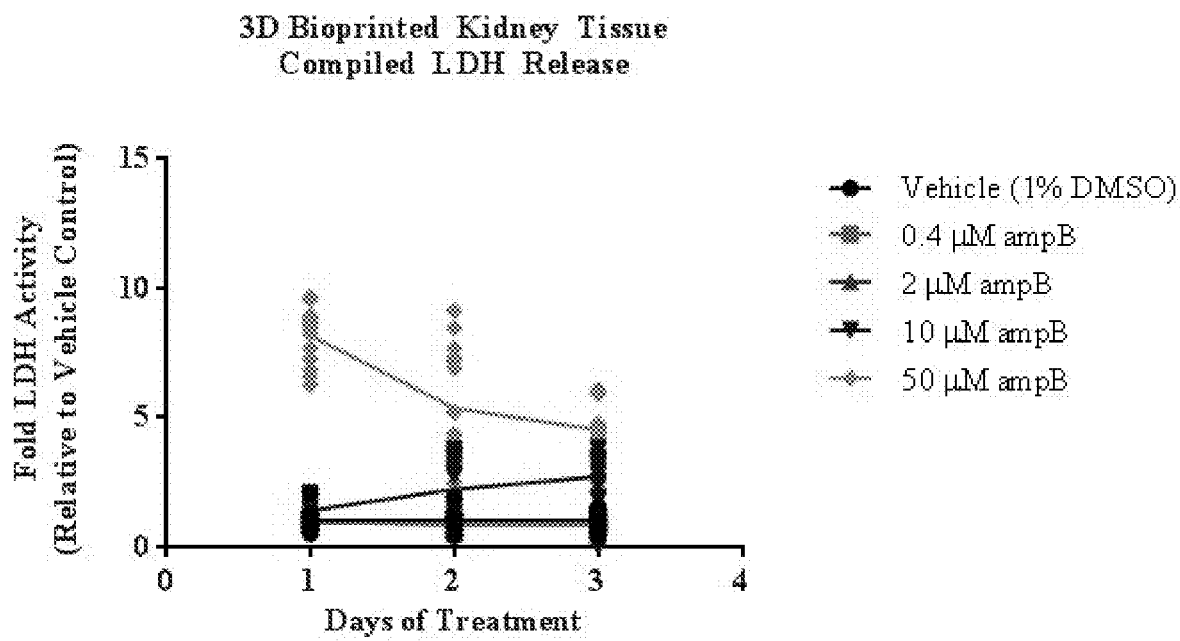
FIGS. 19A and 19B show examples of amphotericin B (AmpB) toxicity tests using a 3D renal tubule model.
Figure 19B:
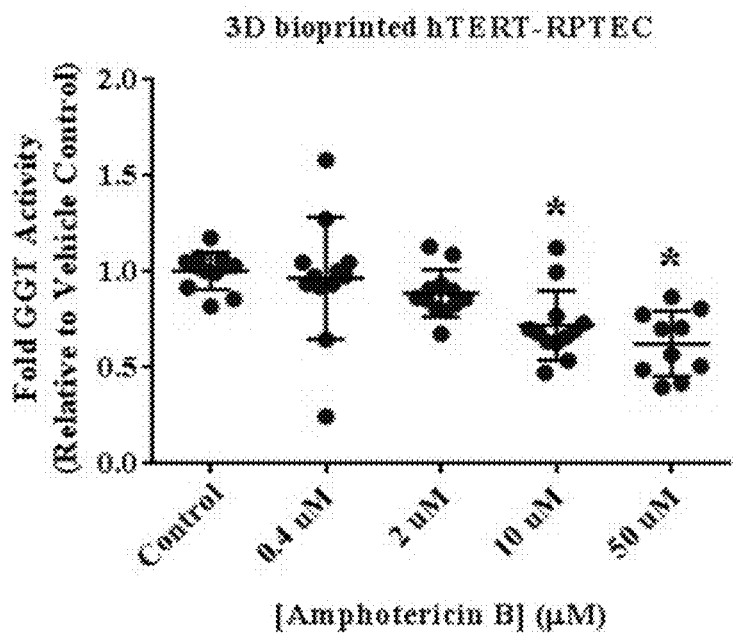
Figure 20A:
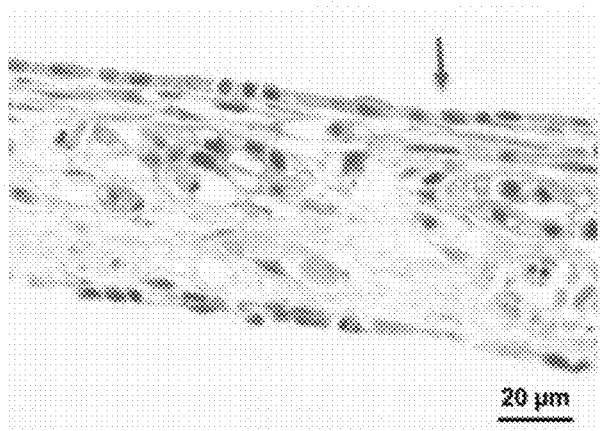
FIGS. 20A, 20B, and 20C depict histology corresponding to FIG. 19, from 3D renal tubule models treated with vehicle (FIG. 20A), 10 μM AmpB (FIG. 20B), or 50 μM AmpB (FIG. 20C).
Figure 20B:
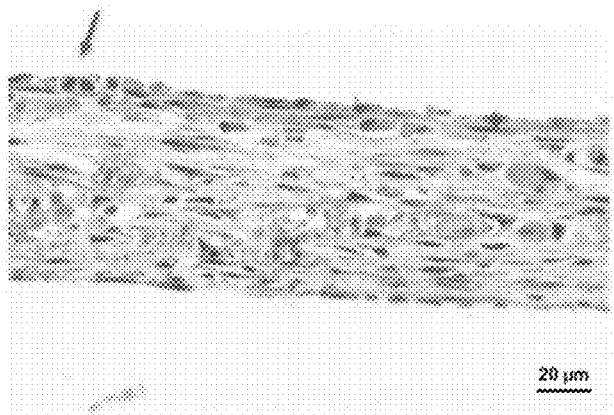
Figure 20C:
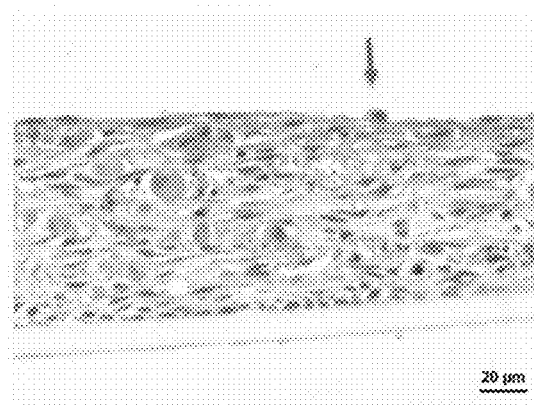

3D renal tubule models show a dose inhibition of epithelial cell function by AmpB. FIG. 19A shows a time-course of lactate dehydrogenase (LDH) release, an indicator of cell toxicity from a 3D renal tubule model treated with varying concentrations of AmpB. A low dose of AmpB results in elevated LDH release by day 3, whereas a high dose results in a high-level of AmpB release by day 1. FIG. 19B shows a dose dependent reduction in GGT activity in response to AmpB treatment. FIG. 20 depicts histology of 3D renal tubule models from FIG. 19B showing epithelial specific cell death at 10 μM (FIG. 20B) and 50 μM (FIG. 20C) of AmpB compared to untreated controls (FIG. 20A).

Figure 21C:
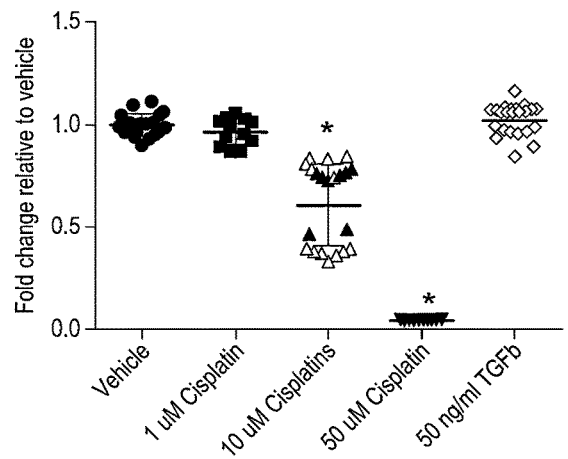
Figure 21C:
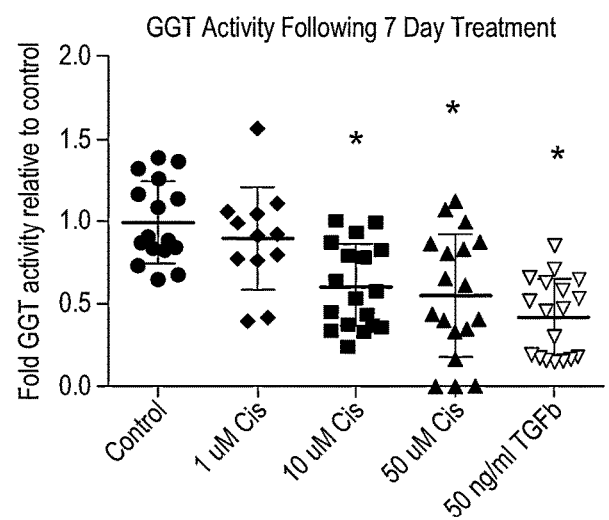
Figure 21C:
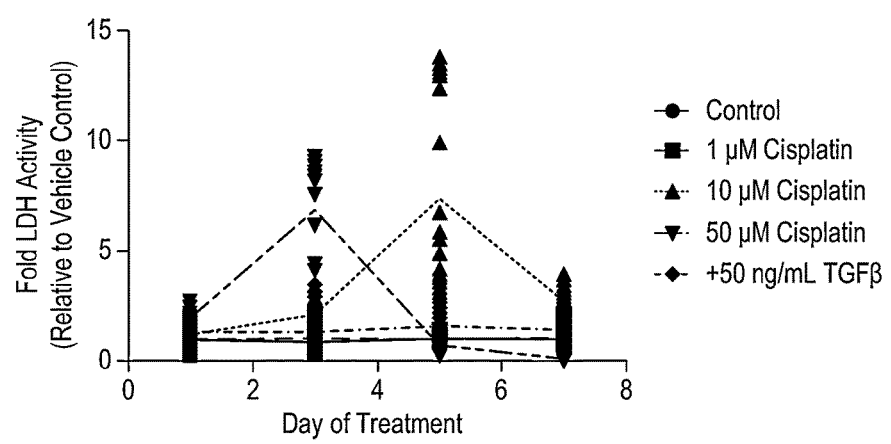
Figure 22A:
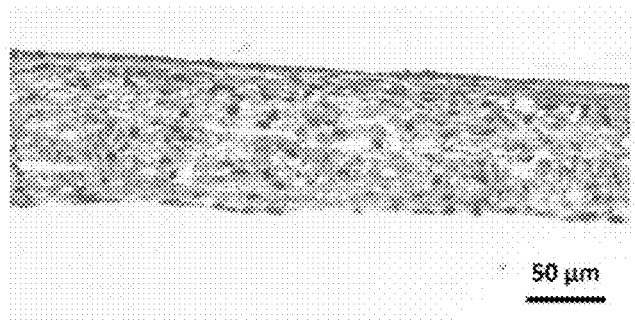
FIGS. 22A, 22B, 22C, and 22D shows Masson's trichrome stained histology corresponding to FIG. 21, from renal tubule models treated with vehicle (FIG. 22A), 10 μM cisplatin (FIG. 22B), 50 μM cisplatin (FIG. 22C), and 50 ng/mL TGFβ (FIG. 22D).
Figure 22B:
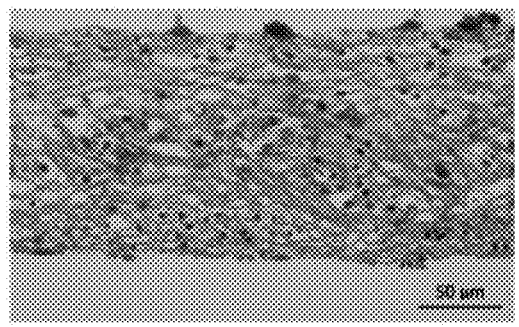
Figure 22C:
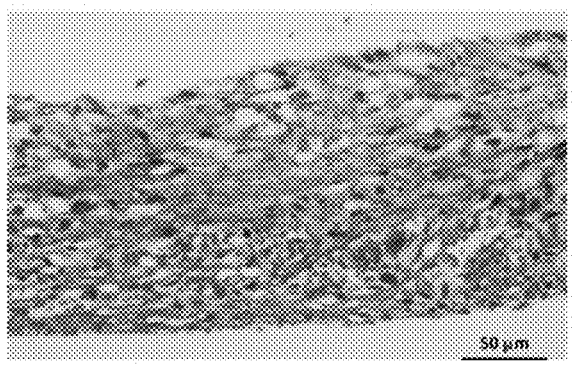
Figure 22D:
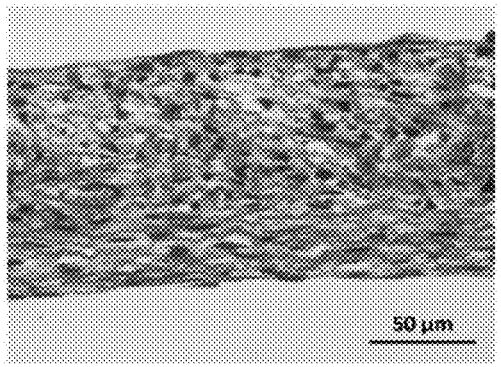

3D renal tubule models show a dose dependent inhibition of epithelial cell function by cisplatin. FIG. 21A shows an increase cytotoxicity in3D renal tube models by AlamarBlue assay. FIG. 21B shows a dose dependent reduction in GGT activity. FIG. 21C shows an increase in LDH release by renal tubule models treated with 50 μM cisplatin at day 3, and with 10 μM cisplatin at day 5. FIG. 22 shows Masson's trichrome staining of renal tubule models treated with vehicle (FIG. 22A), 10 μM cisplatin (FIG. 22B), 50 μM cisplatin (FIG. 22C), and 50 ng/mL TGFβ (FIG. 22D). In particular, treatment with TGFβ shows an increase in fibrosis without the overt cell death of cisplatin treated tissues.

FIG. 23 shows data compiled from experiments comparing the effect of an epithelial layer comprising primary cells (070615-RPTEC) versus an epithelial layer comprising an immortalized cell line (hTERT-RPTEC). Both types of cells exhibited a dose dependent increase in toxicity after treatment with cisplatin, by alamarBlue assay (FIG. 23A), GGT activity (FIG. 23B), and LDH release (FIG. 23C). Notably, primary cells showed enhanced sensitivity to cisplatin in the GGT assay.

Example 8

Effects of Print Surface on Tissue Morphology

Figure 24A:
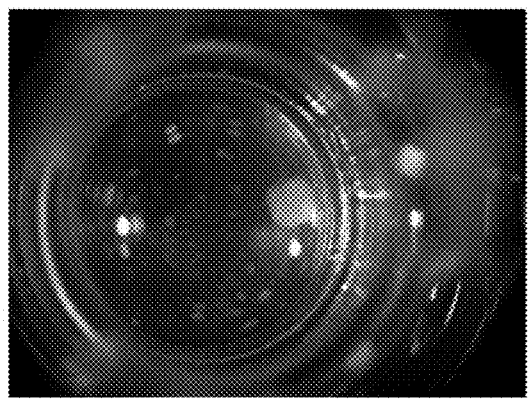
FIGS. 24A and 24B show the effect that pore size has on bioprinted interstitial tissue.
Figure 24B:
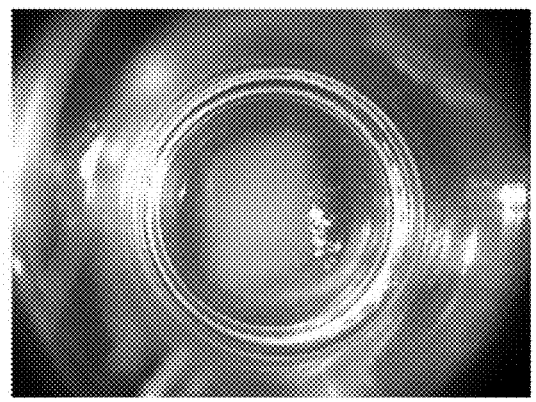

Example 8 describes a bioprinted tubule tissue generated with a border of hydrogel-only Novogel 3.0; this border or a Novogel 1.0 moat is required to facilitate tissue attachment to the transwell membrane when 0.4 μm pore size transwell inserts are used as the culture surface. The bioprinted renal interstitium portion of the tubule model 50:50 renal fibroblast to HUVEC was fabricated on different surfaces and assessed for attachment to the transwell membrane. FIG. 24A demonstrates that the bioprinted tissues float after 3 days in culture in the absence of a border or moat. To assess intact barrier and transporter functions, a tissue that covers the entire culture surface is necessary. To facilitate attachment and outgrowth of the bioprinted tubule tissue and to improve the surface area coverage of the bioprinted tubule model, it is desirable to use a culture surface that encourages tissue attachment in the absence of a border or moat. Shown in FIG. 24B, bioprinted renal interstitial tissues of the preferred embodiment (50:50 renal fibroblast to HUVEC) attach and spread on 1 μm pore size membrane in the absence of any moat or hydrogel border.

Example 9

Long Term Viability of Renal Tubule Models in Culture

Figure 25A:
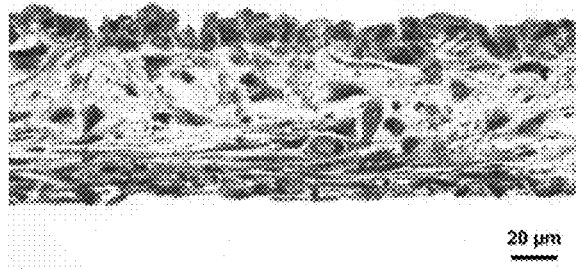
FIGS. 25A, 25B, and 25C show long-term viability of 3D renal tubule models in culture by H & E staining of histology.
Figure 25B:
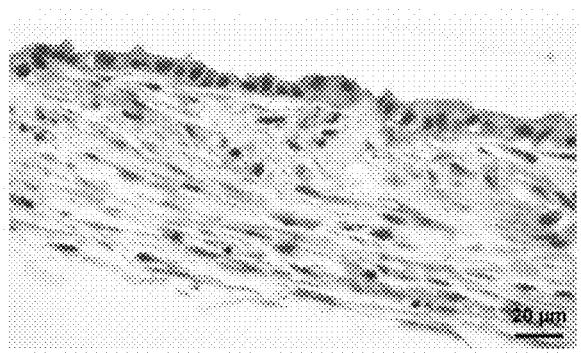
Figure 25C:
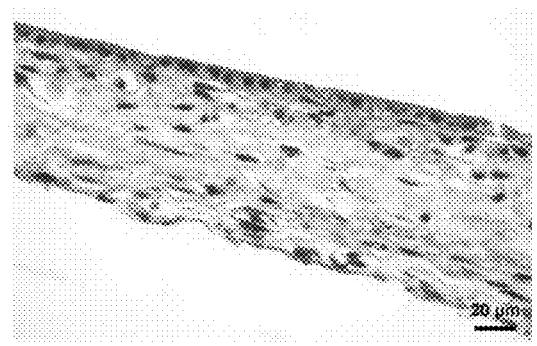

One advantage of the 3D renal tubule models of this disclosure is sustained viability in culture. In many cases the viability persists much longer than the viability of normal 2D culture or tissue explants. FIG. 25 shows that 3D renal tubule models at 6 days (FIG. 25A), 10 days (FIG. 25B) and 27 (FIG. 25C) days in culture.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

What is claimed is:

1. A method of assessing the renal toxicity of a therapeutic agent, the method comprising:
   a. contacting the therapeutic agent with a three-dimensional, engineered, bioprinted, biological renal tubule model comprising:
      i. a layer of renal interstitial tissue, the renal interstitial tissue comprising renal fibroblasts and endothelial cells, and
      ii. a layer of renal epithelial tissue, the renal epithelial tissue comprising renal tubular epithelial cells from a subject with a disease that affects kidney function, wherein the fibroblasts and endothelial cells are present in a ratio of fibroblasts to endothelial cells at which the renal tubule model is planar six days post-printing;
   b. measuring viability or functionality of the renal tubular epithelial cells; and
   c. assessing the renal toxicity of the therapeutic agent based on the measured viability or functionality of the renal tubular epithelial cells.

2. The method of claim 1, wherein the renal epithelial tissue comprises renal tubular epithelial cells from a subject with a polycystic kidney disease, diabetes mellitus type II, or renal cell carcinoma.

3. The method of claim 1, wherein the renal tubule model further comprises a layer of basement membrane between the layer of renal interstitial tissue and the layer of renal epithelial tissue.

4. The method of claim 1, wherein the renal tubular epithelial cells are polarized, and/or wherein the renal tubular epithelial cells are the only cells present in the layer of renal epithelial tissue.

5. The method of claim 1, wherein the fibroblasts and endothelial cells are the only cells present in the layer of renal interstitial tissue, and/or wherein the fibroblasts and endothelial cells are present in the layer of renal interstitial tissue at a ratio of about 50:50 fibroblasts to endothelial cells.

6. The method of claim 1, wherein the renal tubule model is between about 50 μm and about 150 μm thick.

7. A method of testing the viability of renal tubular epithelial cells in the presence of a therapeutic agent, comprising:
   a. contacting the therapeutic agent with a three-dimensional, engineered, bioprinted, biological renal tubule model comprising:
      i. a layer of renal interstitial tissue, the renal interstitial tissue comprising renal fibroblasts and endothelial cells, and
      ii. a layer of renal epithelial tissue, the renal epithelial tissue comprising renal tubular epithelial cells from a subject with a disease that affects kidney function, wherein the fibroblasts and endothelial cells are present in a ratio of fibroblasts to endothelial cells at which the renal tubule model is planar six days post-printing; and
   b. measuring gamma glutamyl-transferase (GGT) activity in the renal tubule model that has been contacted with the therapeutic agent compared to a control renal tubule model that has not been contacted with the therapeutic agent;
   wherein decreased GGT activity in the renal tubule model that has been contacted with the therapeutic agent compared to the control renal tubule model is indicative of reduced viability of the renal tubular epithelial cells.

8. The method of claim 7, wherein the renal epithelial tissue comprises renal tubular epithelial cells from a subject with a polycystic kidney disease, diabetes mellitus type II, or renal cell carcinoma.

9. The method of claim 7, wherein the renal tubule model further comprises a layer of basement membrane between the layer of renal interstitial tissue and the layer of renal epithelial tissue.

10. The method of claim 7, wherein the renal tubular epithelial cells are polarized, and/or wherein the renal tubular epithelial cells are the only cells present in the layer of renal epithelial tissue.

11. The method of claim 7, wherein the fibroblasts and endothelial cells are the only cells present in the layer of renal interstitial tissue, and/or wherein the fibroblasts and endothelial cells are present in the layer of renal interstitial tissue at a ratio of about 50:50 fibroblasts to endothelial cells.

12. The method of claim 7, wherein the renal tubule model is between about 50 μm and about 150 μm thick.

13. A method of testing the effect of a therapeutic agent on a renal transport molecule, comprising:
   a. contacting the therapeutic agent with a three-dimensional, engineered, bioprinted, biological renal tubule model comprising:
      i. a layer of renal interstitial tissue, the renal interstitial tissue comprising renal fibroblasts and endothelial cells, and
      ii. a layer of renal epithelial tissue, the renal epithelial tissue comprising renal tubular epithelial cells from a subject with a disease that affects kidney function, wherein the fibroblasts and endothelial cells are present in a ratio of fibroblasts to endothelial cells at which the renal tubule model is planar six days post-printing; and b. measuring the transport molecule activity in the renal tubule model that has been contacted with the therapeutic agent compared to a control renal tubule model that has not been contacted with the therapeutic agent.

14. The method of claim 13, wherein the transport molecule activity is excretion and/or uptake of macromolecules.

15. The method of claim 13, wherein the transport molecule activity is albumin transport.

16. The method of claim 13, wherein the renal epithelial tissue comprises renal tubular epithelial cells from a subject with a polycystic kidney disease, diabetes mellitus type II, or renal cell carcinoma.

17. The method of claim 13, wherein the renal tubule model further comprises a layer of basement membrane between the layer of renal interstitial tissue and the layer of renal epithelial tissue.

18. The method of claim 13, wherein the renal tubular epithelial cells are polarized, and/or wherein the renal tubular epithelial cells are the only cells present in the layer of renal epithelial tissue.

19. The method of claim 13, wherein the fibroblasts and endothelial cells are the only cells present in the layer of renal interstitial tissue, and/or wherein the fibroblasts and endothelial cells are present in the layer of renal interstitial tissue at a ratio of about 50:50 fibroblasts to endothelial cells.

20. The method of claim 13, wherein the renal tubule model is between about 50 μm and about 150 μm thick.

* * * * *